US009221879B2

(12) United States Patent
Bovin et al.

(10) Patent No.: US 9,221,879 B2
(45) Date of Patent: *Dec. 29, 2015

(54) MULTILIGAND CONSTRUCTS

(71) Applicant: SEMIOTIK LLC, Moscow (RU)

(72) Inventors: Nikolai Vladimirovich Bovin, Moscow (RU); Alexander Alexandrovich Chinarev, Moscow (RU); Alexander Borisovich Tuzikov, Moscow (RU)

(73) Assignee: SEMIOTIK LLC, Moscow (RU)

( * ) Notice: Subject to any disclaimer, the term of this patent is extended or adjusted under 35 U.S.C. 154(b) by 28 days.

This patent is subject to a terminal disclaimer.

(21) Appl. No.: 14/162,163

(22) Filed: Jan. 23, 2014

(65) Prior Publication Data

US 2014/0135477 A1 May 15, 2014

Related U.S. Application Data

(63) Continuation of application No. 12/998,345, filed as application No. PCT/EA2008/000006 on Oct. 13, 2008, now Pat. No. 8,674,061.

(51) Int. Cl.

*C07K 7/02* (2006.01)
*C07K 9/00* (2006.01)
*A61K 47/48* (2006.01)
*C07H 15/04* (2006.01)
*C07H 15/26* (2006.01)

(52) U.S. Cl.
CPC ........... *C07K 9/001* (2013.01); *A61K 47/48253* (2013.01); *C07H 15/04* (2013.01); *C07H 15/26* (2013.01); *C07K 9/00* (2013.01)

(58) Field of Classification Search
CPC .......................... A61K 47/48253; C07K 9/001
See application file for complete search history.

(56) References Cited

U.S. PATENT DOCUMENTS 7,294,615 B1 11/2007 Bovin et al.
2003/0157115 A1 8/2003 Bay et al.
2003/0229017 A1 12/2003 Wu et al.
2004/0077826 A1 4/2004 Koganty et al.

FOREIGN PATENT DOCUMENTS

WO WO 2005/090368 A1 9/2005

OTHER PUBLICATIONS

Tuzikov et al. "Polyglycine II Nanosheets: Supramolecular Antivirals?" ChemBioChem 2003, 4, 147-154.*

Nishimura, Shin-Ichiro, et al; "Specific crosslinking of cell adhesive molecules by heterobifunctional glycopetide synthesised on the basis of chemoenzymatic strategy"; *Chemical communication*; vol. 15; pp. 1435-1436 (1999).

Shaikh, Harun, A., et al; Synthesis of glycocluster peptides; *Carbohydrate research*, vol. 343; pp. 1665-1674 (2008).
Specification (371 of PCT/NZ2008/000266, filed Oct. 13, 2008) of co-pending U.S. Appl. No. 12/734,072, filed Apr. 8, 2010.
Frame, et al; "Synthetic glycolipid modification of red blood cell membranes"; *Transfusion*, vol. 47, No. 5; pp. 876-882 (2007).
Nishimura, Shin-Ichiro, et al; "Specific crosslinking of cell adhesive molecules by heterobifunctional glycopeptide synthesised on the basis of chemoenzymatic strategy"; *Chemical communication*; vol. 15; pp. 1435-1436 (1999).

Li, et al; "Novel Inhibitor Design for Hemmagglutinin against H1N1 Influenza Virus by Core Hopping Method" Plos ONE, Nov. 2011, vol. 6, No. 11, pp. 1-6.

Chinarev, Alexander A., et al; "Tetravalent Blockers for Influenza Virus Hemagglutinin"; *Sialobiology and Other Novel Forms of Glycosylation*, Y. Inoue, Y.C. Lee and F.A. Troy II (eds.) p. 135-143 (1999).

* cited by examiner

*Primary Examiner* — Christina Bradley
(74) *Attorney, Agent, or Firm* — Nixon & Vanderhye P.C.

(57) ABSTRACT

Multiligand constructs and intermediate multivalent constructs for use in their preparation are described. The multiligand constructs have utility in diagnostic and therapeutic applications.

11 Claims, 11 Drawing Sheets

MULTILIGAND CONSTRUCTS

This application is a continuation of U.S. application Ser. No. 12/998,345, filed Jul. 6, 2011, pending, which is a 371 of PCT/EA2008/000006, filed 13 Oct. 2008, the entire contents of each of which are hereby incorporated by reference.

TECHNICAL FIELD

The invention relates to multiligand constructs for use in diagnostic and therapeutic applications, and intermediate multivalent constructs for use in the preparation of the multiligand constructs.

In particular, the invention relates to tri- and tetra-ligand constructs for use in the inhibition of ligand-receptor mediated events such as viral infection of cells and the initiation of immune responses.

BACKGROUND ART

Many biological interactions are mediated by binding between a multivalent receptor and its target. Such multivalent binding occurs between virus receptors and ligands expressed at the surface of target cells prior to infection.

Antibodies (IgG, IgM) bind antigen via multiple binding sites prior to initiation of the complement cascade (Alzari et al (1988); Merritt and Hol (1995); Ascenzi et al (2000); Reni (1995)).

The events that occur subsequent to the initial multivalent binding event (e.g. viral infection of cells, transfusion/tissue rejection) are often deleterious to the host.

Multivalent binding events are characterized by low dissociation constants ($K_d$). A compound intended to be administered to a host as a competitive inhibitor of the binding event must have a significantly higher affinity for the receptor to provide a therapeutic effect.

One approach to providing competitive inhibitors of multivalent binding is to design compounds comprising multiple ligands for the receptor.

Dendrimeric molecules are an example of compounds comprising multiple ligands designed to participate in multivalent binding with a receptor (Tomalia et al (1990); Tsvetkov et al (2002); Jayaraman et al (1997)).

A limitation of these dendrimeric molecules is that they are of high molecular weight and the intramolecular ligand separation is poorly defined.

A further limitation of these dendrimeric molecules is that many of the ligands of the molecule do not participate in productive interactions with the receptor.

Antennary molecules are another example of compounds comprising multiple ligands designed to participate in multivalent binding with a receptor (Fon et al (2000)).

An advantage of antennary molecules is that they comprise fewer ligands—typically three to five—than their dendrimeric counterparts.

The use of rigid carrier molecules or templates is yet another example of the design of compounds comprising multiple ligands for a receptor.

Candidate carrier molecules include cyclodextrins, calixarenes and porphirines (Kiessling and Pohl (1996); Matsuura et al (2004); Mellet et al (2002); Lundquist and Toone (2002); Fon et al (2000)).

A limitation of these rigid carrier molecules is that their dimensions place a constraint on the possible intra-molecular separation of the conjugated ligands (circa 10 Å).

The dimensions of carrier molecules is in contrast with the separation of the binding sites of multivalent receptors such as viruses (e.g. influenza virus hemaglutinin (HA) >50 Å) and antibodies (>100 Å).

It is an object of the invention to provide molecules capable of inhibiting multivalent binding events.

It is an object of the invention to provide a method of preparing inhibitors of the interaction between a multivalent receptor and its target where the intra-molecular separation of the ligands is pre-determined.

These objects are to be read disjunctively with the object of to at least provide a useful choice.

DISCLOSURE OF INVENTION

In a first aspect the invention provides multiligand constructs of the structure:

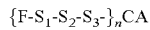

where:
  F is a ligand for a receptor;
  $S_1$-$S_2$-$S_3$ is a spacer linking F to C; and
  n is 3 when A is $CH_3$, or n is 4 when A is absent.

Preferably, the receptor is selected from the group consisting of: influenza virus hemagglutinin (HA) and anti-A or anti-B immunoglobulin.

Preferably, F is a ligand selected from the group consisting of: Neu5Acα2-6Galβ1-4GlcNAcβ-O— (6'SLN), GalNAcα1-3(Fucα1-2)Galβ-O— ($A_{tri}$) and Galα1-3(Fucα1-2)Galβ-O— ($B_{tri}$)

Preferably, the spacer is a rigid spacer.

Preferably, $S_1$ is selected from the group consisting of: 1-amino-$C_{2-4}$-alkyl. More preferably, $S_1$ is selected from the group consisting of: 1-aminopropyl.

Preferably, $S_2$ is selected from the group consisting of: —CO(CH$_2$)$_3$CO—, —CO(CH$_2$)$_4$CO—, and —CO(CH$_2$)$_5$CO—. More preferably, $S_2$ is selected from the group consisting of: —CO(CH$_2$)$_4$CO—.

Preferably, $S_3$ is of the structure:

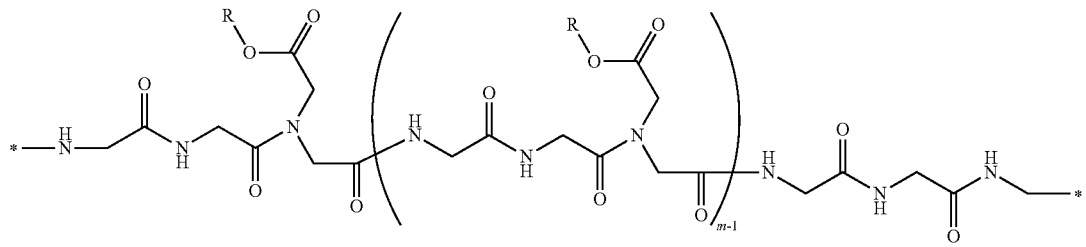

where:
R is CH$_3$ or H;
m is an integer between 1 and 5; and
* is other than H.

In a first embodiment of the first aspect the invention provides a multiligand construct of the structure:

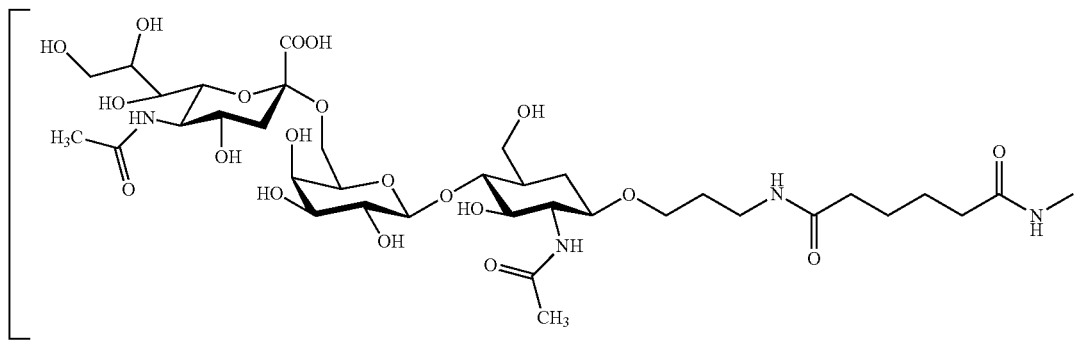

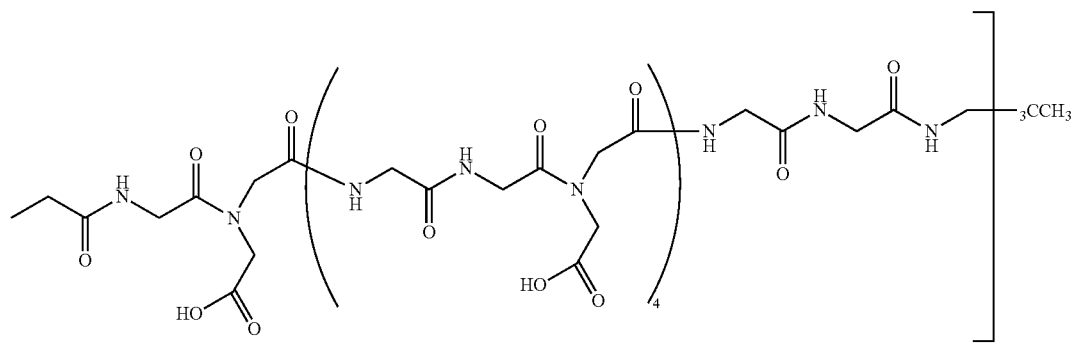

designated {6'SLN-S$_1$-S$_2$-[Gly$_2$(CMGly)]$_5$Gly$_2$-NHCH$_2$}$_3$CCH$_3$ (where S$_1$ is 1-aminopropyl and S$_2$ is —CO(CH$_2$)$_4$CO—).

In a second embodiment of the first aspect the invention provides a multiligand construct of the structure:

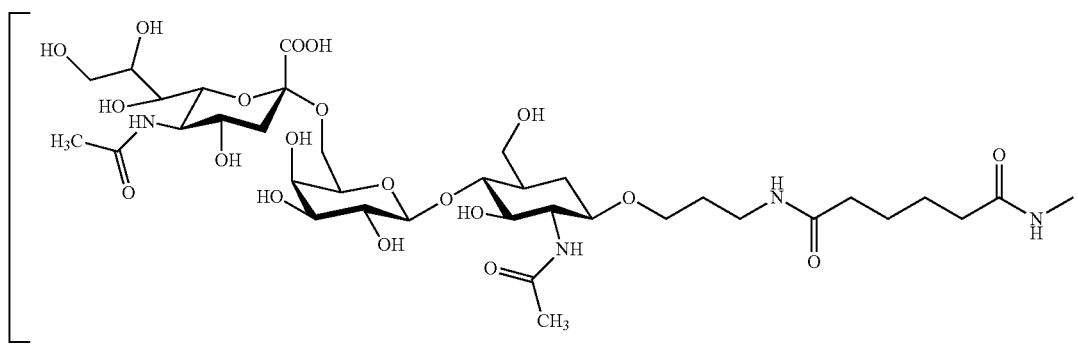

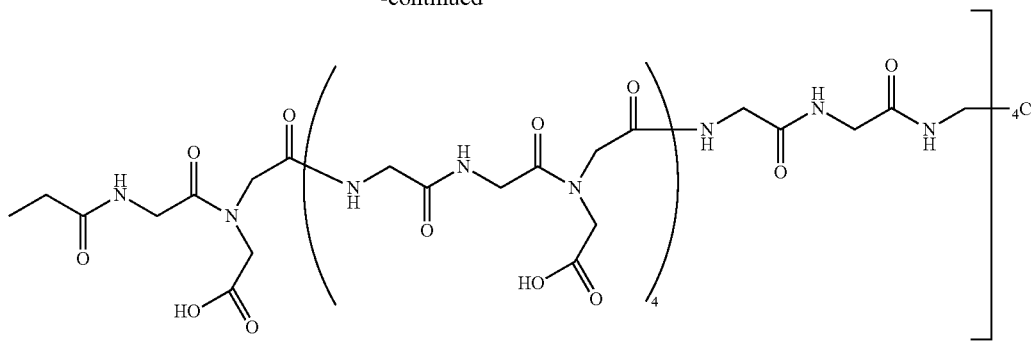

designated {6'SLN-$S_1$-$S_2$-[$Gly_2$(CMGly)]$_5$$Gly_2$-NHCH$_2$}$_4$C (where $S_1$ is 1-aminopropyl and $S_2$ is —CO(CH$_2$)$_4$CO—).

In a third embodiment of the first aspect the invention provides a multiligand construct of the structure:

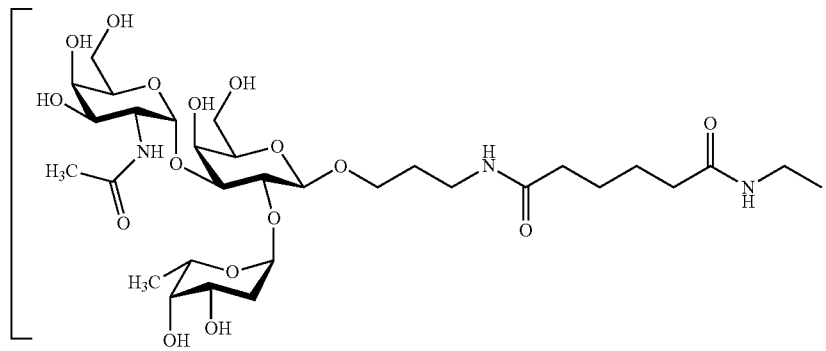

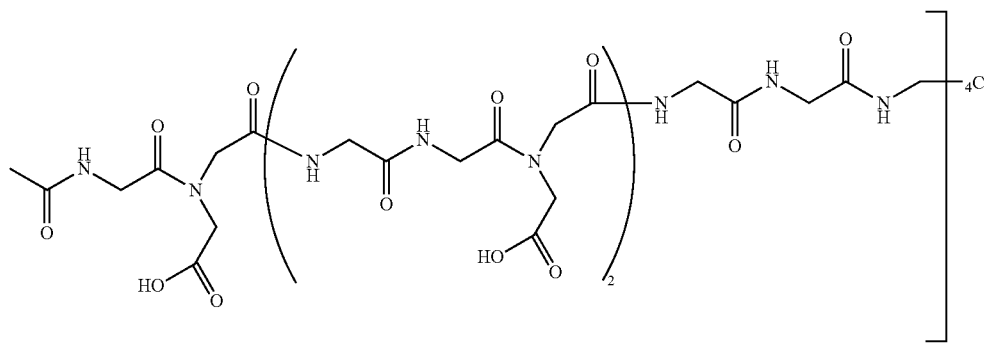

designated {$A_{tri}$-$S_1$-$S_2$-[$Gly_2$(CMGly)]$_3$$Gly_2$-NHCH$_2$}$_4$C (where $S_1$ is 1-aminopropyl and $S_2$ is —CO(CH$_2$)$_4$CO—).

In a fourth embodiment of the first aspect the invention provides a multiligand construct of the structure:

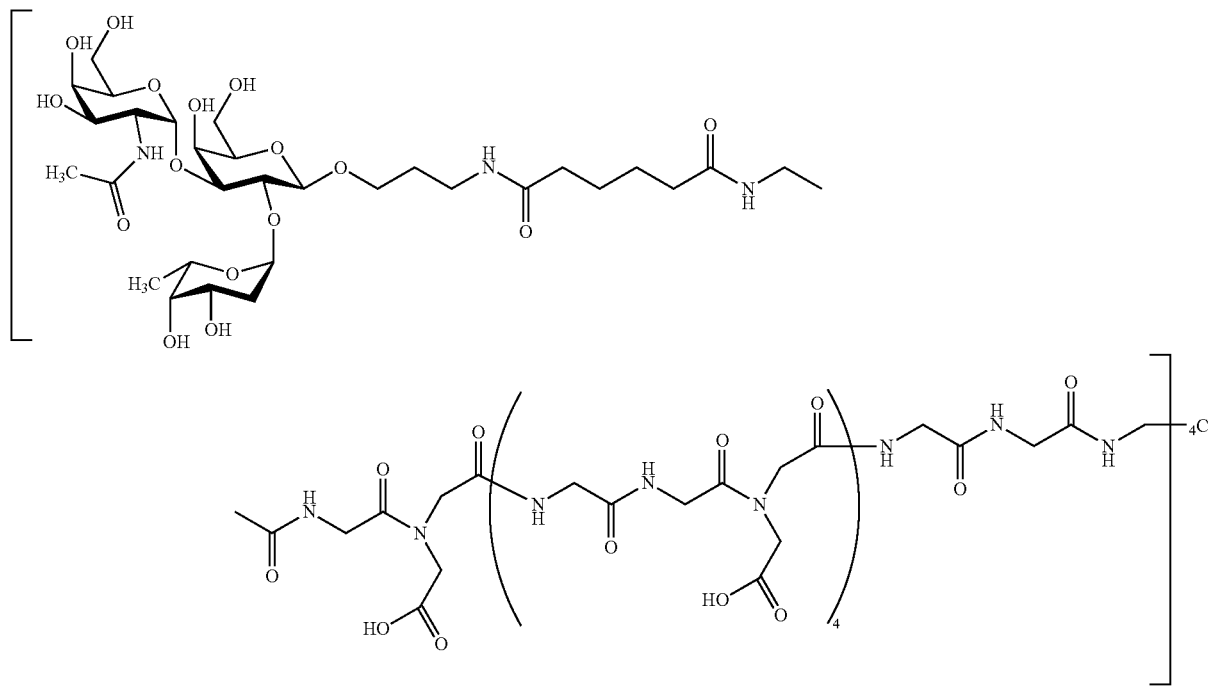

designated {A$_{tri}$-S$_1$-S$_2$-[Gly$_2$(CMGly)]$_5$Gly$_2$-NHCH$_2$}$_4$C
(where S$_1$ is 1-aminopropyl and S$_2$ is —CO(CH$_2$)$_4$CO—).

In a fifth embodiment of the first aspect the invention provides a multiligand construct of the structure:

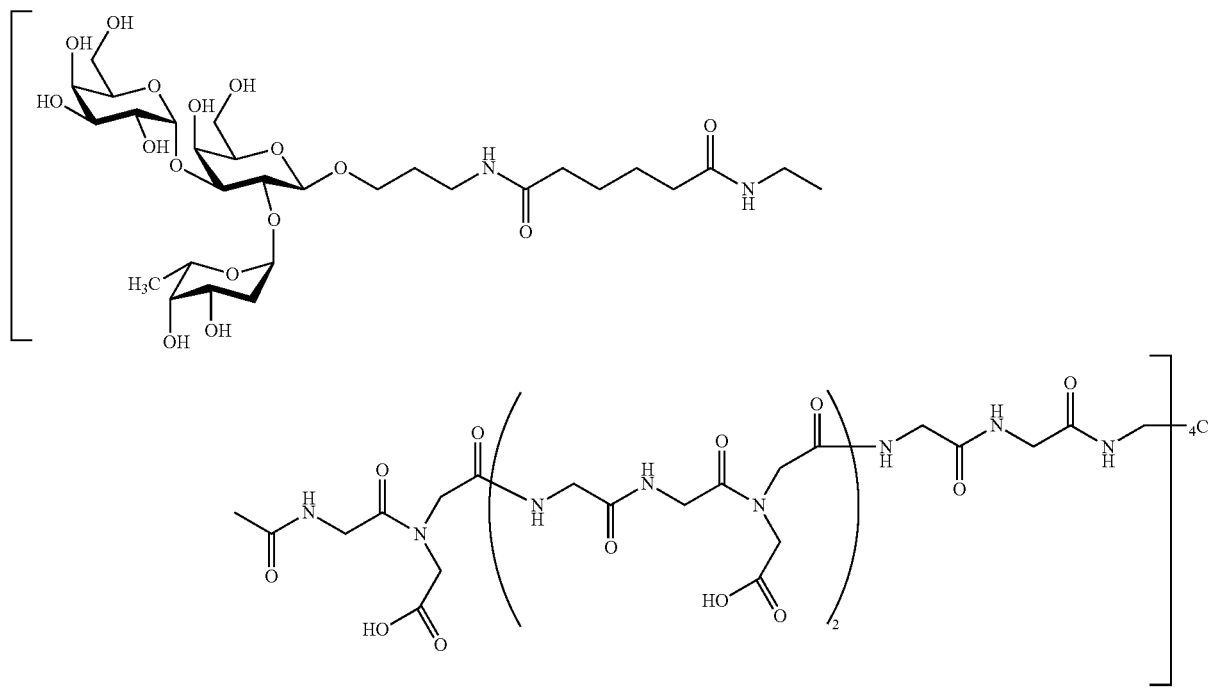

designated {B$_{tri}$-S$_1$-S$_2$-[Gly$_2$(CMGly)]$_3$Gly$_2$-NHCH$_2$}$_4$C
(where S$_1$ is 1-aminopropyl and S$_2$ is —CO(CH$_2$)$_4$CO—).

In a sixth embodiment of the first aspect the invention provides a multiligand construct of the structure:

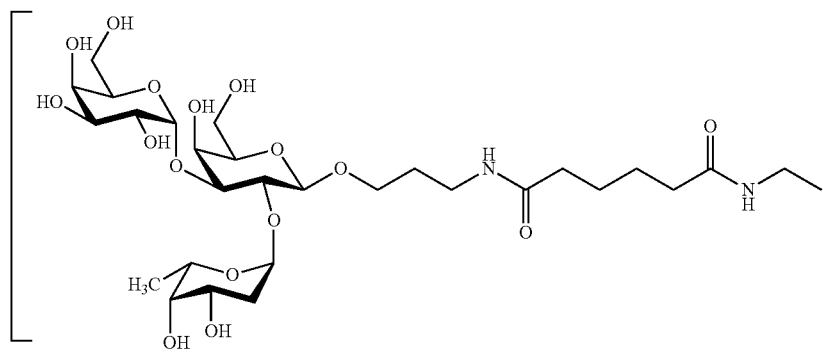

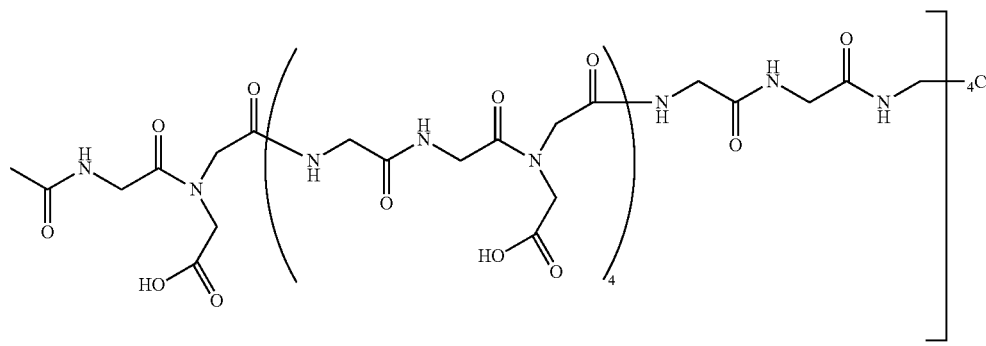

designated {B$_{tri}$-S$_1$-S$_2$-[Gly$_2$(CMGly)]$_5$Gly$_2$-NHCH$_2$}$_4$C (where S$_1$ is 1-aminopropyl and S$_2$ is —CO(CH$_2$)$_4$CO—).

In a second aspect the invention provides constructs for use in the preparation of multiligand constructs of the first aspect of the invention of the structure:

{H-S$_3$-}$_n$CA where:
  S$_3$ is a spacer linking H to C; and
  n is 3 when A is CH$_3$, or n is 4 when A is absent.
  Preferably the spacer is a rigid spacer.
  Preferably, S$_3$ is of the structure:

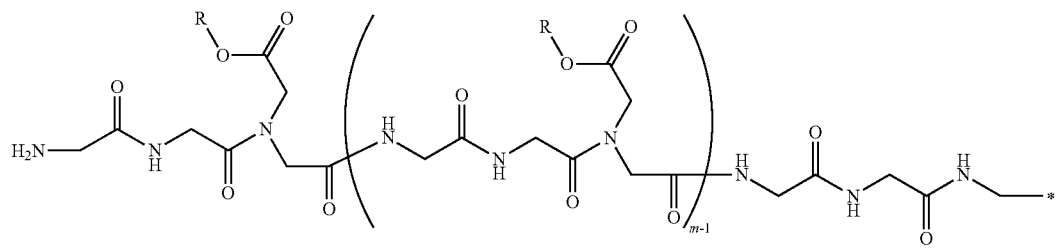

where:
R is CH$_3$ or H;
m is an integer between 1 and 5; and
* is other than H.

In a first embodiment of the second aspect the invention provides a construct of the structure:

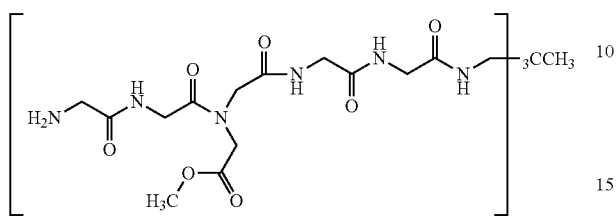

designated {H-[Gly$_2$ (MCMGly)]Gly$_2$-NHCH$_2$}$_3$CCH$_3$.

In a second embodiment of the second aspect the invention provides a construct of the structure:

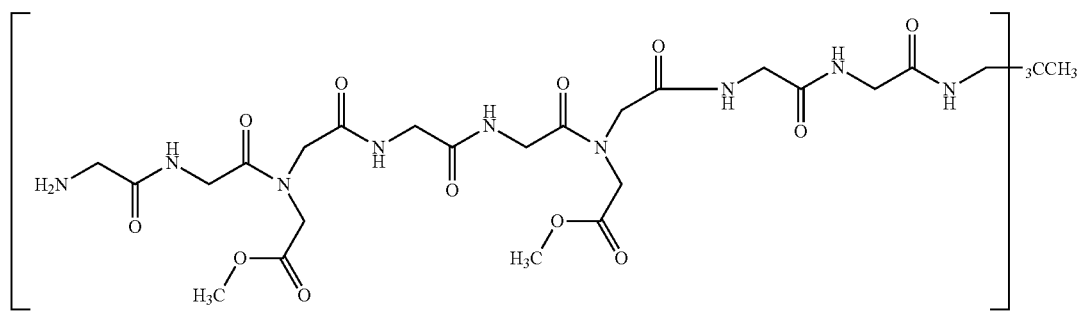

designated {H-[Gly$_2$(MCMGly)]$_2$Gly$_2$-NHCH$_2$}$_3$CCH$_3$.

In a third embodiment of the second aspect the invention provides a construct of the structure:

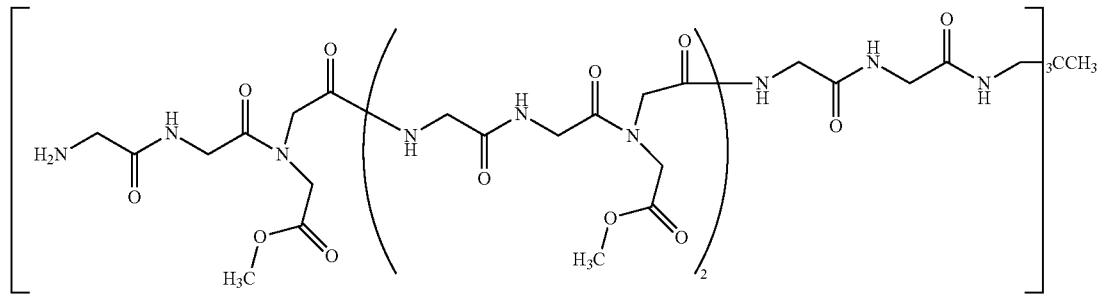

designated {H-[Gly$_2$(MCMGly)]$_3$Gly$_2$-NHCH$_2$}$_3$CCH$_3$.

In a fourth embodiment of the second aspect the invention provides a construct of the structure:

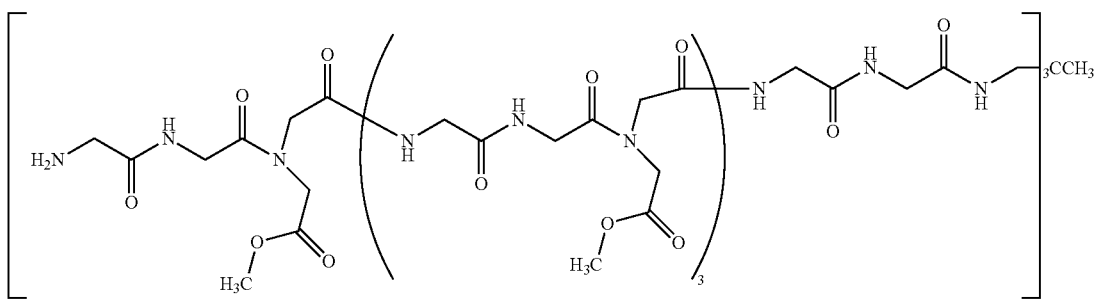

designated {H-[Gly$_2$(MCMGly)]$_4$Gly$_2$-NHCH$_2$}$_3$CCH$_3$.

In a fifth embodiment of the second aspect the invention provides a construct of the structure:

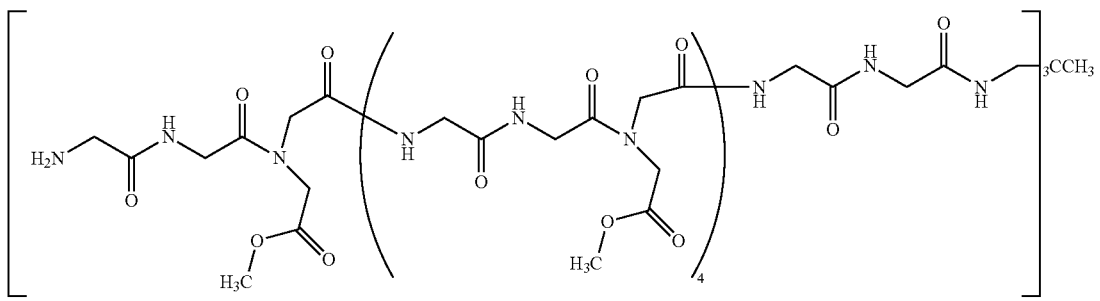

designated {H-[Gly$_2$(MCMGly)]$_5$Gly$_2$-NHCH$_2$}$_3$CCH$_3$.

In a sixth embodiment of the second aspect the invention provides a construct of the structure:

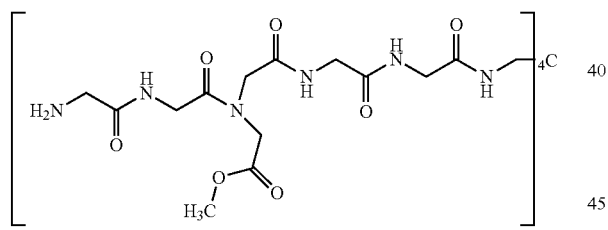

designated {H-[Gly$_2$(MCMGly)]Gly$_2$-NHCH$_2$}$_4$C.

In a seventh embodiment of the second aspect the invention provides a construct of the structure:

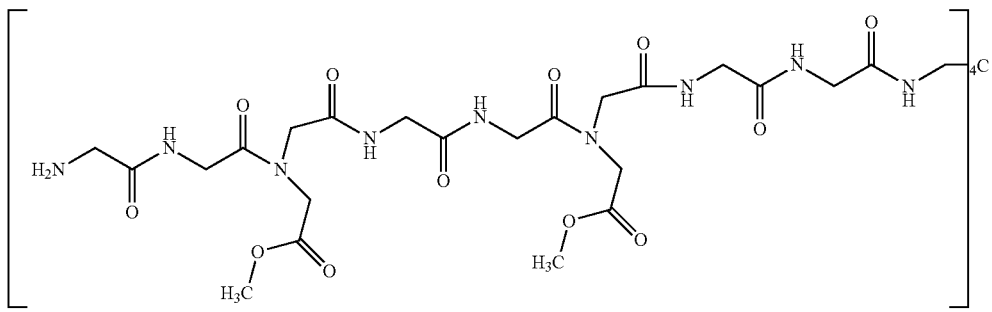

designated {H-[Gly$_2$(MCMGly)]$_2$Gly$_2$-NHCH$_2$}$_4$C.

In a eighth embodiment of the second aspect the invention provides a construct of the structure:

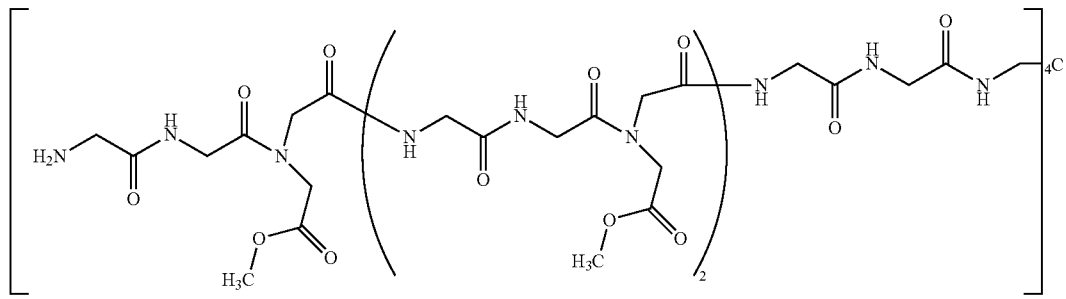

designated {H-[Gly$_2$(MCMGly)]$_3$Gly$_2$-NHCH$_2$}$_4$C.

In a ninth embodiment of the second aspect the invention provides a construct of the structure:

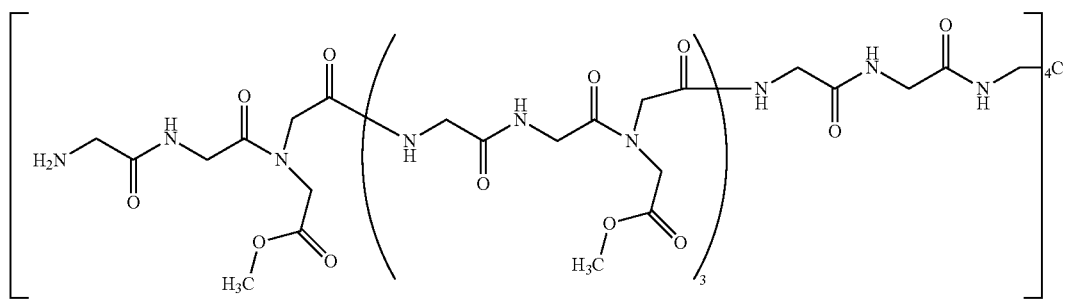

designated {H-[Gly$_2$(MCMGly)]$_4$Gly$_2$-NHCH$_2$}$_4$C.

In a tenth embodiment of the second aspect the invention provides a construct of the structure:

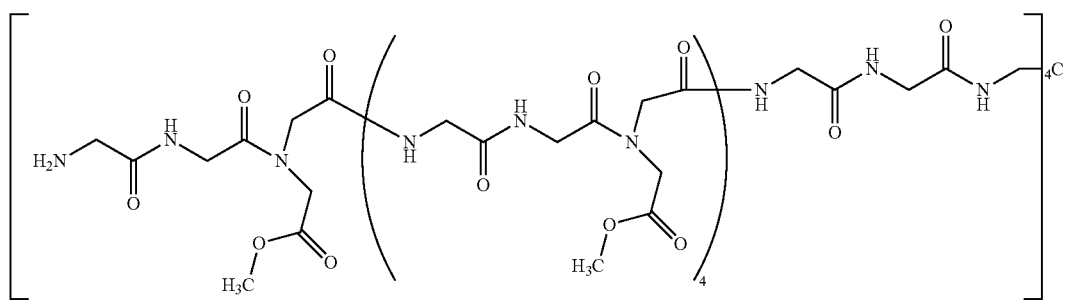

designated {H-[Gly$_2$(MCMGly)]$_5$Gly$_2$-NHCH$_2$}$_4$C.

In a third aspect the invention provides a method of preparing a multiligand construct of the first aspect of the invention via an intermediate multivalent construct of the second aspect of the invention.

Preferably, the method of preparing the multiligand construct of the first aspect of the invention includes the step of:

Reacting an activated ligand derivative of the structure F-S$_1$-S$_2$-A with the intermediate multivalent construct of the second aspect of the invention;

where:
F is the ligand;
S$_1$ is selected from the group consisting of: 1-amino-C$_{2-4}$-alkyl;
S$_2$ is selected from the group consisting of: —CO(CH$_2$)$_3$CO—, —CO(CH$_2$)$_4$CO—, and —CO(CH$_2$)$_5$CO—; and
A is an activator.

Preferably, A is selected from the group consisting of: 4-nitrophenyl (Nph) or N-oxysuccinimide (Nos)

In a fourth aspect the invention provides a method of inhibiting infection of a subject by a virus by administering to the subject an effective amount of a multiligand construct of the first aspect of the invention.

Preferably, the virus is selected from the group consisting of: influenza virus.

Preferably, the administering to the subject is by inhalation.

Preferably, the multiligand construct is of a structure selected from the group consisting of:

designated $\{6'SLN-S_1-S_2-[Gly_2(CMGly)]_5Gly_2-NHCH_2\}_3CCH_3$ (where $S_1$ is 1-aminopropyl and $S_2$ is $-CO(CH_2)_4CO-$); and -continued

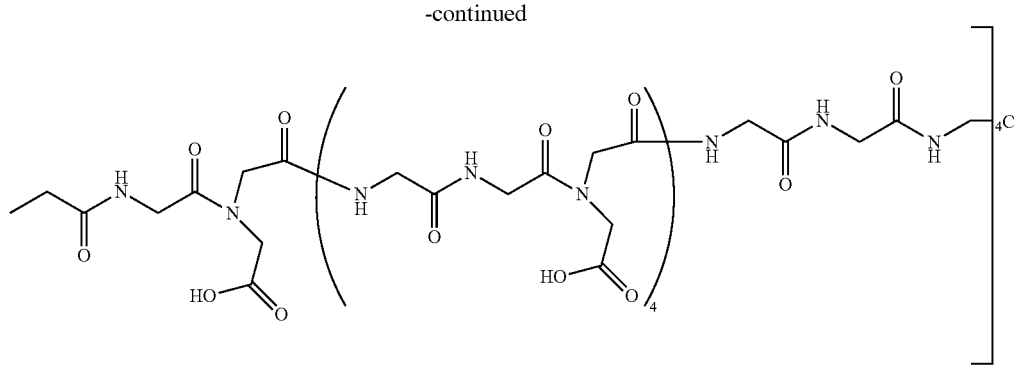

designated $\{6'SLN-S_1-S_2-[Gly_2(CMGly)]_5Gly_2-NHCH_2\}_4C$ (where $S_1$ is 1-aminopropyl and $S_2$ is $—CO(CH_2)_4CO—$).

In a fifth aspect the invention provides a pharmaceutical preparation including a multiligand construct of the first aspect of the invention and pharmaceutically acceptable formulants.

Preferably, the pharmaceutical preparation is of a formulation suitable for administering to a subject by inhalation.

Preferably, the multiligand construct is of a structure selected from the group consisting of:

designated $\{6'SLN-S_1-S_2-[Gly_2(CMGly)]_5Gly_2-NHCH_2\}_3CCH_3$ (where $S_1$ is 1-aminopropyl and $S_2$ is $—CO(CH_2)_4CO—$); and

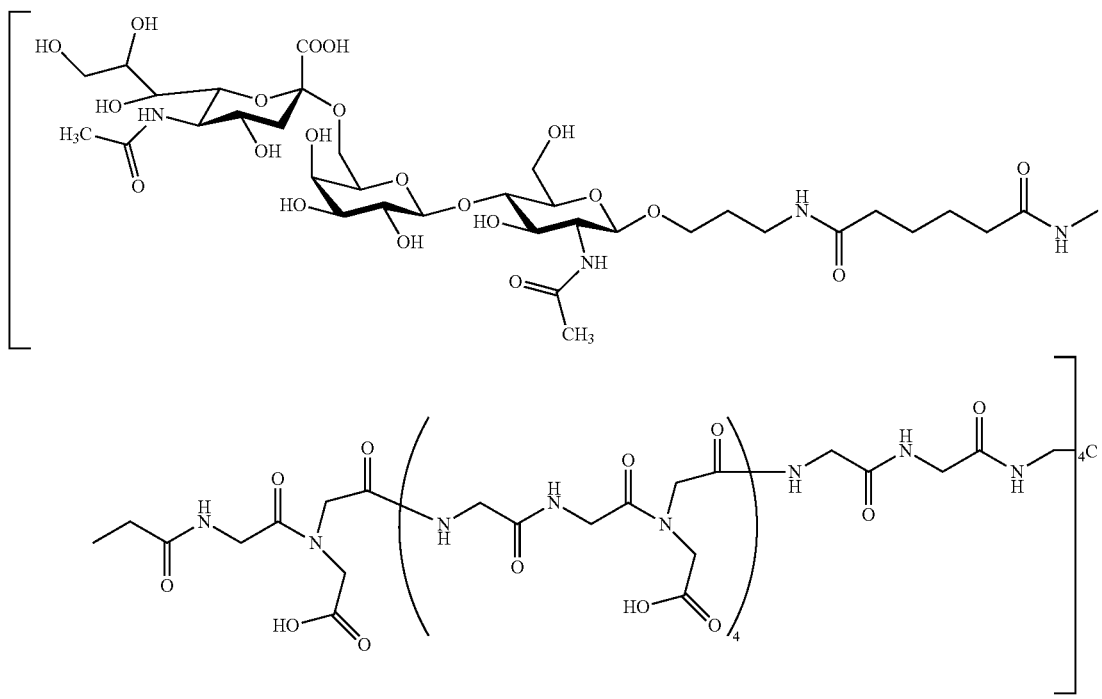

designated {6'SLN-S$_1$-S$_2$-[Gly$_2$(CMGly)]$_5$Gly$_2$-NHCH$_2$}$_4$C (where S$_1$ is 1-aminopropyl and S$_2$ is —CO(CH$_2$)$_4$CO—).

In the description and claims of the specification the following terms and phrases have the meanings provided:

"Glycotope" means the portion of the carbohydrate moiety of a ligand that associates with the binding site of a receptor.

"Ligand" means any molecule or portion of a molecule that binds to one or more macromolecules, such as surface expressed antigens.

"Multiligand" means having a plurality of ligands.

"Pharmaceutically acceptable formulants" means ingredients included in the formulation of a pharmaceutical composition.

"Receptor" means a macromolecule or portion of a macromolecule such as a surface expressed antigen that binds to one or more ligands.

"Vascular system" means the system of vessels that convey fluids such as blood or lymph, or provide for the circulation of such fluids.

Exemplary embodiments of the invention will now be described in detail with reference to the Figures of the accompanying drawings pages.

DETAILED DESCRIPTION

Figure 1:
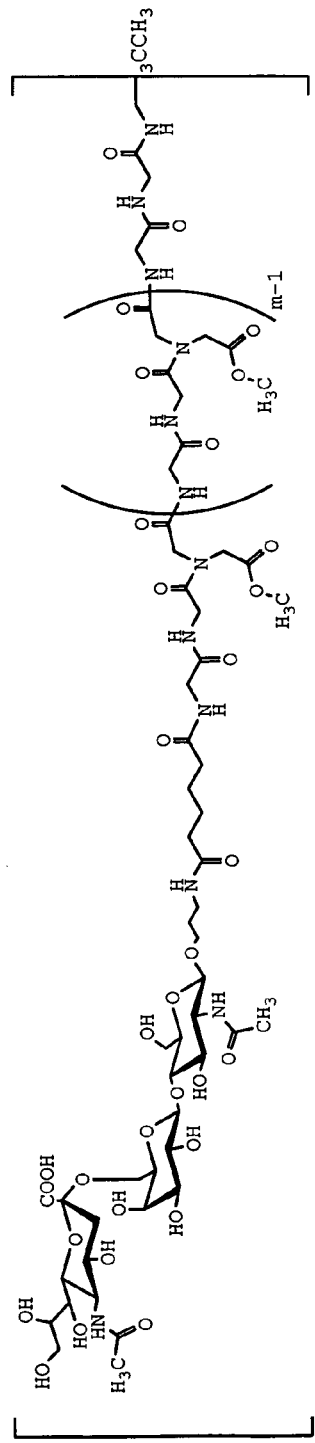
FIG. 1. Generic structure of the multiligand constructs designated {6'SLN-S$_1$-S$_2$-[Gly$_2$(MCMGly)]$_n$Gly$_2$-NHCH$_2$}$_3$CCH$_3$ (where S$_1$ is 1-aminopropyl and S$_2$ is —CO(CH$_2$)$_4$CO—).
Figure 2:
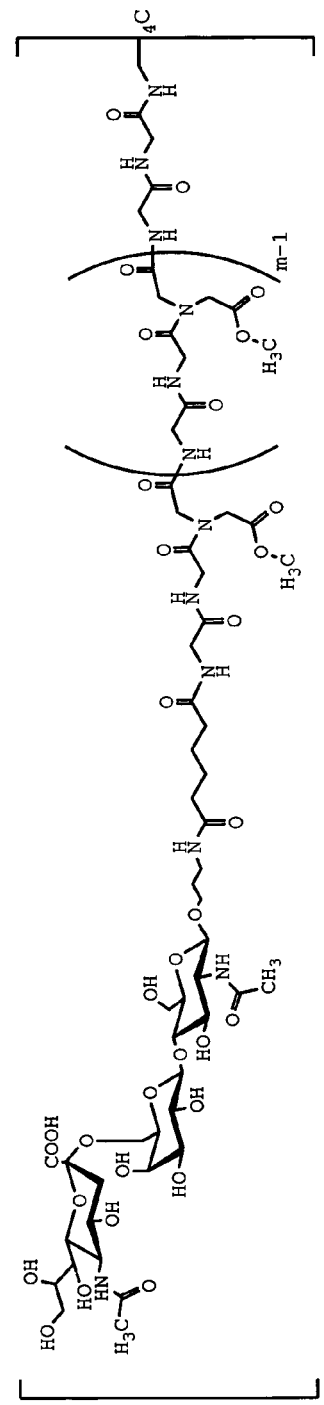
FIG. 2. Generic structure of the multiligand constructs designated {6'SLN-S$_1$-S$_2$-[Gly$_2$(MCMGly)]$_n$Gly$_2$-NHCH$_2$}$_4$C (where S$_1$ is 1-aminopropyl and S$_2$ is —CO(CH$_2$)$_4$CO—).
Figure 3:
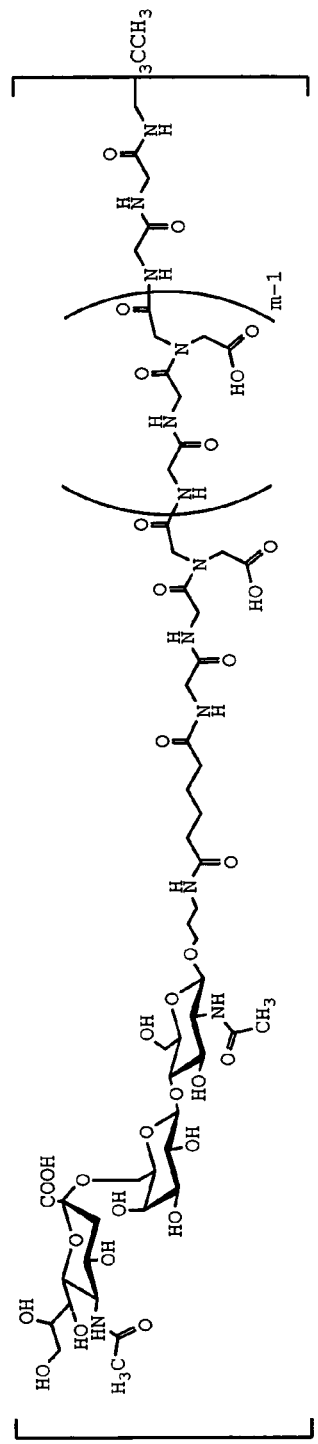
FIG. 3. Generic structure of the multiligand constructs designated {6'-SLN-S$_1$-S$_2$-[Gly$_2$(CMGly)]$_n$Gly$_2$-NHCH$_2$}$_3$CCH$_3$ (where S$_1$ is 1-aminopropyl and S$_2$ is —CO(CH$_2$)$_4$CO—).
Figure 4:
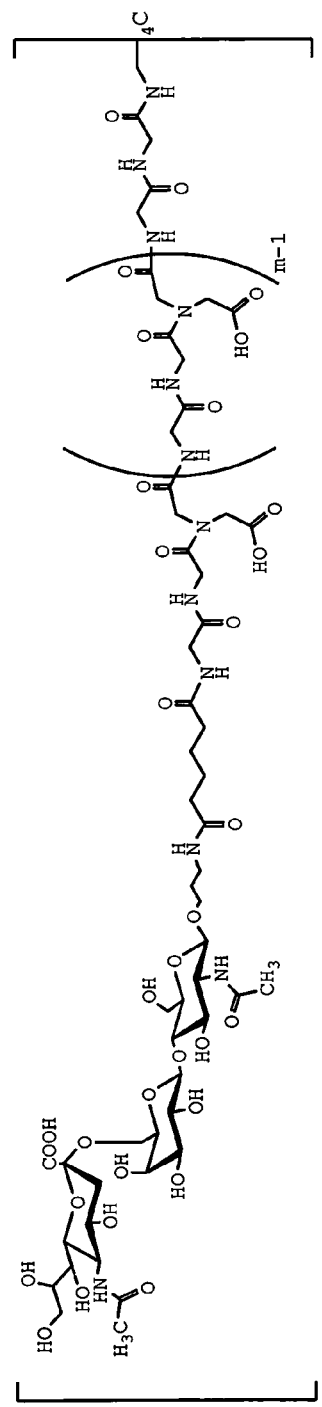
FIG. 4. Generic structure of the multiligand constructs designated {6'SLN-S$_1$-S$_2$-[Gly$_2$(CMGly)]$_n$Gly$_2$-NHCH$_2$}$_4$C (where S$_1$ is 1-aminopropyl and S$_2$ is —CO(CH$_2$)$_4$CO—).
Figure 5:
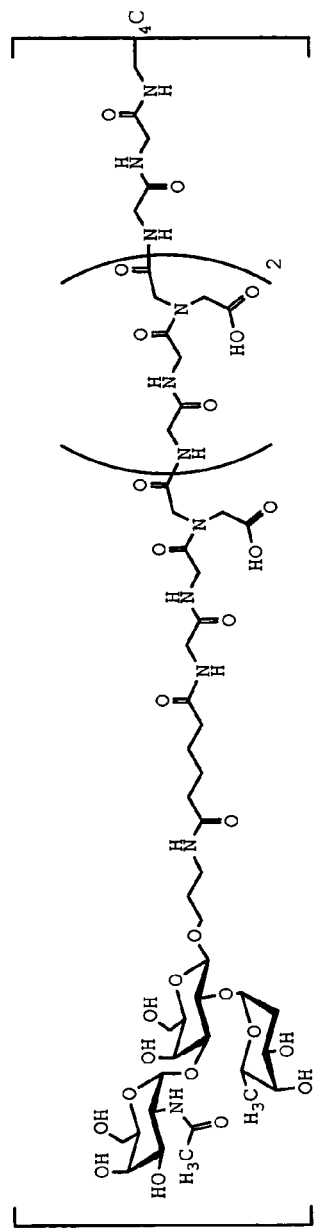
FIG. 5. Structure of the multiligand construct designated {A$_{tri}$-S$_1$-S$_2$-[Gly$_2$(CMGly)]$_3$Gly$_2$-NHCH$_2$}$_4$C (53A).
Figure 6:
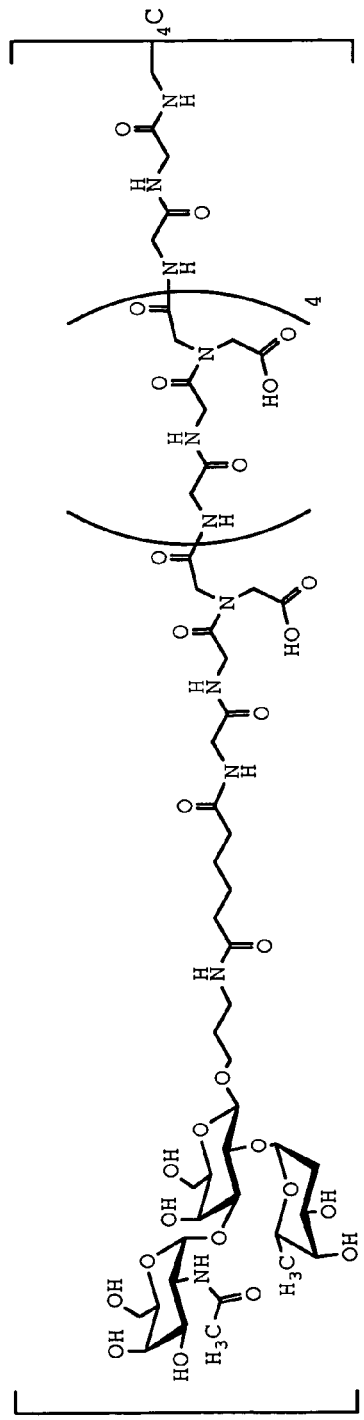
FIG. 6. Structure of the multiligand construct designated {A$_{tri}$-S$_1$-S$_2$-[Gly$_2$(CMGly)]$_5$Gly$_2$-NHCH$_2$}$_4$C (54A).
Figure 7:
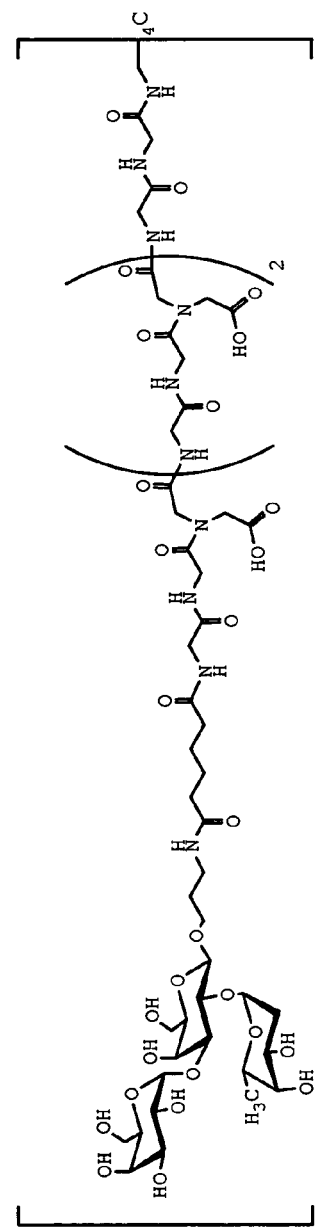
FIG. 7. Structure of the multiligand construct designated {B$_{tri}$-S$_1$-S$_2$-[Gly$_2$(CMGly)]$_3$Gly$_2$-NHCH$_2$}$_4$C (53B).
Figure 8:
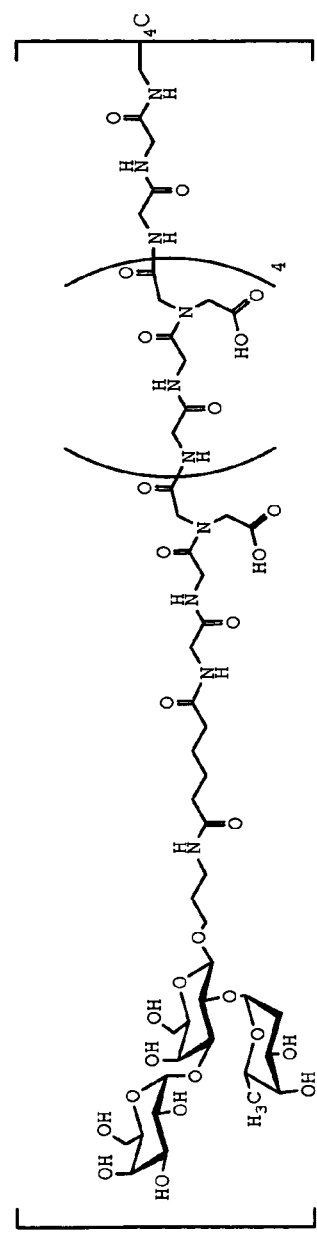
FIG. 8. Structure of the multiligand construct designated {B$_{tri}$-S$_1$-S$_2$-[Gly$_2$(CMGly)]$_5$Gly$_2$-NHCH$_2$}$_4$C (54B).
Figure 9:
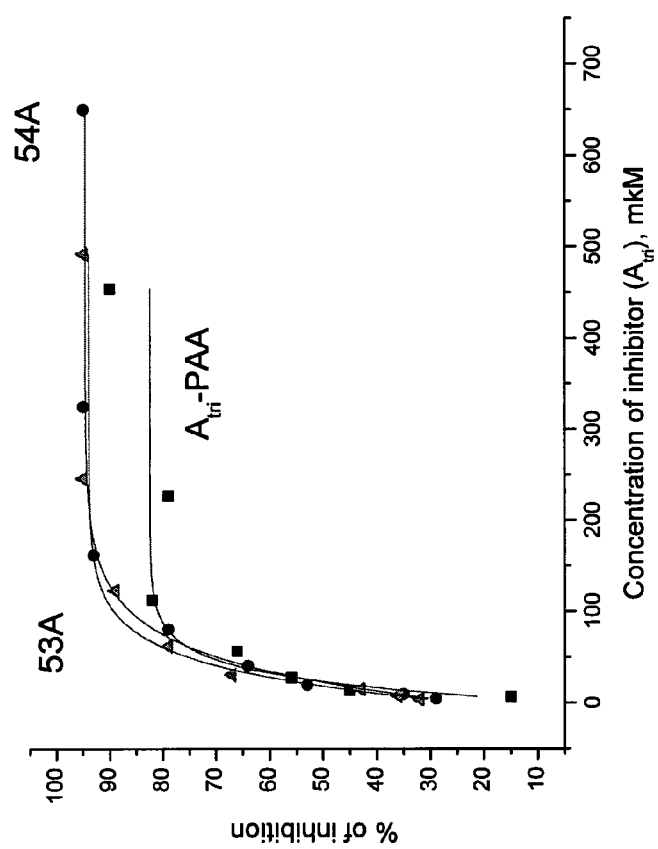
FIG. 9. Comparison of inhibition of mAbs A3 binding to A$_{tri}$-PAA-coated plates by A$_{tri}$-PAA, multiligand construct (53A), and multiligand construct (54A). Concentrations of 50% inhibition were 20 μM.
Figure 10:
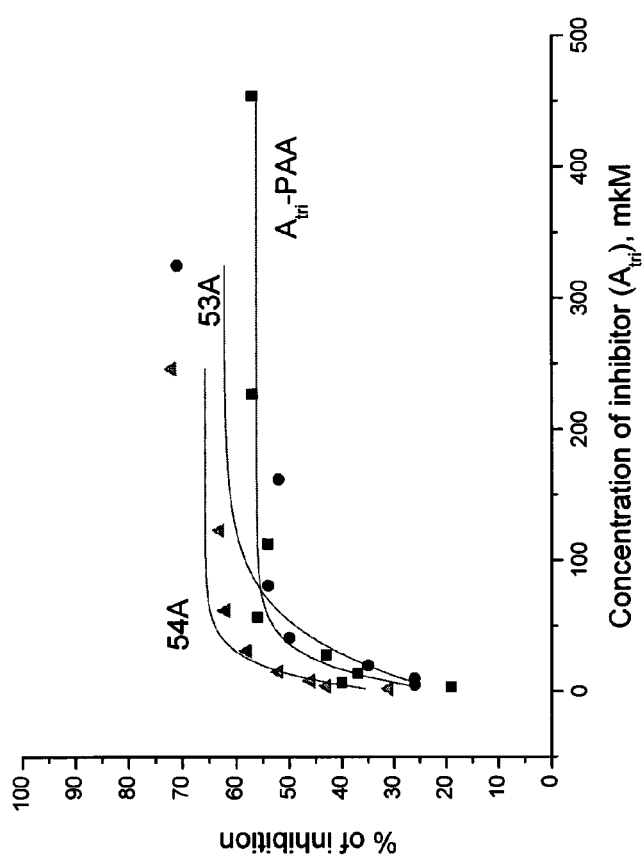
FIG. 10. Comparison of inhibition of anti-A antibodies (human blood serum, blood group III) binding to A$_{tri}$-PAA-coated plates by A$_{tri}$-PAA, multiligand construct (53A), and multiligand construct (54A). Concentration of 50% inhibition was 40 μM for A$_{tri}$-PAA and (53A), and 10 μM for (54A).
Figure 11:
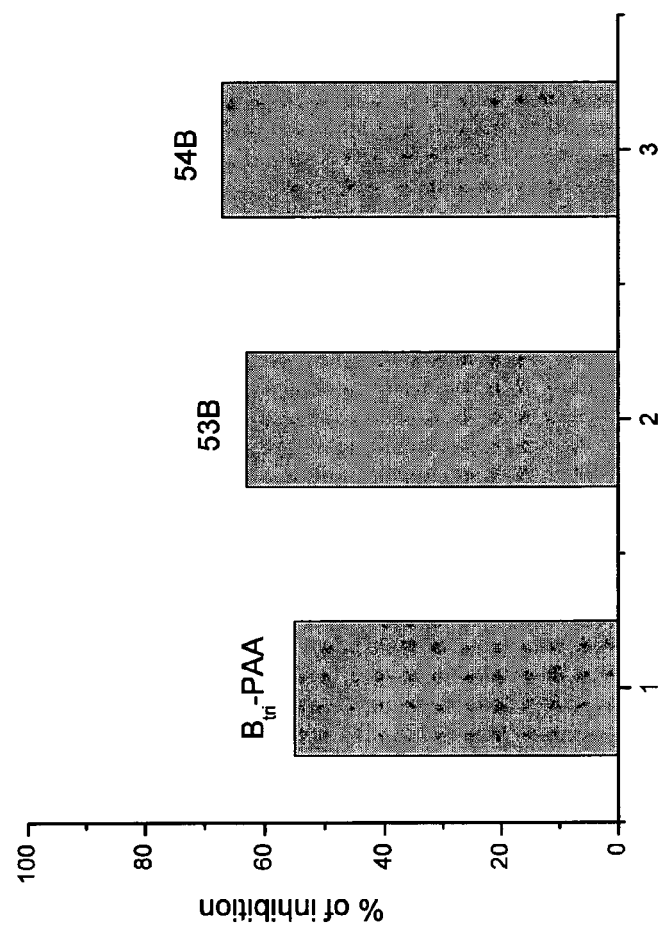
FIG. 11. Comparison of inhibition of mAbs B8 binding to B$_{tri}$-PAA-coated plates by B$_{tri}$-PAA, multiligand construct (53B), and multiligand construct (54B). All compounds at a concentration equivalent to 0.3 mM of trisaccharide (B$_{tri}$).

The multiligand constructs of the invention may be prepared in trivalent or tetravalent forms from the triamine (1) or tetraamine (2) base reagents, respectively, and via the intermediate multivalent constructs described below.

A number of derivatives of putative ligands (F-S$_1$-H, where F is the ligand) may be employed in the preparation of the multiligand constructs via the intermediate multivalent constructs. Examples of these derivatives are provided in Table 1.

Other putative ligands include: Galβ1-4GlcNAc; Galβ1-3GlcNAc; SAα2-6Galβ1-4Glc; SAα2-3Galβ1-4Glc; SAα2-6Galβ1-4GlcNAc; SAα2-3Galβ1-4GlcNAc; SAα2-3Galβ1-3GlcNAc; Galβ1-4(Fucα1-3)GlcNAc; Galβ1-3(Fucα1-3)GlcNAc; SAα2-3Galβ1-3(Fucα1-4)GlcNAc; SAα2-3Galβ1-4(Fucα1-3)GlcNAc; Galβ1-4GlcNAcβ1-4GlcNAc; Galβ1-3GlcNAcβ1-4GlcNAc; SAα2-6Galβ1-4GlcNAcβ1-4GlcNAc; SAα2-3Galβ1-4GlcNAcβ1-4GlcNAc; SAα2-3Galβ1-3GlcNAcβ1-4GlcNAc; Galβ1-4(Fucα1-3)GlcNAcβ1-4GlcNAc; Galβ1-3(Fucα1-4)GlcNAcβ1-4GlcNAc; SAα2-3Galβ1-3(Fucα1-4)GlcNAcβ1-4GlcNAc; SAα2-3Galβ1-4(Fucα1-3)GlcNAcβ1-4GlcNAc; SAα2-3Galβ1-3(Fucα1-4)GlcNAcβ1-4Gal; SAα2-3Galβ1-4(Fucα1-3)GlcNAcβ1-4Gal; SAα2-3Galβ1-4GlcNAcβ1-3Galβ1-4(Fucα1-3)GlcNAc; SAα2-6Galβ1-4GlcNAcβ1-3Galβ1-4(Fucα1-3)GlcNAc; SAα2-3Galβ1-4(Fucα1-3)GlcNAcβ1-3Galβ1-4Glc; SAα2-6Galβ1-4(Fucα1-3)GlcNAcβ1-3Galβ1-4Glc; SAα2-3Galβ1-4GlcNAcβ1-3Galβ1-4(Fucα1-3)GlcNAcβ1-3Galβ1-4Glc; SAα2-6Galβ1-4GlcNAcβ1-3Galβ1-4(Fucα1-3)GlcNAcβ1-3Galβ1-4Glc; SAα2-3Galβ1-4(Fucα1-3)GlcNAcβ1-3Galβ1-4(Fucα1-3)GlcNAcβ1-3Galβ1-4Glc; SAα2-6Galβ1-4(Fucα1-3)GlcNAcβ1-3Galβ1-4(Fucα1-3)GlcNAcβ1-3Galβ1-4Glc; SAα2-3Galβ1-4(Fucα1-3)GlcNAcβ1-3Galβ1-4(Fucα1-3)Glc; SAα2-6Galβ1-4(Fucα1-3)GlcNAcβ1-3Galβ1-4(Fucα1-3)Glc; SAα2-3Galβ1-4GlcNAcβ1-3Galβ1-4(Fucα1-3)GlcNAcβ1-3Galβ1-4(Fucα1-3)Glc; SAα2-6Galβ1-4GlcNAcβ1-3Galβ1-4(Fucα1-3)GlcNAcβ1-3Galβ1-4(Fucα1-3)Glc; SAα2-3Galβ1-4(Fucα1-3)GlcNAcβ1-3Galβ1-4(Fucα1-3)GlcNAcβ1-3Galβ1-4(Fucα1-3)Glc; SAα2-6Galβ1-4(Fucα1-3)GlcNAcβ1-3Galβ1-4(Fucα1-3)GlcNAcβ1-3Galβ1-4(Fucα1-3)Glc; SAα2-3Galβ1-3(Fucα1-4)GlcNAc; SAα2-6Galβ1-3(Fucα1-4(GlcNAc; SAα2-3Galβ1-3GlcNAcβ1-4Galβ1-4(Fucα1-3)GlcNAc; SAα2-6Galβ1-3GlcNAcβ1-4Galβ1-4(Fucα1-3)GlcNAc; SAα2-3Galβ1-3(Fucα1-4)GlcNAcβ1-3Galβ1-4(Fucα1-3)GlcNAc; SAα2-6Galβ1-3(Fucα1-4)GlcNAcβ1-3Galβ1-4(Fucα1-3)GlcNAc; SAα2-3Galβ1-3(Fucα1-4)GlcNAcβ1-3Galβ1-4Glc; SAα2-6Galβ1-3(Fucα1-4)GlcNAcβ1-3Galβ1-4Glc; SAα2-3Galβ1-3GlcNAcβ1-4Galβ1-4(Fucα1-3)GlcNAcβ1-3Galβ1-4Glc; SAα2-6Galβ1-3GlcNAcβ1-4Galβ1-4(Fucα1-3)GlcNAcβ1-3Galβ1-4Glc; SAα2-3Galβ1-3(Fucα1-4)GlcNAcβ1-3Galβ1-4(Fucα1-3)GlcNAcβ1-3Galβ1-4Glc; SAα2-6Galβ1-3(Fucα1-4)GlcNAcβ1-3Galβ1-4(Fucα1-3)GlcNAcβ1-3Galβ1-4Glc; SAα2-3Galβ1-3(Fucα1-4)GlcNAcβ1-3Galβ1-4(Fucα1-3)Glc; SAα2-6Galβ1-3(Fucα1-4)GlcNAcβ1-3Galβ1-4(Fucα1-3)Glc; SAα2-3Galβ1-3GlcNAcβ1-4Galβ1-4(Fucα1-3)GlcNAcβ1-3Galβ1-4(Fucα1-3)Glc; SAα2-6Galβ1-3GlcNAcβ1-4Galβ1-4(Fucα1-3)GlcNAcβ1-3Galβ1-4(Fucα1-3)Glc; SAα2-3Galβ1-3(Fucα1-4)GlcNAcβ1-3Galβ1-4(Fucα1-3)GlcNAcβ1-3Galβ1-4(Fucα1-3)Glc; SAα2-6Galβ1-3(Fucα1-4)GlcNAcβ1-3Galβ1-4(Fucα1-3)GlcNAcβ1-3Galβ1-4(Fucα1-3)Glc; SAα2-3Galβ1-4GlcNAcβ1-3Galβ1-3(Fucα1-4)GlcNAc; SAα2-6Galβ1-4GlcNAcβ1-3Galβ1-3(Fucα1-4)GlcNAc; SAα2-3Galβ1-4(Fucα1-3)GlcNAcβ1-3Galβ1-3(Fucα1-4)GlcNAc; SAα2-6Galβ1-4(Fucα1-3)GlcNAcβ1-3Galβ1-3(Fucα1-4)GlcNAc; SAα2-3Galβ1-4GlcNAcβ1-3Galβ1-3(Fucα1-4)GlcNAcβ1-3Galβ1-4Glc; SAα2-6Galβ1-4GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)GlcNAcβ1-3Galβ1-4Glc; SAα2-6Galβ1-4(Fucα1-3)GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)Glc; SAα2-6Galβ1-4(Fucα1-3)GlcNAcβ1-3Galβ1-3(Fucα1-4)Glc; SAα2-3Galβ1-4GlcNAcβ1-3Galβ1-3(Fucα1-4)GlcNAcβ1-3Galβ1-4(Fucα1-3)Glc; SAα2-6Galβ1-4GlcNAcβ1-3Galβ1-3(Fucα1-4)GlcNAcβ1-3Galβ1-4(Fucα1-3)Glc; SAα2-3Galβ1-4(Fucα1-3)GlcNAcβ1-3Galβ1-3(Fucα1-4)GlcNAcβ1-3Galβ1-4(Fucα1-3)Glc; and SAα2-6Galβ1-4(Fucα1-3)GlcNAcβ1-3Galβ1-3(Fucα1-4)GlcNAcβ1-3Galβ1-4(Fucα1-3)Glc, where SA is sialic acid The invention provides for the intra-construct ligand separation to be pre-determined. Accordingly, in addition to the specificity of binding being determined by the characteristics of the moiety selected to provide the ligand, the avidity of binding between the construct and the receptor expressing target may be optimized.

Reaction of the base reagent with the N-oxisuccinimide ester of Boc-protected glycylglycine (Boc-GlyGlyNos) (3) and subsequent deprotection of the glycylglycine substituted base (4 or 5) provides a triamine block (6) or tetraamine block (7) (Scheme IA or IB).

TABLE 1

Structure and designation of intermediates (F—$S_1$—H) .

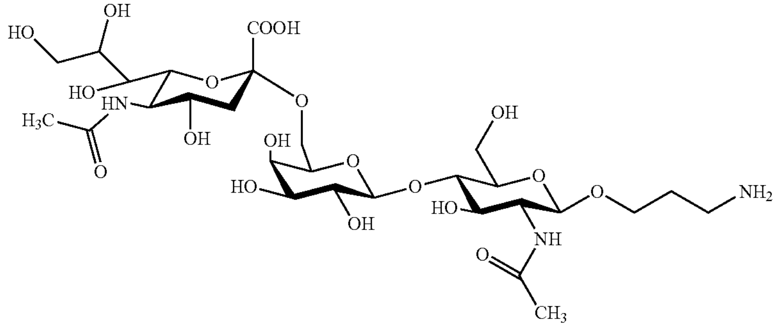

6′ SLN-$S_1$—H

TABLE 1-continued

Structure and designation of intermediates (F—$S_1$—H).

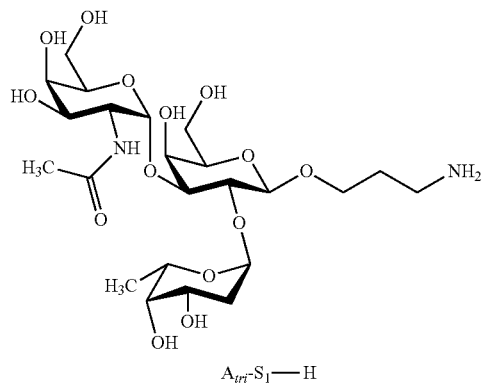

$A_{tri}$-$S_1$—H

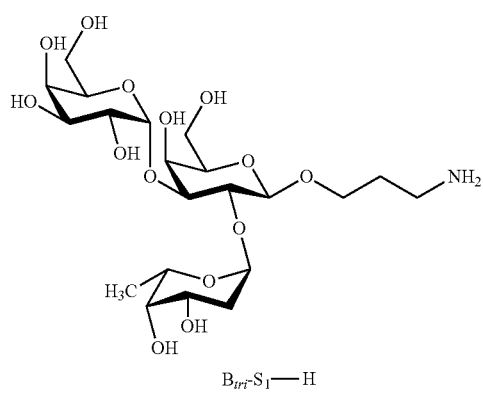

$B_{tri}$-$S_1$—H

6' SLN (Neu5Acα2-6Galβ1-4GlcNAcβ).
$A_{tri}$(GalNAcα1-3(Fucα1-2)Galβ).).
$B_{tri}$(Galα1-3(Fucα1-2)Galβ).

Reaction of iminodiacetic acid dimethyl ester (8) with the N-oxisuccinimide ester of Boc-protected glycylglycine (Boc-GlyGlyNos) (3) followed by partial hydrolysis of the dimethyl ester (9) and subsequent esterification of the acid (10) with N-oxisuccinimide provides the ester of Boc-protected diglycyl(methoxylcarbonylmethyl)glycine (11) (Scheme II).

Intermediates of the multiligand constructs in trivalent form are prepared by reacting the triamine block (6) prepared by the method of Scheme IA with the Boc-protected diglycyl (methoxylcarbonylmethyl)glycine N-oxisuccinimide ester (11) prepared by the method of Scheme II.

SCHEME IA

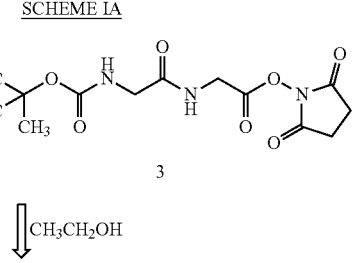

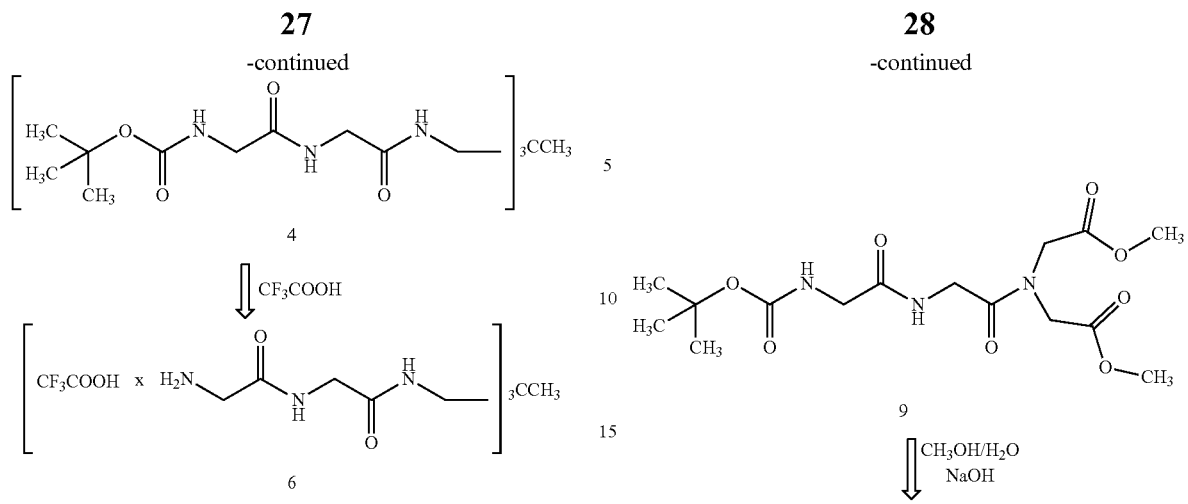
SCHEME IB
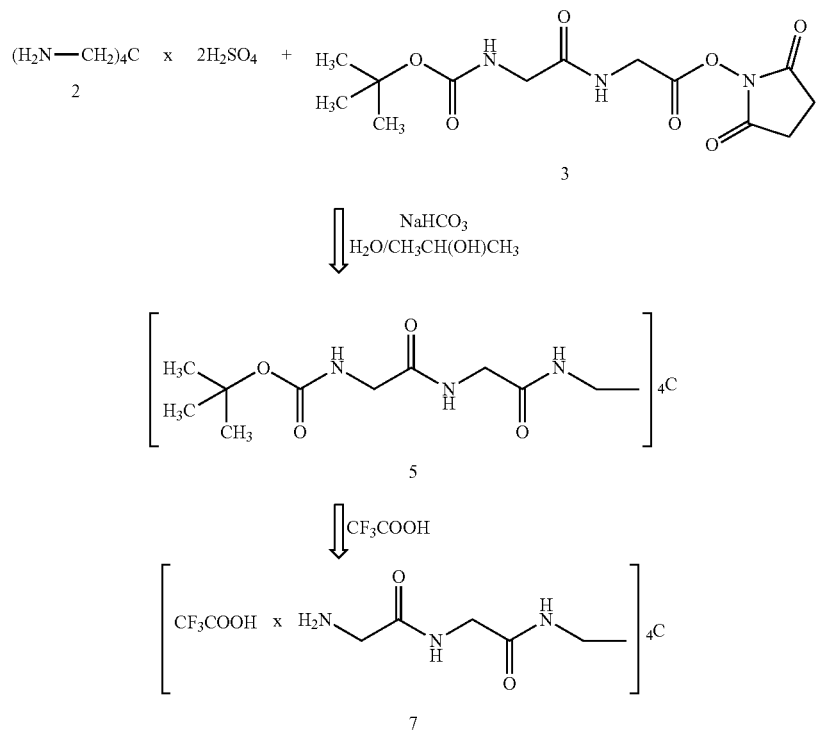
SCHEME II
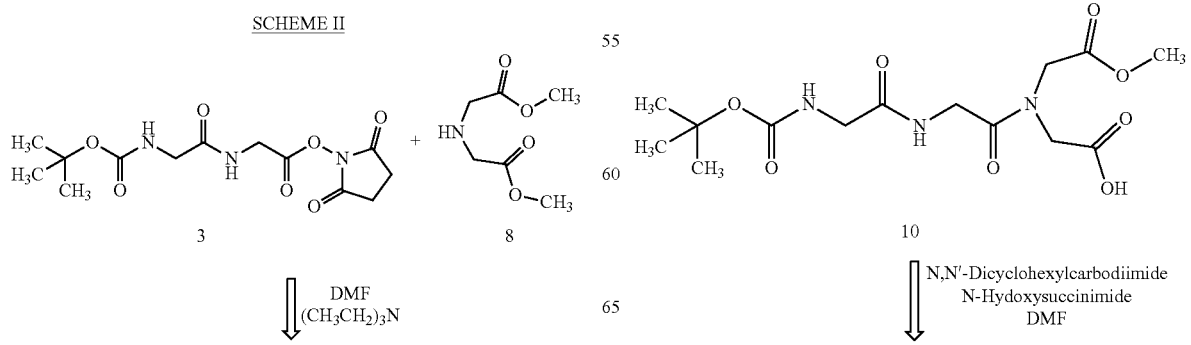

-continued
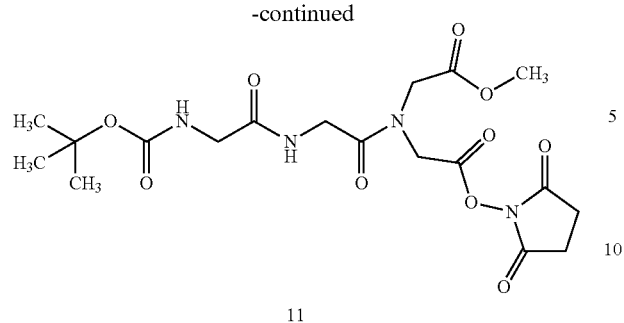
11
SCHEME IIIA
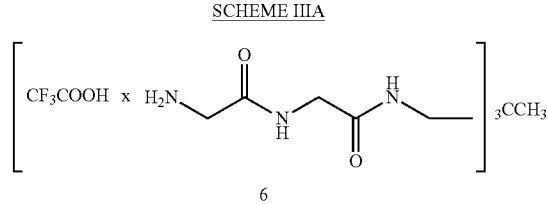
6
$$\Downarrow \begin{array}{c} DMSO \\ (CH_3CH_2)_3N \end{array} + $$ 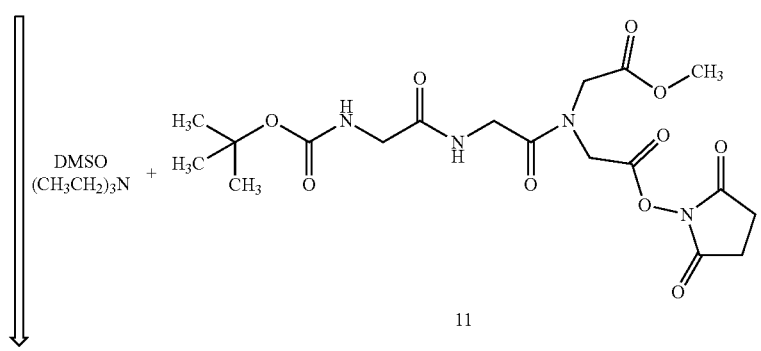
11
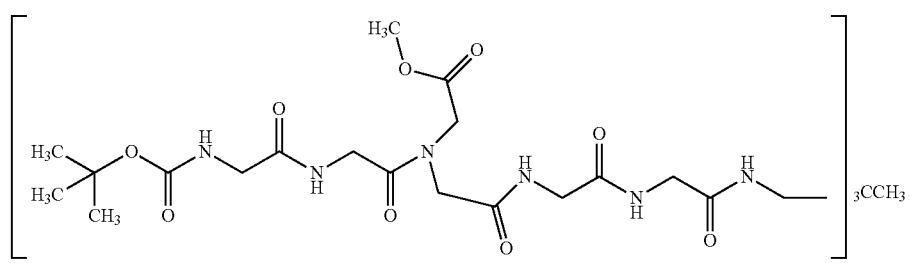
12
 $CF_3COOH$ -continued
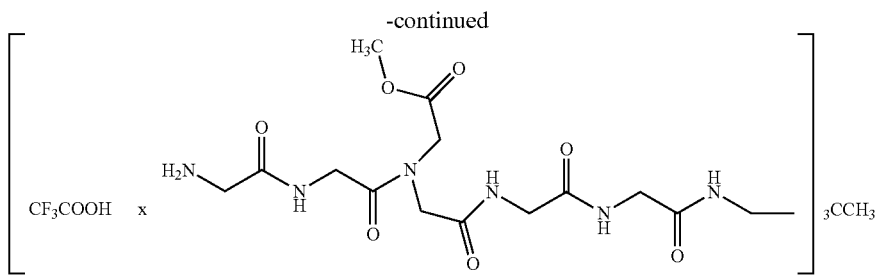
13
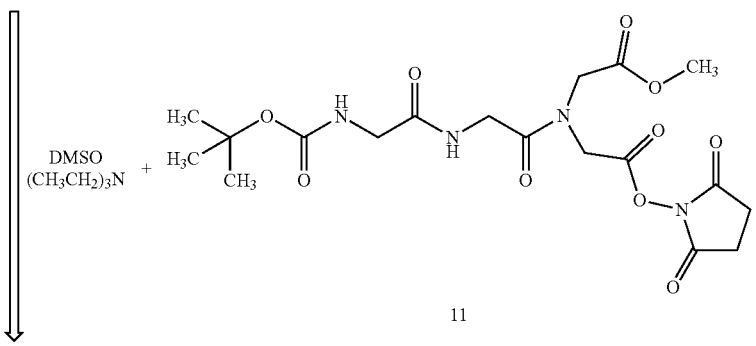
11
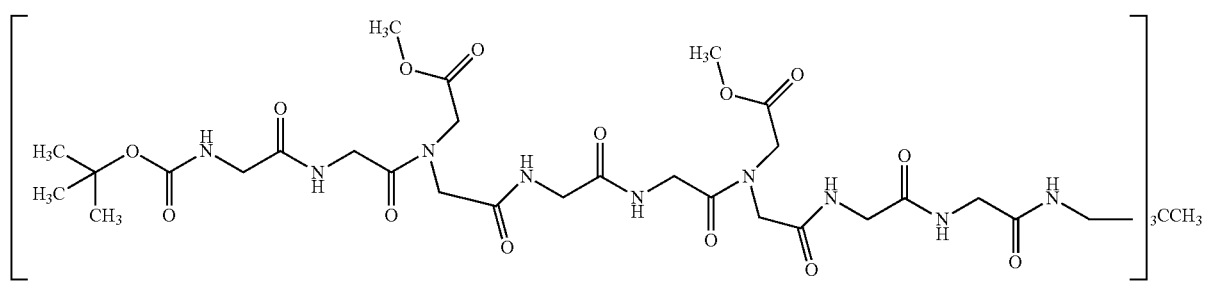
14
SCHEME IIIB
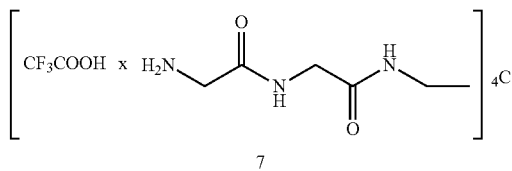
7
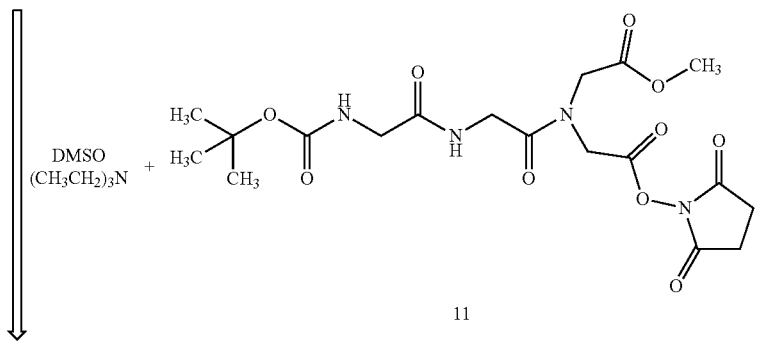
11

-continued

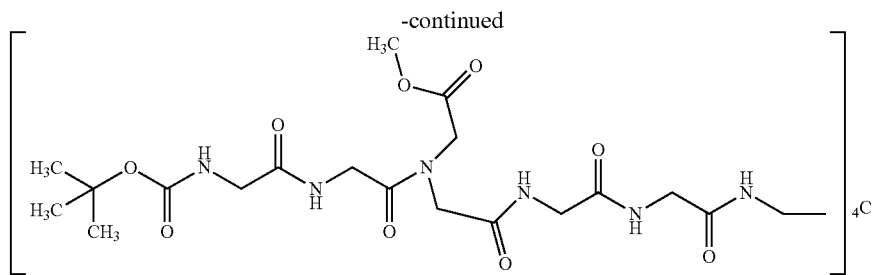

15

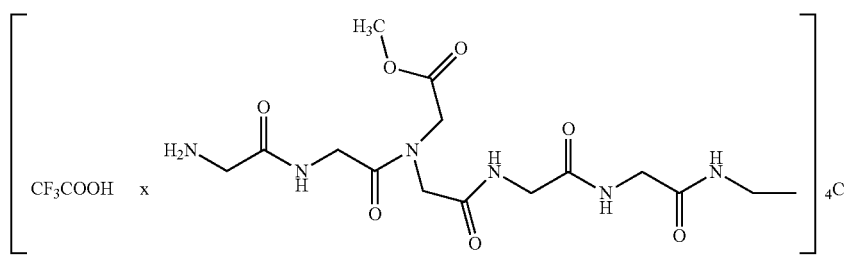

16

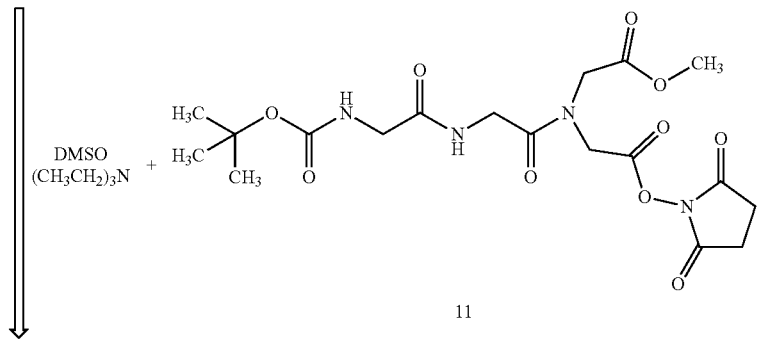

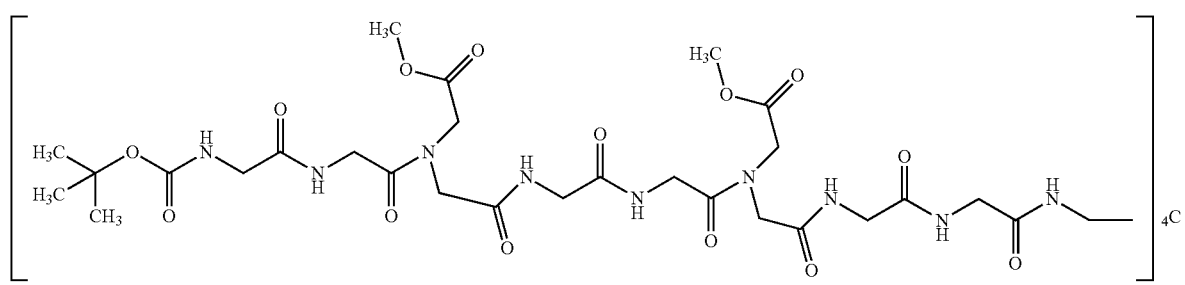

17

Intermediates of the multiligand constructs in tetravalent form are prepared by reacting the tetraamine block (7) prepared by the method of Scheme IB with the Boc-protected diglycyl(methoxylcarbonylmethyl)glycine N-oxisuccinimide ester (11) prepared by the method of Scheme II.

Multiligand constructs of either the trivalent or tetravalent form are prepared by consecutive elongation of the intermediates via their respective trifluoroacetic acid (CF₃COOH) salts.

The elongation steps provide elongated product of Formula I in high yield:

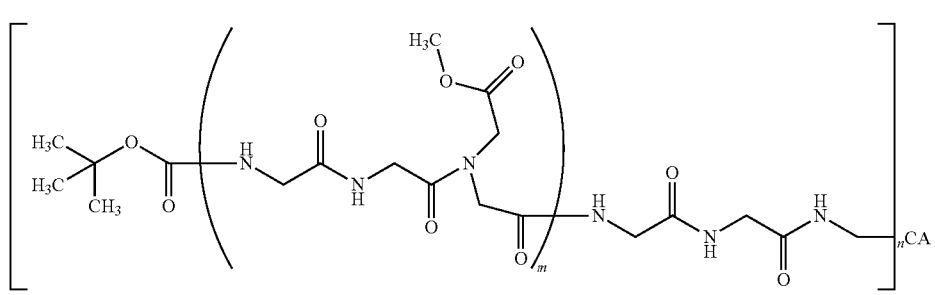

Formula I where:
m is the integer 1, 2, 3, 4 or 5; and
n is 3 and A is CH$_3$, or n is 4 and A is absent.

Deprotection of the terminal Boc-protected amino function of the product of Formula I provides the product of Formula II:

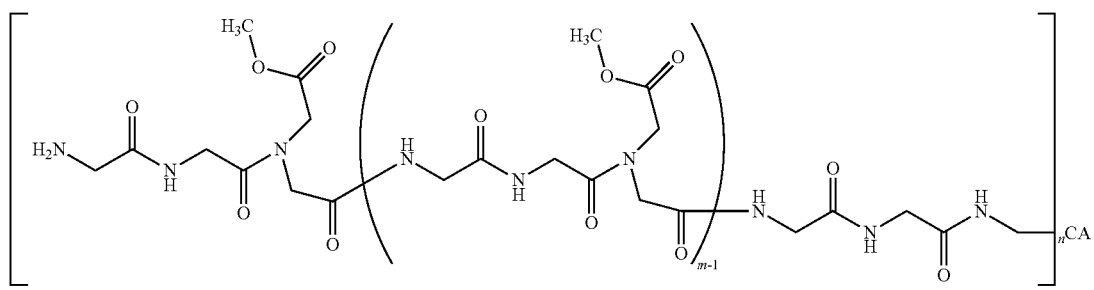

where:
m is the integer 1, 2, 3, 4 or 5; and
n is 3 and A is CH$_3$, or n is 4 and A is absent.

Although the products of Formula II are prepared in the Examples as CF$_3$COOH salts, it will be understood that other salts of the products of Formula II may be prepared. For convenience, in the representations of the structures of the products of Formula II, the acid of the salt has been omitted.

Multiligand constructs with a range of pre-determined ligand separations may therefore be prepared. The ligand separation of the construct is a function of the valency of the block (6,7) and the number of elongation steps (Scheme IIIA and IIIB) employed to provide the products of Formula I and Formula II.

Thus multiligand constructs prepared from the constructs identified in Tables 2 and 3 may be selected according to the intra-construct ligand separation required to provide optimal avidity or binding between the construct and the receptor expression target.

TABLE 2

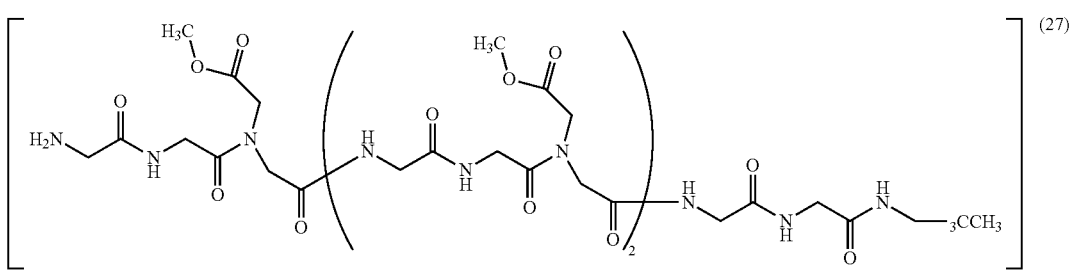

H-[Gly$_2$(MCMGly)]$_3$Gly$_2$-NHCH$_2$)$_3$CCH$_3$
m = 3

(27)

TABLE 2-continued
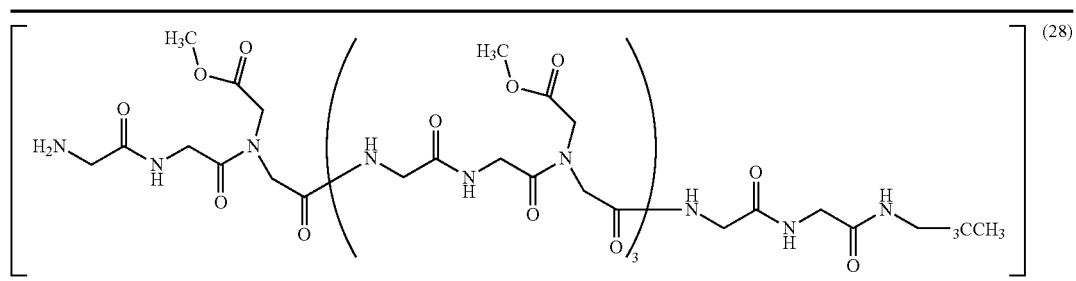
H-[Gly$_2$(MCMGly)]$_4$Gly$_2$-NHCH$_2$)$_3$CCH$_3$
m = 4
(28)
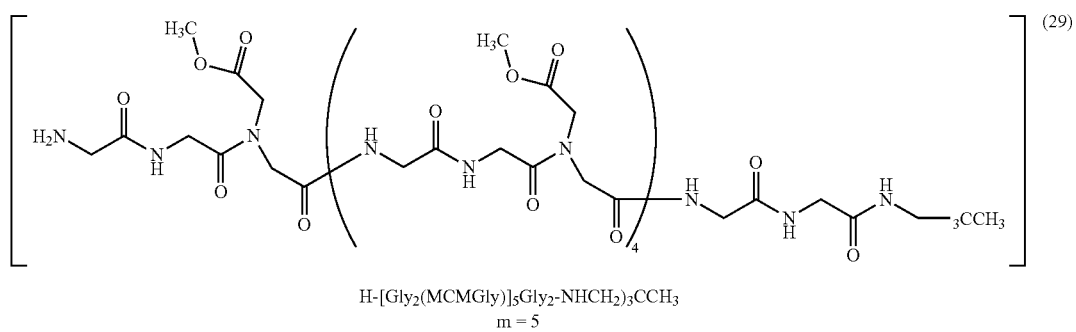
H-[Gly$_2$(MCMGly)]$_5$Gly$_2$-NHCH$_2$)$_3$CCH$_3$
m = 5
(29)
TABLE 3
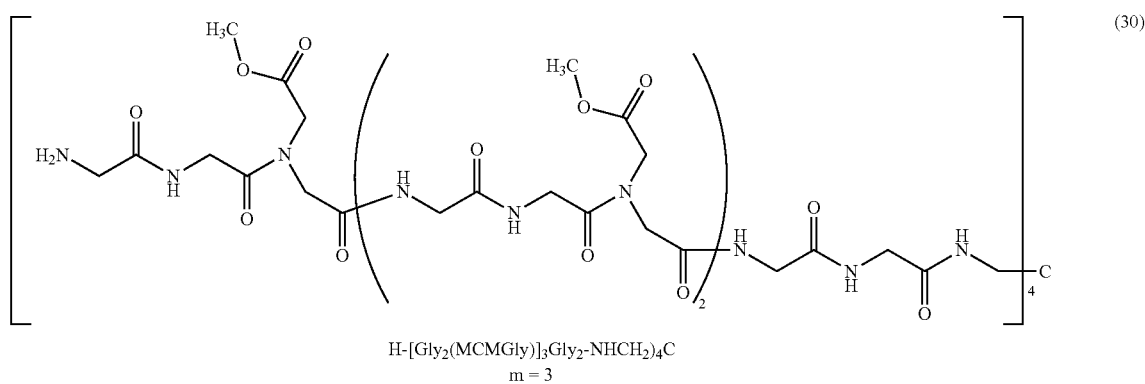
H-[Gly$_2$(MCMGly)]$_3$Gly$_2$-NHCH$_2$)$_4$C
m = 3
(30)
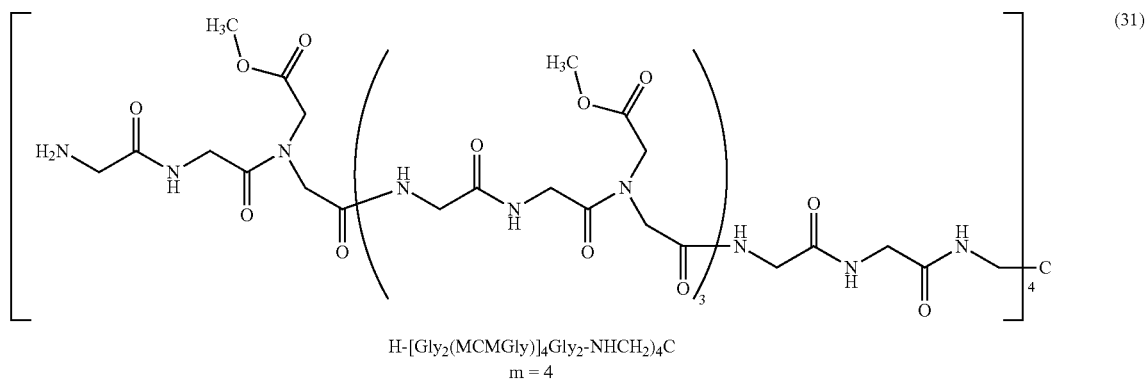
H-[Gly$_2$(MCMGly)]$_4$Gly$_2$-NHCH$_2$)$_4$C
m = 4
(31)

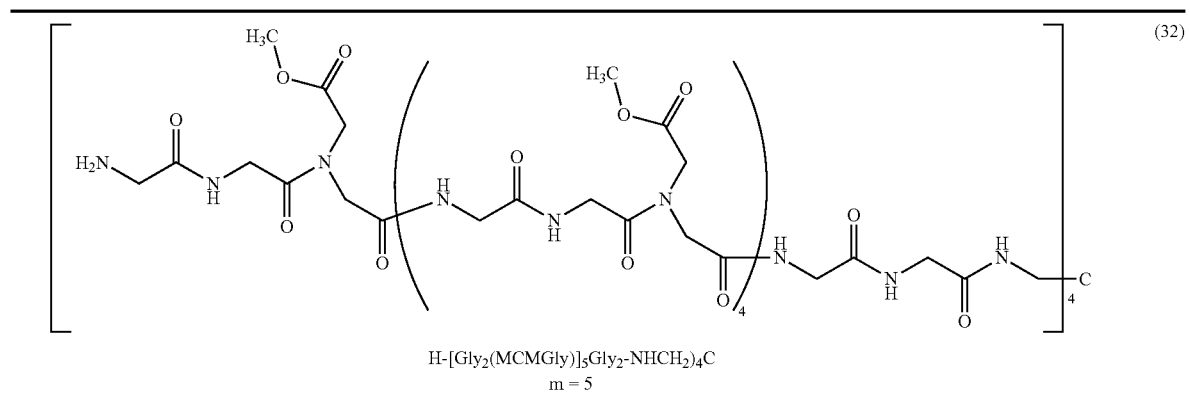

H-[Gly₂(MCMGly)]₅Gly₂-NHCH₂)₄C
m = 5

The products of Formula II are conjugated to a ligand (F) to provide the multiligand constructs. The conjugation may be mediated via the use of a spacer ($S_2$) moiety derived from a reagent such as adipic p-nitrophenyl diester (18).

For example, conjugation of the products of Formula II to the aminopropyl glycoside (19) of 6'SLN may be achieved via the intermediate 6'SLN-$S_1$-$S_2$-Nph (20) prepared according to Scheme IVα. Alternatively, conjugation of the products of Formula II to the aminopropyl glycoside (39A) of $A_{tri}$ may be achieved via the intermediate $A_{tri}$-$S_1$-$S_2$-Nph (40A) prepared according to Scheme IVβ. Conjugation of the products of Formula II to the aminopropyl glycoside (39B) of $B_{tri}$ may be achieved via the intermediate $B_{tri}$-$S_1$-$S_2$-Nph (40B) prepared according to Scheme IVγ.

The intermediate F-$S_1$-$S_2$-Nph (e.g. 6'SLN-$S_1$-$S_2$-Nph (20), $A_{tri}$-$S_1$-$S_2$-Nph (40A) or $B_{tri}$-$S_1$-$S_2$-Nph (40B)) is then conjugated to a trivalent (e.g. 21) or tetravalent (e.g. 22) product of Formula II to provide either a triligand construct (e.g. 23) or a tetra ligand construct (e.g. 24) according to Scheme VAα or VBα, respectively.

In addition to the specificity of binding of the multiligand constructs being determined by the characteristics of the moiety selected to provide the ligand, and the avidity of binding between the construct and the receptor expressing target being optimized by the intra-construct ligand separation, the properties of the multiligand constructs may be further optimised by alternatively conjugating the intermediate F-$S_1$-$S_2$-A (20) to a product of Formula II that has been demethylated.

SCHEME IVα

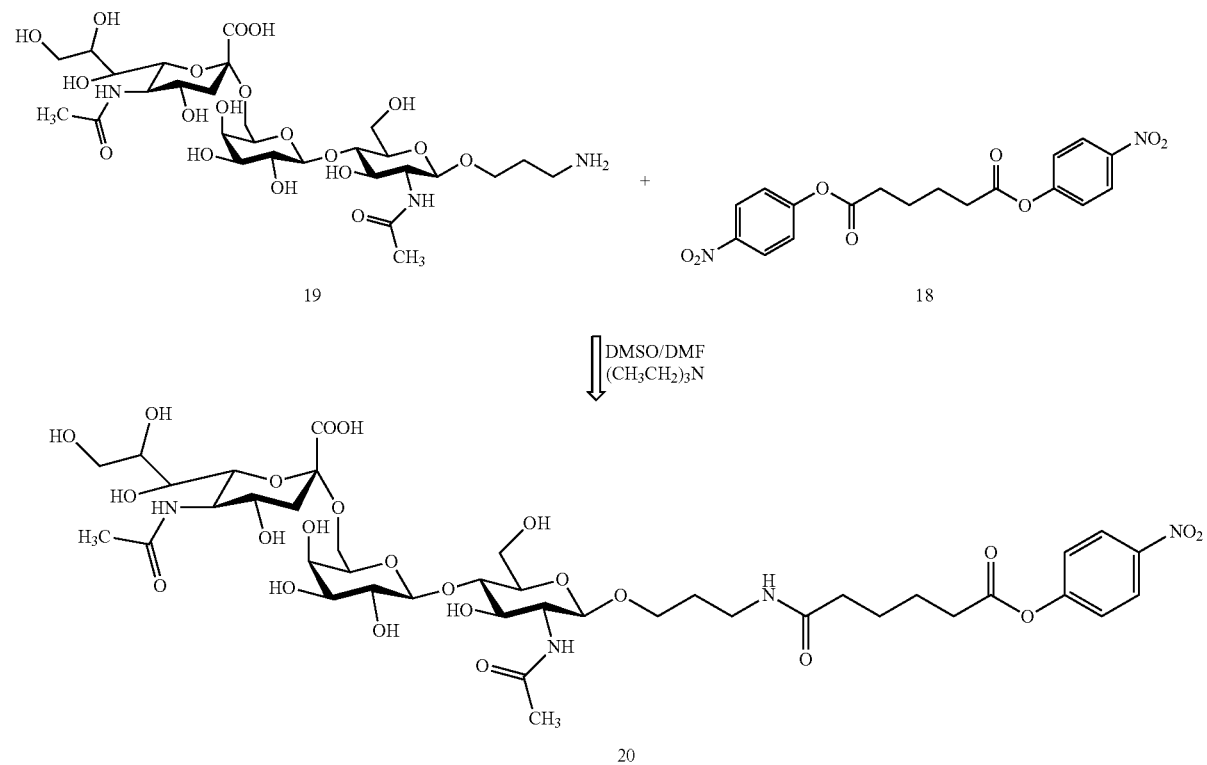

SCHEME IVβ
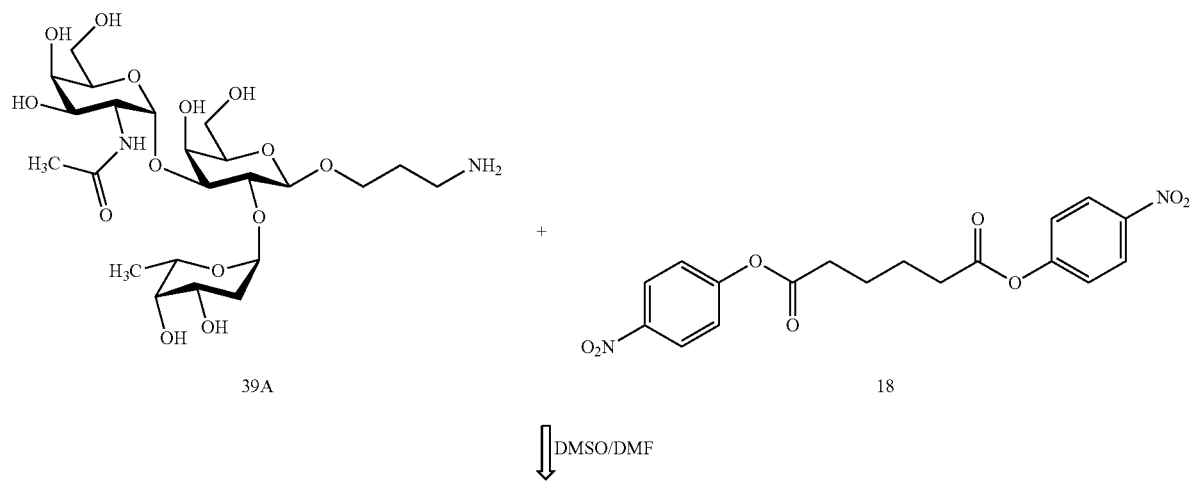
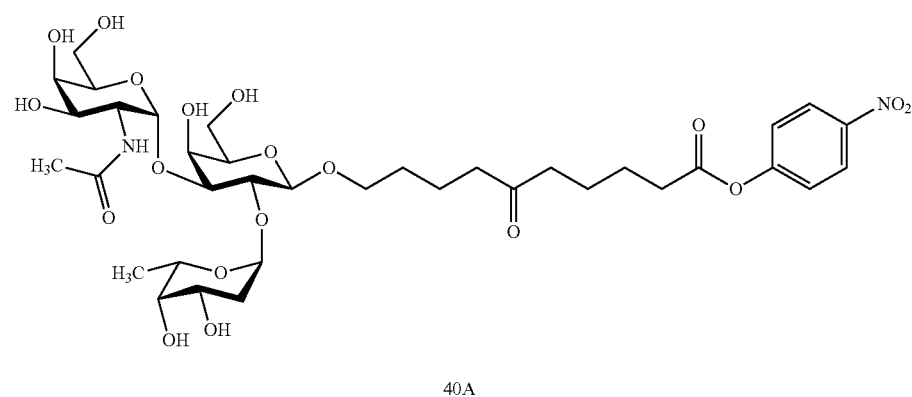
SCHEME IVγ
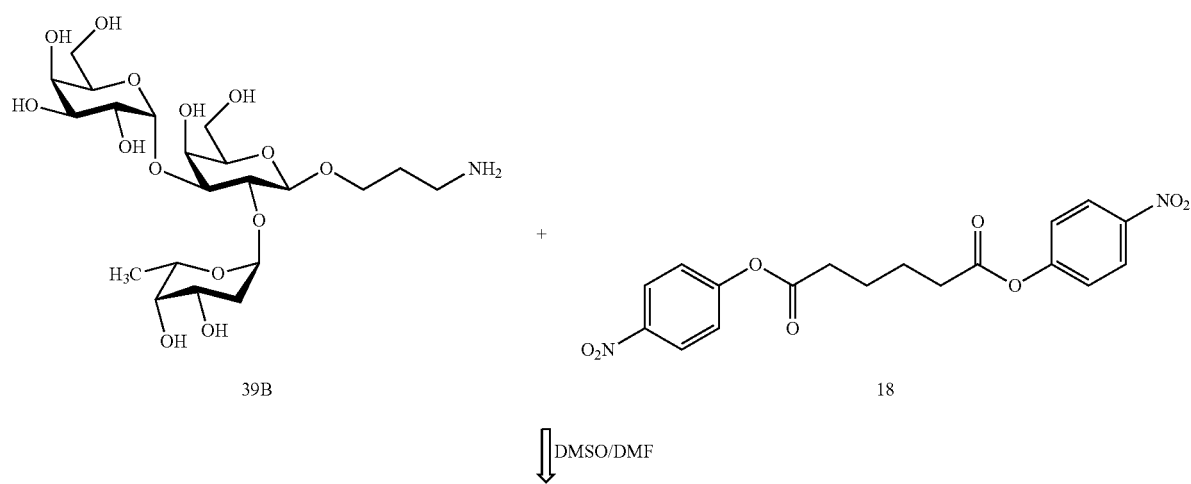

-continued

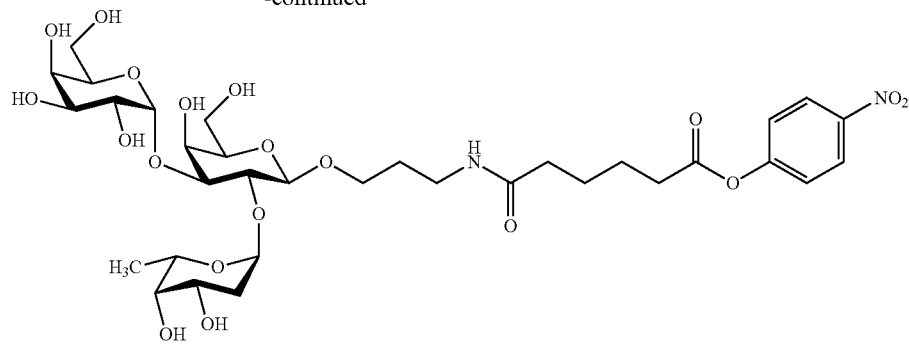

40B

For example, the intermediate 6'SLN-$S_1$-$S_2$-Nph (20) may be conjugated to trivalent (e.g. 21) or tetravalent (e.g. 22) products of Formula II with the inclusion of a demethylation step to provide either a triligand construct (e.g. 25) or a tetraligand construct (e.g. 26) according to either Scheme VIAα or VIBα, respectively.

Thus multiligand constructs prepared from the structures identified in Tables 4 and 5 may be selected according to the intra-construct ligand separation required to provide optimal avidity or binding between the multiligand construct and the receptor expressing target.

The differing properties of the methylated and demethylated multiligand constructs are anticipated to provide further advantages in respect of the bioavailability, pharmacokinetics and avidity of between the construct and the receptor expressing target when administering the multiligand constructs to a subject as a pharmaceutical preparation.

TABLE 4

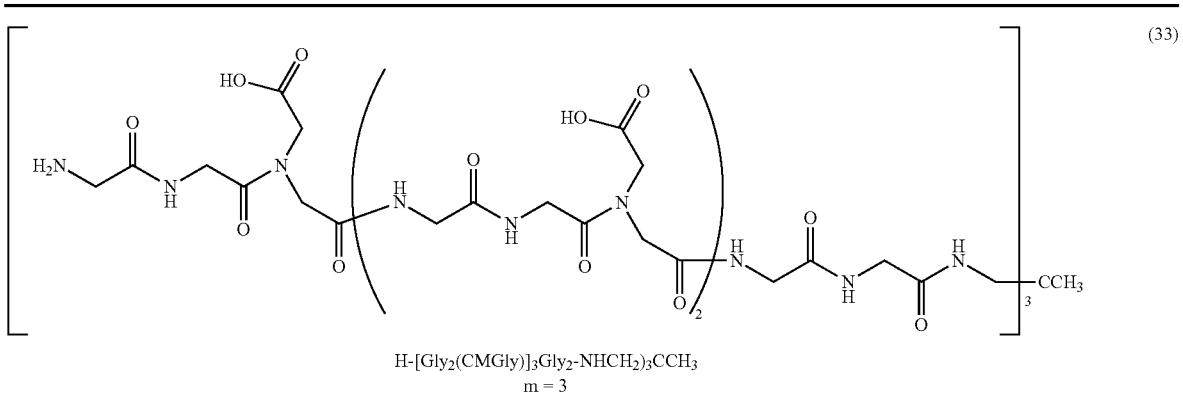

H-[Gly$_2$(CMGly)]$_3$Gly$_2$-NHCH$_2$)$_3$CCH$_3$
m = 3

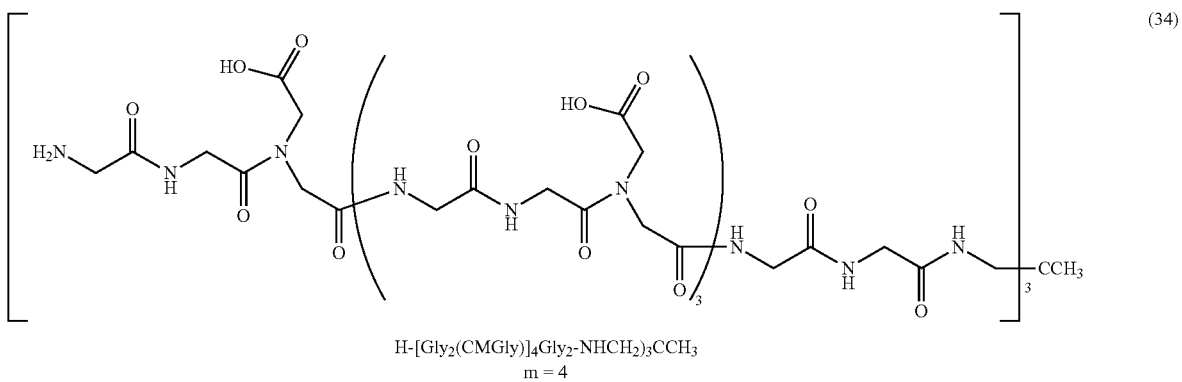

H-[Gly$_2$(CMGly)]$_4$Gly$_2$-NHCH$_2$)$_3$CCH$_3$
m = 4

TABLE 4-continued
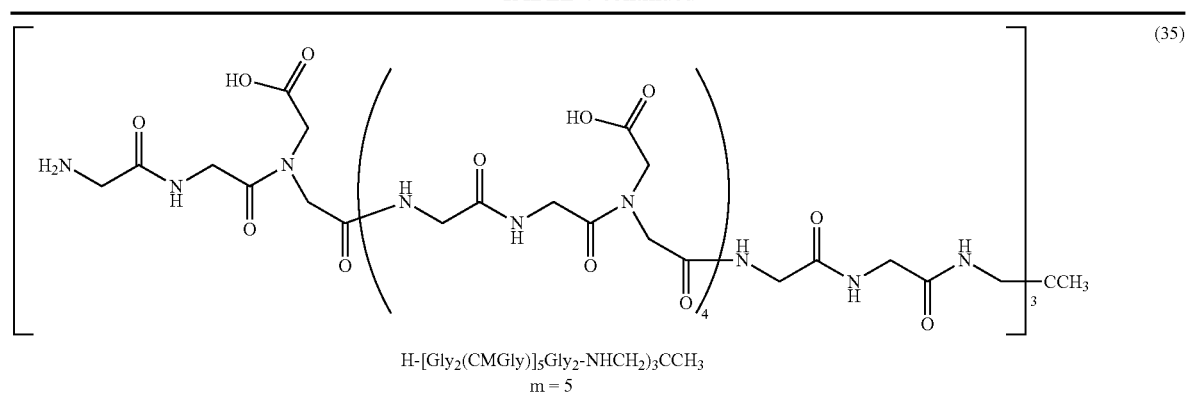
H-[Gly₂(CMGly)]₅Gly₂-NHCH₂)₃CCH₃
m = 5
TABLE 5
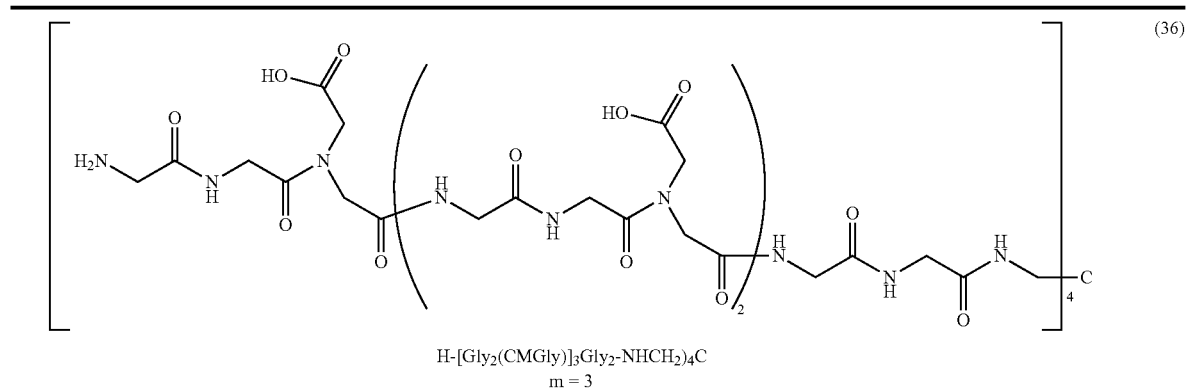
H-[Gly₂(CMGly)]₃Gly₂-NHCH₂)₄C
m = 3
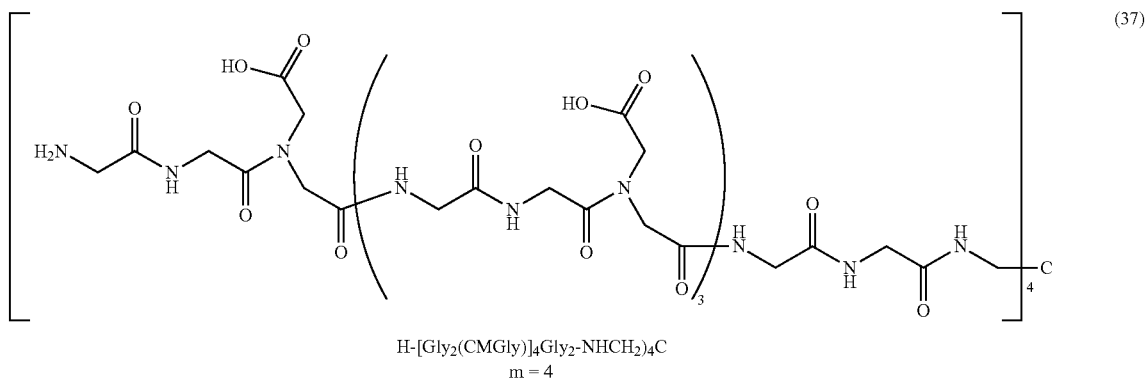
H-[Gly₂(CMGly)]₄Gly₂-NHCH₂)₄C
m = 4
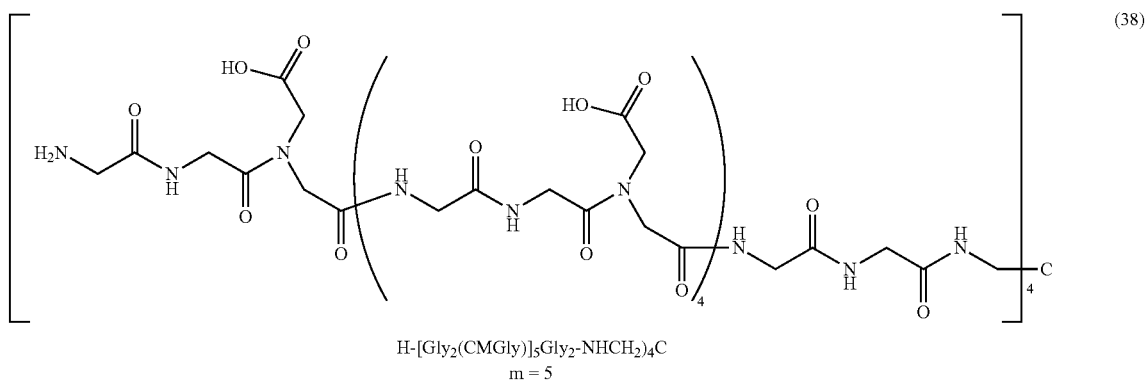
H-[Gly₂(CMGly)]₅Gly₂-NHCH₂)₄C
m = 5

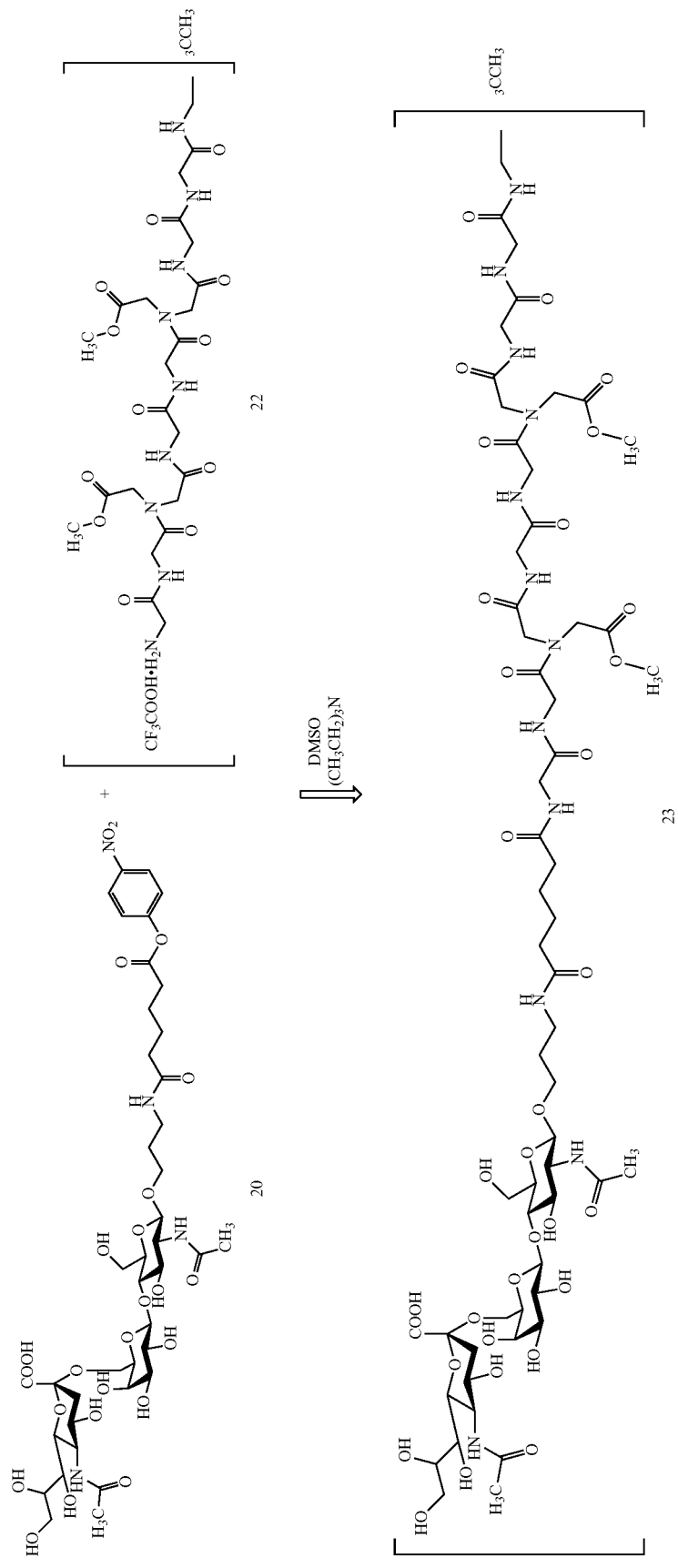

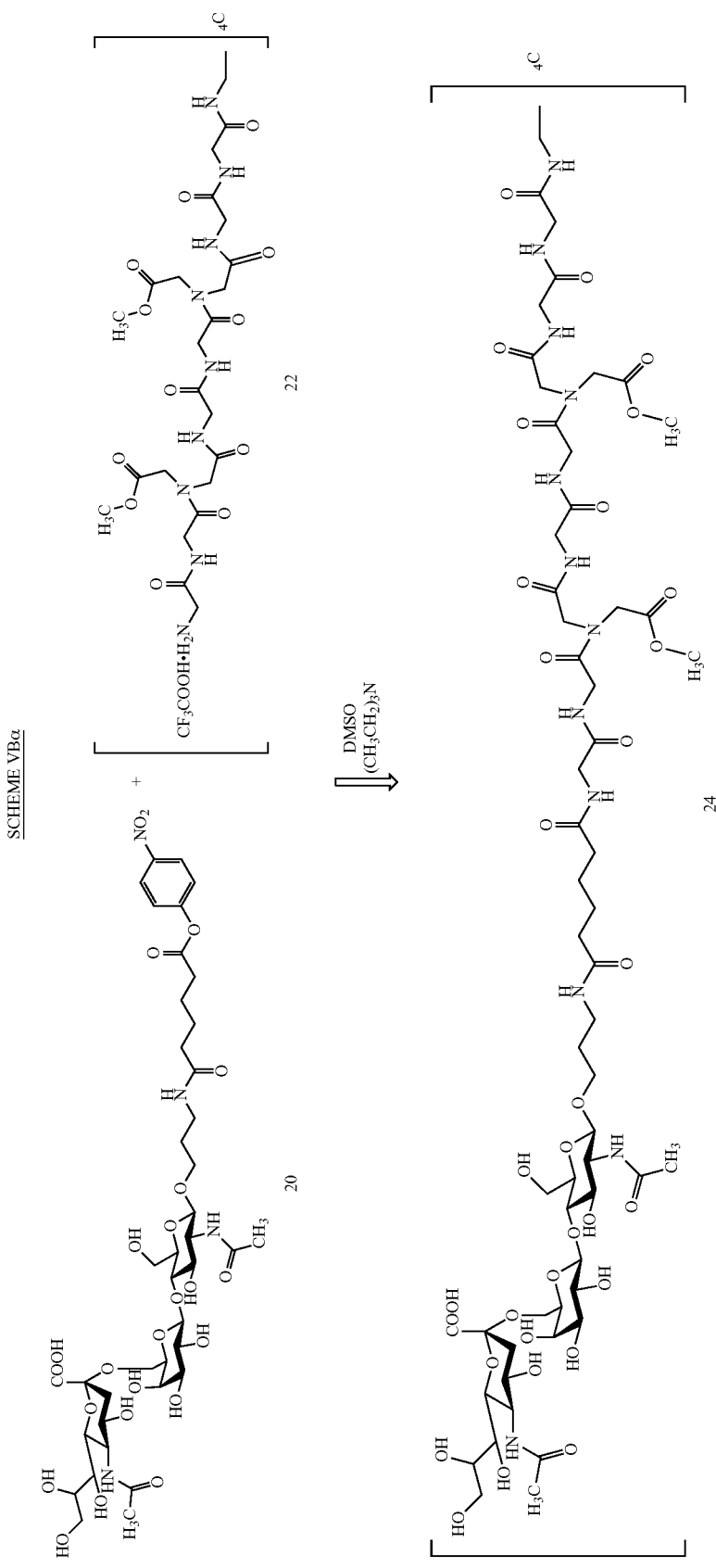

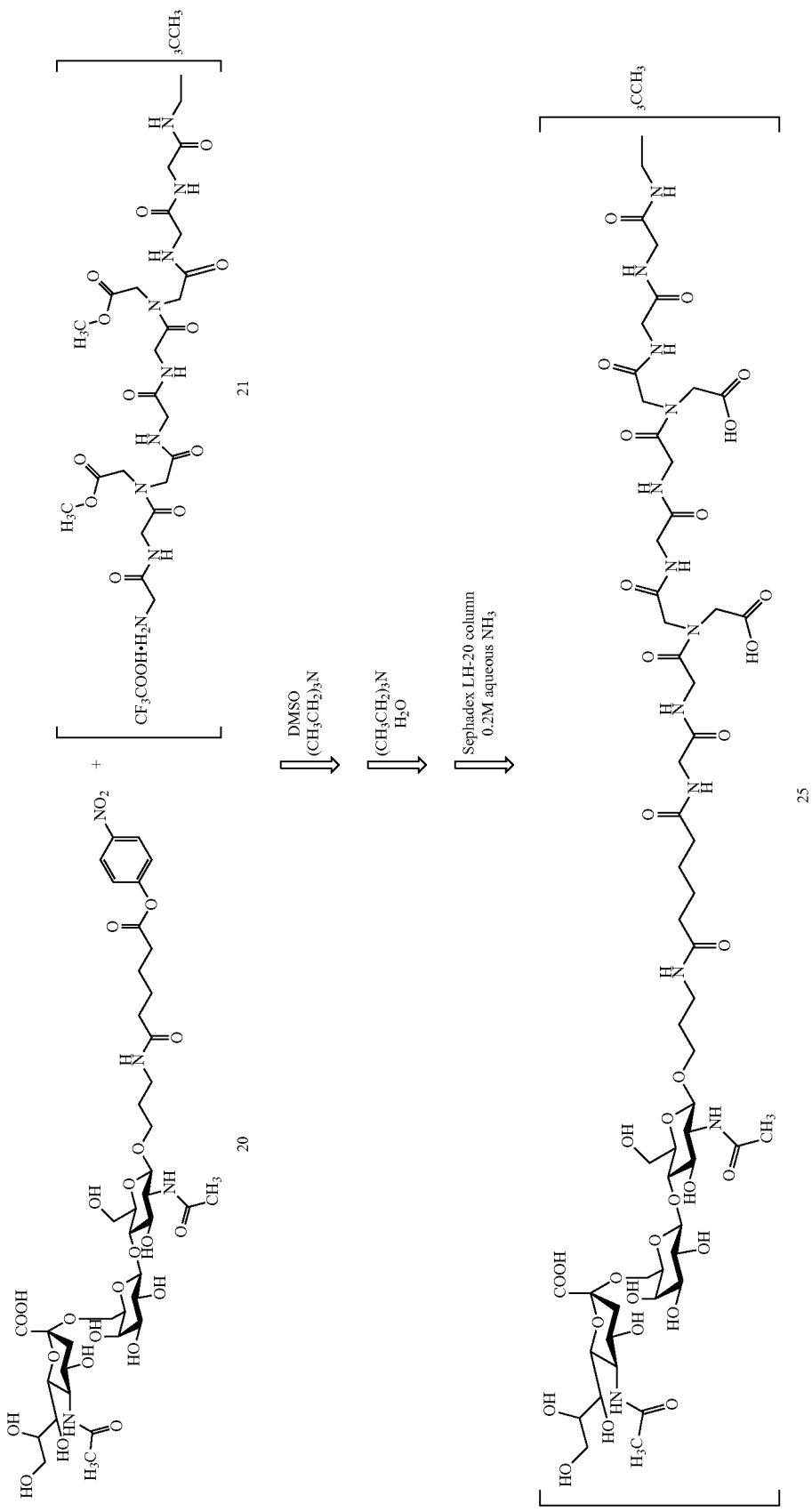

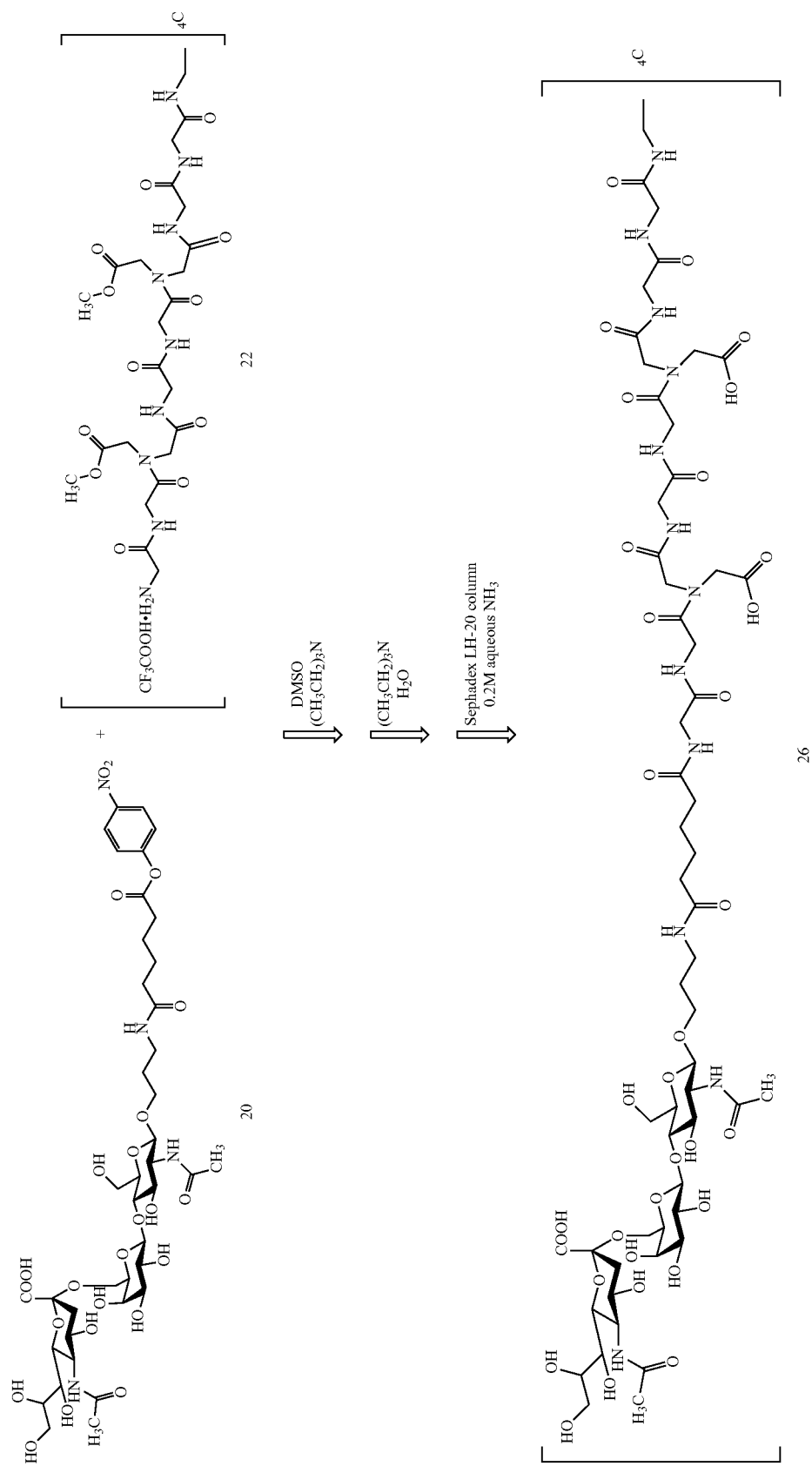

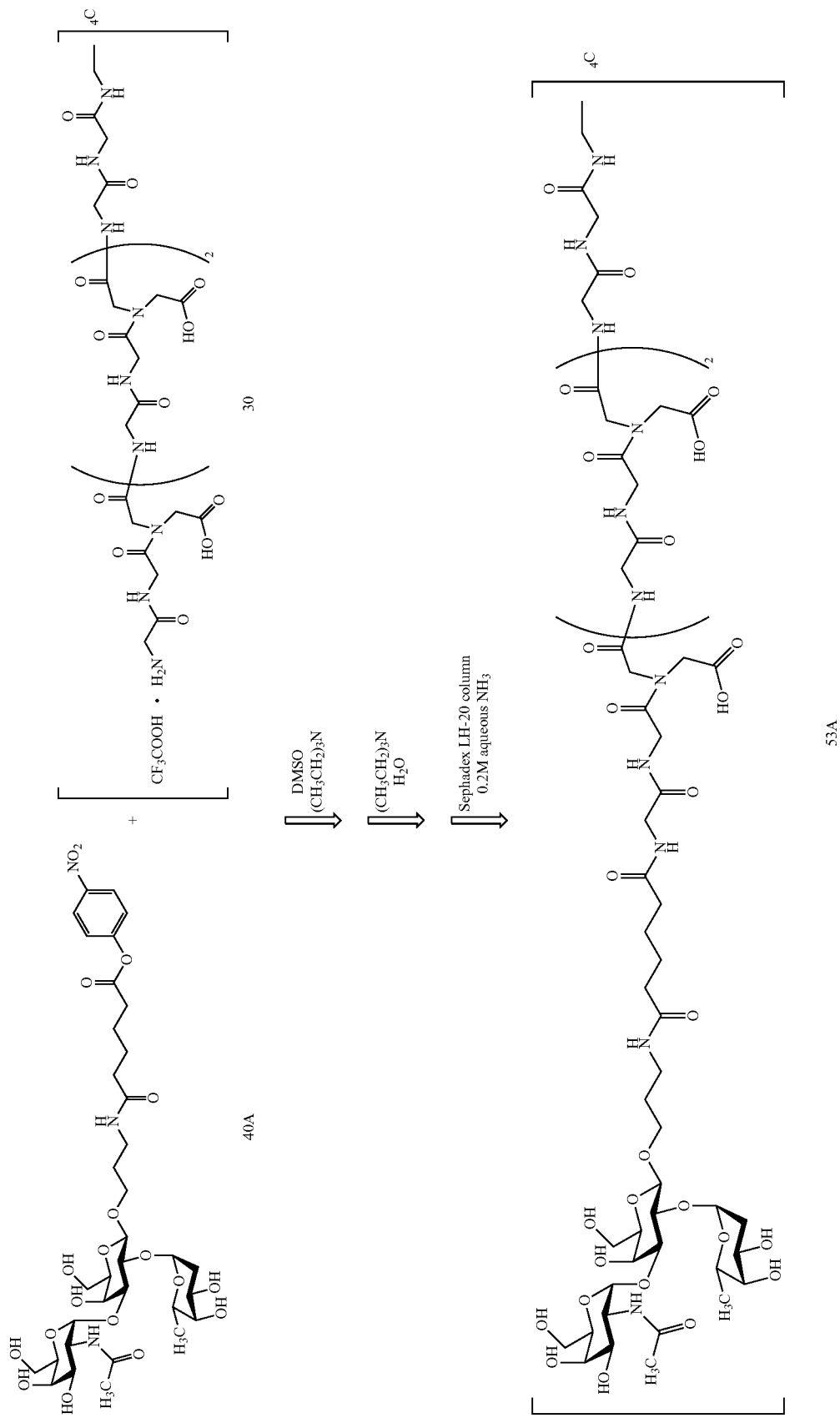

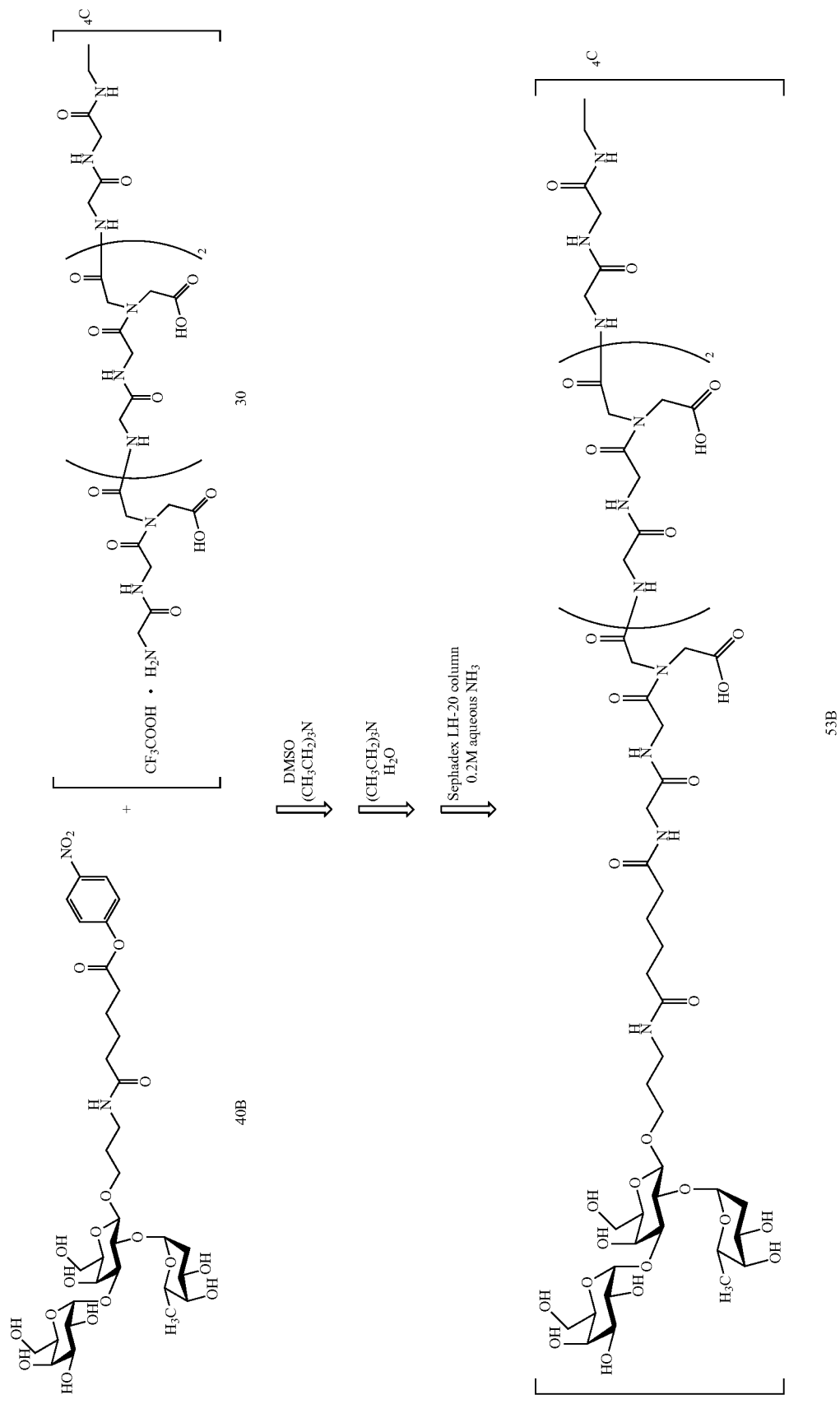

EXAMPLES

Materials and Methods

Acetone, benzene, chloroform, ethylacetate, methanol, toluene and o-xylene were from Chimmed (Russian Federation). Acetonitrile was from Cryochrom (Russian Federation). DMSO, DMF, $CF_3COOH$, $Et_3N$, N,N'-dicyclohexylcarbodiimide and N-hydroxysuccinimide were from Merck (Germany). Iminodiacetic acid dimethyl ester hydrochloride was from Reakhim (Russian Federation).

Dowex 50X4-400 and Sephadex LH-20 were from Amersham Biosciences AB (Sweden). Silica gel 60 was from Merck (Germany).

Triamine $(H_2N—CH_2)_3CCH_3$ was synthesized as described by Fleischer et al. (1971).

Tetraamine $(H_2N—CH_2)_4C \times 2H_2SO_4$ was synthesized as described by Litherland et al. (1938).

Glycoside Neu5Acα2-6Galβ1-4GlcNAcβ-O(CH$_2$)$_3$NH$_2$ was synthesized as described by Pazynina et al. (2002).

Trisaccharides GalNAcα1-3(Fucα1-2)Galβ-O(CH$_2$)$_3$NH$_2$ and Galα1-3(Fucα1-2)Galβ-O(CH$_2$)$_3$NH$_2$ were synthesized as described by Korchagina and Bovin (1992).

Thin-layer chromatography was performed using silica gel 60 $F_{254}$ aluminium sheets (Merck, 1.05554) with detection by charring after 7% $H_3PO_4$ soaking.

$^1$H NMR spectra were recorded at 30° C. with a Bruker WM 500 MHz instrument using the signal of the solvent's residual protons as reference ([$D_6$]DMSO, 2.500 ppm; [$D_2$]H$_2$O, 4.750 ppm).

ELISA for quantification of antibodies to blood group carbohydrate antigens was performed as described by Shilova et al. (2005).

Preparation of $(CF_3COOH.H$-Gly$_2$-HNCH$_2$)$_3$CCH$_3$ (6) (SCHEME 1A)

To the stirred solution of triamine $(H_2N—CH_2)_3CCH_3$ (1) (600 mg, 5.128 mmol) in ethanol (50 ml) Boc-GlyGlyNos (3) (5800 mg, 17.62 mmol) was added. The reaction mixture was stirred for 3 h, than stored at room temperature overnight.

The reaction mixture was filtered and the filtrate evaporated under reduced pressure. The residue was dried under vacuum and dissolved in ethyl acetate (125 ml).

The solution was washed with saturated aqueous NaCl (15 times 15 ml), water (3 times 5 ml), and dried with $Na_2SO_4$. The resulting solution was evaporated under reduced pressure and the residue was dried under vacuum.

The dried material (foam) was stored for 3 h with diethyl ether (40 ml) and then pulverized. The precipitate was filtered, washed with diethyl ether (3 times 10 ml) and dried under vacuum. Yield of (Boc-Gly$_2$-HNCH$_2$)$_3$CH$_3$ (4) was 3815 mg (98%), white solid.

$^1$H NMR (500 MHz, [$D_6$]DMSO, 30° C.) δ ppm: 8.212 (t, J=5.8 Hz, 3H; C—CH$_2$—NH), 7.850 (t, J=5.7 Hz, 3H; CH$_2$—NH), 6.910 (t, J=5.7 Hz, 3H; CH$_2$—NH-Boc), 3.697 (d, J=5.7 Hz, 6H; CH$_2$—NH), 3.631 (d, J=5.7 Hz, 6H; C H$_2$—NH), 2.835 (d, 6H; CCH$_2$), 1.382 (s, 27H; OC(CH$_3$)$_3$), 0.657 (s, 3H, CH$_3$) ppm.

The (Boc-Gly$_2$-HNCH$_2$)$_3$CH$_3$ (4) (1500 mg, 1.976 mmol) was dissolved in $CF_3COOH$ (5 ml) and the solution was kept for 2 h at room temperature. Trifluoroacetic acid was removed under vacuum and the residue was three times extracted with $Et_2O$ (slight agitation with 30 ml of $Et_2O$ for 30 min., followed by decantation) to eliminate residual $CF_3COOH$.

Solid residue was dissolved in 5 ml of water and freeze dried. Yield of $(CF_3COOH.H$-Gly$_2$-HNCH$_2$)$_3$CCH$_3$ (6) was 97%, white solid.

$^1$H NMR (500 MHz, [$D_2$]H$_2$O, 30° C.) δ, ppm: 3.934 (s, 6H, C(O)CH$_2$N), 3.870 (s, 6H, C(O)CH$_2$N), 2.972 (s, 6H, CCH$_2$), 0.739 (s, 3H, CH$_3$).

Preparation of $(CF_3COOH.H$-Gly$_2$-NHCH$_2$)$_4$C (7) (SCHEME IB)

To the stirred solution of tetraamine $(H_2N—CH_2)_4C \times 2H_2SO_4$ (2) (500 mg, 1.52 mmol) in the mixture of 1M aqueous NaHCO$_3$ (18.2 ml) and i-PrOH (9 ml) Boc-GlyGlyNos (3) (4012 mg, 12.18 mmol) was added ($CO_2$ evolution, foaming). The reaction mixture was stirred for 30 min, then 6 ml of 1M aqueous NaHCO$_3$ was added and the mixture stirred overnight.

Precipitate of (Boc-Gly$_2$-HNCH$_2$)$_4$C (5) was filtered, washed thoroughly with methanol/water mixture (1:1, 20 ml) and dried in vacuum. Yield 1470 mg (98%), white solid.

$^1$H NMR (500 MHz, [$D_6$]DMSO, 30° C.) δ, ppm: 8.491 (t, J=5.6 Hz, 1H; NHCO), 7.784 (t, J=6.6 Hz, 1H; C—CH$_2$—N HCO), 6.858 (t, J=6 Hz, 1H; NHCOO), 3.696 (d, J=5.6 Hz, 2H; COCH$_2$NH), 3.675 (d, J=6 Hz, 2H; COCH$_2$NHCOO), 2.685 (d, J=6.6 Hz, 2H; C—CH$_2$NH), 1.375 (s, 9H; C(CH$_3$)$_3$.

The (Boc-Gly$_2$-HNCH$_2$)$_4$C (5) (1450 mg, 1.466 mmol) was dissolved in $CF_3COOH$ (5 ml) and the solution was kept for 2 h at room temperature. Trifluoroacetic acid was removed under vacuum and the residue was three times extracted with $(CH_3CH_2)_2O$ (slight agitation with 30 ml of $(CH_3CH_2)_2O$ for 30 min., followed by decantation) to eliminate residual $CF_3COOH$.

Solid residue was dried under vacuum, dissolved in a minimum volume of water and passed through a Sephadex LH-20 column and eluted with water. Fractions, containing pure (7), were combined, evaporated to c. 5 ml and freeze dried. Yield 1424 mg (93%), white solid. TLC: $R_f$=0.5 (ethanol/conc. NH$_3$; 2:1 (v/v)).

$^1$H NMR (500 MHz, [$D_2$]H$_2$O, 30° C.) δ, ppm: 4.028 (s, 2H; COCH$_2$NH), 3.972 (s, 2H; COCH$_2$NH), 2.960 (s, 2H; C—CH$_2$NH).

Preparation of {[2-(2-tert-butoxycarbonylamino-acetylamino)-acetyl]-methoxycarbonylmethyl-amino}-acetic acid methyl ester (9) (SCHEME II)

To a stirred solution of (methoxycarbonylmethyl-amino)-acetic acid methyl ester hydrochloride (8) (988 mg, 5 mmol) in DMF (15 ml) were added Boc-GlyGlyNos (3) (3293 mg, 10 mmol) and $(CH_3CH_2)_3N$ (3475 µL, 25 mmol) were added. The mixture was stirred overnight at room temperature and then diluted with o-xylene (70 ml) and evaporated.

Flash column chromatography on silica gel (packed in toluene, and eluted with ethyl acetate) resulted in a crude product.

The crude product was dissolved in chloroform and washed sequentially with water, 0.5 M NaHCO$_3$ and saturated KCl.

The chloroform extract was evaporated and the product purified on a silica gel column (packed in chloroform and eluted with 15:1 (v/v) chloroform/methanol). Evaporation of the fractions and drying under vacuum of the residue provided a colourless thick syrup of (9). Yield 1785 mg, (95%). TLC: $R_f$=0.49 (7:1 (v/v) chloroform/methanol).

$^1$H NMR (500 MHz, [$D_6$]DMSO, 30° C.) δ, ppm: 7.826 (t, J=5.1 Hz, 1H; NHCO), 6.979 (t, J=5.9 Hz, 1H; NHCOO), 4.348 and 4.095 (s, 2H; NCH$_2$COO), 3.969 (d, J=5.1 Hz, 2H;

COC$\underline{H}_2$NH), 3.689 and 3.621 (s, 3H; OC$\underline{H}_3$), 3.559 (d, J=5.9 Hz, 2H; COC$\underline{H}_2$NHCOO). 1.380 (s, 9H; C(CH$_3$)$_3$).

Preparation of {[2-(2-tert-butoxycarbonylamino-acetylamino)-acetyl]-methoxycarbonylmethylamino}-acetic acid (10) (SCHEME II)

To a stirred solution of (9) (1760 mg, 4.69 mmol) in methanol (25 ml) 0.2 M aqueous NaOH (23.5 ml) was added and the solution kept for 5 min at room temperature. The solution was then acidified with acetic acid (0.6 ml) and evaporated to dryness.

Column chromatography of the residue on silica gel (packed in ethyl acetate and eluted with 2:3:1 (v/v/v) i-PrOH/ethyl acetate/water) resulted in a recovered (9) (63 mg, 3.4%) and target compound (10) (1320 mg). The intermediate product was then dissolved in methanol/water/pyridine mixture (20:10:1, 30 ml) and passed through an ion exchange column (Dowex 50X4-400, pyridine form, 5 ml) to remove residual sodium cations.

The column was then washed with the same solvent mixture, the eluant evaporated, the residue dissolved in chloroform/benzene mixture (1:1, 50 ml) and then evaporated and dried under vacuum. Yield of 10 was 1250 mg (74%), white solid. TLC: R$_f$=0.47 (4:3:1 (v/v/v) i-PrOH/ethyl acetate/water).

$^1$H NMR (500 MHz, [D$_6$]DMSO, 30° C.), mixture of cis- and trans-conformers of N-carboxymethylglycine unit c. 3:1. Major conformer; δ, ppm: 7.717 (t, J=5 Hz, 1H; N$\underline{H}$CO), 7.024 (t, J=5.9 Hz, 1H; N$\underline{H}$COO), 4.051 (s, 2H; NC$\underline{H}_2$COOCH$_3$), 3.928 (d, J=5 Hz, 2H; COC$\underline{H}_2$NH), 3.786 (s, 2H; NC$\underline{H}_2$COOH), 3.616 (s, 3H; OC$\underline{H}_3$), 3.563 (d, J=5.9 Hz, 2H; COC$\underline{H}_2$NHCOO), 1.381 (s, 9H; C(CH$_3$)$_3$) ppm; minor conformer, δ=7.766 (t, J=5 Hz, 1H; N$\underline{H}$CO), 7.015 (t, J=5.9 Hz, 1H; N$\underline{H}$COO), 4.288 (s, 2H; NC$\underline{H}_2$COOCH$_3$), 3.928 (d, J=5 Hz, 2H; COC$\underline{H}_2$NH), 3.858 (s, 2H; NC$\underline{H}_2$COOH), 3.676 (s, 3H; OC$\underline{H}_3$), 3.563 (d, J=5.9 Hz, 2H; COC$\underline{H}_2$NHCOO), 1.381 (s, 9H; C(CH$_3$)$_3$).

Preparation of {[2-(2-tert-Butoxycarbonylamino-acetylamino)-acetyl]-methoxycarbonylmethylamino}-acetic acid N-oxysuccinimide ester (Boc-Gly$_2$(MCMGly)Nos) (11) (SCHEME II)

To an ice-cooled stirred solution of (10) (1200 mg, 3.32 mmol) and N-hydroxysuccinimide (420 mg, 3.65 mmol) in DMF (10 ml) was added N,N'-dicyclohexylcarbodiimide (754 mg, 3.65 mmol). The mixture was stirred at 0° C. for 30 min, then for 2 hours at room temperature.

The precipitate of N,N'-dicyclohexylurea was filtered off, washed with DMF (5 ml), and filtrates evaporated to a minimal volume. The residue was then agitated with (CH$_3$CH$_2$)$_2$O (50 ml) for 1 hour and an ether extract removed by decantation. The residue was dried under vacuum providing the active ester (11) (1400 mg, 92%) as a white foam. TLC: R$_f$=0.71 (40:1 (v/v) acetone/acetic acid).

$^1$H NMR (500 MHz, [D$_6$]DMSO, 30° C.), mixture of cis- and trans-conformers of N-carboxymethylglycine unit c. 3:2.

Major conformer; δ, ppm: 7.896 (t, J=5.1 Hz, 1H; N$\underline{H}$CO), 6.972 (t, J=5.9 Hz, 1H; N$\underline{H}$COO), 4.533 (s, 2H; NC$\underline{H}_2$COON), 4.399 (s, 2H; NC$\underline{H}_2$COOCH$_3$), 3.997 (d, J=5.1 Hz, 2H; COC$\underline{H}_2$NH), 3.695 (s, 3H; OC$\underline{H}_3$), 3.566 (d, J=5.9 Hz, 2H; COC$\underline{H}_2$NHCOO), 1.380 (s, 9H; C(CH$_3$)$_3$).

Minor conformer; δ, ppm: 7.882 (t, J=5.1 Hz, 1H; N$\underline{H}$CO), 6.963 (t, J=5.9 Hz, 1H; N$\underline{H}$COO), 4.924 (s, 2H; NC$\underline{H}_2$COON), 4.133 (s, 2H; NC$\underline{H}_2$COOCH$_3$), 4.034 (d, J=5.1 Hz, 2H; COC$\underline{H}_2$NH), 3.632 (s, 3H; OC$\underline{H}_3$), 3.572 (d, J=5.9 Hz, 2H; COC$\underline{H}_2$NHCOO), 1.380 (s, 9H; C(CH$_3$)$_3$).

The active ester (11) (1380 mg) was dissolved in DMSO to provide a volume of 6 ml and used as a 0.5 M solution (stored at −18° C.).

Preparation of {CF$_3$COOH.H-[Gly$_2$(MCMGly)] Gly$_2$-NHCH$_2$}$_3$CCH$_3$ (13) (SCHEME IIIA)

To a stirred solution of (CF$_3$COOH.H-Gly$_2$-NHCH$_2$)$_3$CCH$_3$ (6) (401 mg, 0.5 mmol) in DMSO (4 ml) the active ester (11) (1.8 mmol, 3 ml of 0.6 M solution in DMSO) and (CH$_3$CH$_2$)$_3$N (417 μL, 3 mmol) was added.

The mixture was stirred for 3 h at room temperature, acidified with 300 μL AcOH and the solution passed through a Sephadex LH-20 gel column (2.4×40 cm) in 2:1 (v/v) methanol/water plus 0.5% AcOH.

Fractions containing 12 were combined, evaporated and dried. The residue was dissolved in 2:3:1 (v/v/v) 2-propanol/ethyl acetate/water mixture and fractionated on silica gel column (2.6×25 cm) (eluted with 2:3:1 (v/v/v) 2-propanol/ethyl acetate/water+0.5% AcOH).

Fractions contained pure 12 were combined, evaporated and dried. The residue was dissolved in 1:1 (v/v) acetone/2-propanol mixture (10 mL), filtered, and the filtrate evaporated and thoroughly dried under vacuum. Yield of pure {Boc-[Gly$_2$(MCMGly)]Gly$_2$-NHCH$_2$}$_3$CCH$_3$ (12) was 682 mg (91.5%), white solid. TLC: R$_f$=0.31 (2:3:1 (v/v/v) 2-propanol/ethyl acetate/water).

$^1$H NMR (500 MHz, [D$_6$]DMSO, 30° C.) (number of hydrogens per one chain) mixture of conformers; δ, ppm: 8.725-7.790 (triplets, 4H; N$\underline{H}$CO), 6.997 (t, J=6 Hz, 1H; N$\underline{H}$COO), 4.527-3.570 (15H; 5COC$\underline{H}_2$N, COC$\underline{H}_2$(COOCH$_3$)N, COCH$_2$(COOC$\underline{H}_3$)N), 2.846 (broad. d, J=6.1 Hz, 2H; C—C$\underline{H}_2$NH), 1.380 (s, 9H; C(CH$_3$)$_3$), 0.615 (s, one C$\underline{H}_3$ per whole molecule).

The {Boc-[Gly$_2$(MCMGly)]Gly$_2$-NHCH$_2$}$_3$CCH$_3$ (12) (560 mg, 0.376 mmol) was dissolved in CF$_3$COOH (2 ml) and the solution was kept for 60 min at room temperature. Trifluoroacetic acid was evaporated under vacuum, the residue extracted three times with (CH$_3$CH$_2$)$_2$O (slight agitation with 20 ml of (CH$_3$CH$_2$)$_2$O for 30 min followed by decantation) to eliminate residual CF$_3$COOH, and then dried, dissolved in water (c. 3 mL) and freeze-dried.

Yield of {CF$_3$COOH.H-[Gly$_2$(MCMGly)]Gly$_2$-NHCH$_2$}$_3$CCH$_3$ (13) was 564 mg (98%), white solid.

$^1$H NMR (500 MHz, [D$_2$]H$_2$O, 30° C.), (number of hydrogens per one chain) mixture of conformers; δ, ppm: 4.437-3.781 (15H; 5COC$\underline{H}_2$N, COC$\underline{H}_2$(COOCH$_3$)N, COCH$_2$(COOC$\underline{H}_3$)N), 3.019 (s, 2H; C—C$\underline{H}_2$NH), 0.786 (s, one C$\underline{H}_3$ per whole molecule).

Preparation of {CF$_3$COOH.H-[Gly$_2$(MCMGly)]$_2$Gly$_2$-NHCH$_2$}$_3$CCH$_3$ (21)

To a stirred solution of {CF$_3$COOH.H-[Gly$_2$(MCMGly)]Gly$_2$-NHCH$_2$}$_3$CCH$_3$ (13) (459 mg, 0.3 mmol) in DMSO (2 ml) the active ester (11) (1.125 mmol, 1.875 ml of 0.6 M solution in DMSO) and (CH$_3$CH$_2$)$_3$N (250 μL, 1.8 mmol) was added.

The mixture was stirred for 4 h at room temperature, acidified with 200 μL AcOH and the solution passed through a Sephadex LH-20 gel column (2.4×40 cm) in 2:1 (v/v) methanol/water plus 0.5% AcOH.

Fractions containing the product were combined, evaporated and freeze-dried from 2 ml of water. Yield of pure {Boc-[Gly$_2$(MCMGly)]$_2$Gly$_2$-NHCH$_2$}$_3$CCH$_3$ was (14) 627 mg (94%), white solid. TLC: R$_f$=0.29 (4:3:2 (v/v/v) 2-propanol/ethyl acetate/water).

$^1$H NMR (500 MHz, [D$_6$]DMSO, 30° C.), (number of hydrogens shown per one chain) mixture of conformers, δ, ppm: 8.524-7.772 (triplets, 6H; NHCO), 6.991 (t, J=6 Hz, 1H; NHCOO), 4.379-3.565 (26H; 8COCH$_2$N, 2COCH$_2$(COOCH$_3$)N, 2COCH$_2$(COOCH$_3$)N), 2.837 (broad. d, 2H; C—CH$_2$NH), 1.380 (s, 9H; C(CH$_3$)$_3$), 0.650 (s, one CH$_3$ per whole molecule).

The {Boc-[Gly$_2$(MCMGly)]$_2$Gly$_2$-NHCH$_2$}$_3$CCH$_3$ (14) (617 mg, 0.278 μmol) was dissolved in CF$_3$COOH (2 ml) and the solution kept for 60 min at room temperature. Trifluoroacetic acid was evaporated under vacuum, the residue was extracted three times with (CH$_3$CH$_2$)$_2$O (slight agitation with 15 ml of (CH$_3$CH$_2$)$_2$O for 30 min followed by decantation) to eliminate residual CF$_3$COOH, and then dried, dissolved in water (c. 3 mL) and freeze-dried.

Yield of {CF$_3$COOH.H-[Gly$_2$(MCMGly)]$_2$Gly$_2$-NHCH$_2$}$_3$CCH$_3$ (21) was 607 mg (97%), white solid.

$^1$H NMR (500 MHz, [D$_2$]H$_2$O, 30° C.), (number of hydrogens shown per one chain) mixture of conformers, δ, ppm: 4.443-3.781 (26H; 8COCH$_2$N, 2COCH$_2$(COOCH$_3$)N, 2COCH$_2$(COOCH$_3$)N), 3.018 (s, 2H; C—CH$_2$NH), 0.787 (s, one CH$_3$ per whole molecule).

Preparation of {CF$_3$COOH.H-[Gly$_2$(MCMGly)]$_3$Gly$_2$-NHCH$_2$}$_3$CCH$_3$ (27)

To a stirred solution of {CF$_3$COOH.H-[Gly$_2$(MCMGly)]$_2$Gly$_2$-NHCH$_2$}$_3$CCH$_3$ (21) (594 mg, 0.2627 mmol) in DMSO (3 ml) the active ester (11) (1.051 mmol, 1.752 ml of 0.6 M solution in DMSO) and (CH$_3$CH$_2$)$_3$N (219 μL, 1.576 mmol) was added.

The mixture was stirred for 4 h at room temperature, acidified with 180 μL AcOH and the solution passed through a Sephadex LH-20 gel column (2.4×40 cm) in 2:1 (v/v) methanol/water plus 0.5% AcOH.

Fractions containing the product were combined, evaporated and freeze-dried from 2 ml of water. Yield of pure {Boc-[Gly$_2$(MCMGly)]$_3$Gly$_2$-NHCH$_2$}$_3$CCH$_3$ was 756 mg (97.5%). TLC: R$_f$=0.48 (4:3:2 (v/v/v) 2-propanol/ethyl acetate/water).

$^1$H NMR (500 MHz, [D$_6$]DMSO, 30° C.), (number of hydrogens shown per one chain) mixture of conformers, δ, ppm: 8.519-7.773 (triplets, 8H; NHCO), 6.990 (t, J=6 Hz, 1H; NHCOO), 4.381-3.565 (37H; 11COCH$_2$N, 3COCH$_2$(COOCH$_3$)N, 3COCH$_2$(COOCH$_3$)N), 2.837 (broad. d, 2H; C—CH$_2$NH), 1.380 (s, 9H; C(CH$_3$)$_3$), 0.651 (s, one CH$_3$ per whole molecule).

The {Boc-[Gly$_2$(MCMGly)]$_3$Gly$_2$-NHCH$_2$}$_3$CCH$_3$ (739 mg, 0.2506 mmol) was dissolved in CF$_3$COOH (2.5 ml) and the solution was kept for 60 min at room temperature. Trifluoroacetic acid was evaporated under vacuum, the residue was extracted three times with (CH$_3$CH$_2$)$_2$O (slight agitation with 10 ml of (CH$_3$CH$_2$)$_2$O for 30 min followed by decantation) to remove residual CF$_3$COOH, and then dried, dissolved in water (c. 3 mL) and freeze-dried.

Yield of {CF$_3$COOH.H-[Gly$_2$(MCMGly)]$_3$Gly$_2$-NHCH$_2$}$_3$CCH$_3$ (27) was 719 mg (96%), white solid.

$^1$H NMR (500 MHz, [D$_2$]H$_2$O, 30° C.), (number of hydrogens shown per one chain) mixture of conformers, δ, ppm: 4.444-3.777 (37H; 11COCH$_2$N, 3COCH$_2$(COOCH$_3$)N, 3COCH$_2$(COOCH$_3$)N), 3.014 (s, 2H; C—CH$_2$NH), 0.784 (s, one CH$_3$ per whole molecule).

Preparation of {CF$_3$COOH.H-[Gly$_2$(MCMGly)]$_4$Gly$_2$-NHCH$_2$}$_3$CCH$_3$ (28)

To a stirred solution of {CF$_3$COOH.H-[Gly$_2$(MCMGly)]$_3$Gly$_2$-NHCH$_2$}$_3$CCH$_3$ (27) (507 mg, 0.1695 mmol) in DMSO (3 ml) the active ester (11) (0.7629 mmol, 1.272 ml of 0.6 M solution in DMSO) and (CH$_3$CH$_2$)$_3$N (141 μL, 1.017 mmol) was added.

The mixture was stirred for 4 h at room temperature, acidified with 200 μL AcOH and the solution passed through a Sephadex LH-20 gel column (2.4×40 cm) in 2:1 (v/v) methanol/water plus 0.5% AcOH.

Fractions containing the product were combined, evaporated to c. 3 ml volume and freeze dried. Yield of {Boc-[Gly$_2$(MCMGly)]$_4$Gly$_2$-NHCH$_2$}$_3$CCH$_3$ was 605 mg (97%). TLC: R$_f$=0.33 (4:3:2 (v/v/v) 2-propanol/ethyl acetate/water).

$^1$H NMR (500 MHz, [D$_6$]DMSO, 30° C.), (number of hydrogens shown per one chain) mixture of conformers, δ, ppm: 8.519-7.773 (triplets, 10H; NHCO), 6.990 (t, J=6 Hz, 1H; NHCOO), 4.381-3.565 (48H; 14COCH$_2$N, 4COCH$_2$(COOCH$_3$)N, 4COCH$_2$(COOCH$_3$)N), 2.838 (broad. d, 2H; C—CH$_2$NH), 1.380 (s, 9H; C(CH$_3$)$_3$), 0.651 (s, one CH$_3$ per whole molecule).

The {Boc-[Gly$_2$(MCMGly)]$_4$Gly$_2$-NHCH$_2$}$_3$CCH$_3$ (600 mg, 0.1631 mmol) was dissolved in CF$_3$COOH (2 ml) and the solution was kept for 60 min at room temperature. Trifluoroacetic acid was evaporated under vacuum, the residue was extracted three times with (CH$_3$CH$_2$)$_2$O (slight agitation with 10 ml of (CH$_3$CH$_2$)$_2$O for 30 min followed by decantation) to remove residual CF$_3$COOH, and then dried, dissolved in water (c. 3 mL) and freeze-dried.

Yield of {CF$_3$COOH.H-[Gly$_2$(MCMGly)]$_4$Gly$_2$-NHCH$_2$}$_3$CCH$_3$ (28) was 589 mg (97%), white solid.

$^1$H NMR (500 MHz, [D$_2$]H$_2$O, 30° C.), (number of hydrogens shown per one chain) mixture of conformers, δ, ppm: 4.445-3.781 (48H; 14COCH$_2$N, 4COCH$_2$(COOCH$_3$)N, 4COCH$_2$(COOCH$_3$)N), 3.017 (s, 2H; C—CH$_2$NH), 0.787 (s, one CH$_3$ per whole molecule).

Preparation of {CF$_3$COOH.H-[Gly$_2$(MCMGly)]$_5$Gly$_2$-NHCH$_2$}$_3$CCH$_3$ (29)

To a stirred solution of {CF$_3$COOH.H-[Gly$_2$(MCMGly)]$_4$Gly$_2$-NHCH$_2$}$_3$CCH$_3$ (28) (208 mg, 56 μmol) in DMSO (2 ml) the active ester (11) (251.6 μmol, 420 μL of 0.6 M solution in DMSO) and (CH$_3$CH$_2$)$_3$N (47 μl, 336 μmol) was added.

The mixture was stirred for h at room temperature, acidified with 150 μL AcOH and the solution passed through a Sephadex LH-20 gel column (2.4×40 cm) in 2:1 (v/v) methanol/water plus 0.5% AcOH.

Fractions containing the product were combined, evaporated to c. 2 ml volume and freeze dried. Yield of {Boc-[Gly$_2$(MCMGly)]$_5$Gly$_2$-NHCH$_2$}$_3$CCH$_3$ was 242 mg (98%), white solid. TLC: R$_f$=0.25 (4:3:2 (v/v/v) 2-propanol/ethyl acetate/water).

$^1$H NMR (500 MHz, [D$_6$]DMSO, 30° C.), (number of hydrogens shown per one chain) mixture of conformers, δ, ppm: 8.383-7.772 (triplets, 12H; NHCO), 6.990 (t, J=6 Hz, 1H; NHCOO), 4.304-3.564 (59H; 17COCH$_2$N, 5COCH$_2$(COOCH$_3$)N, 5COCH$_2$(COOCH$_3$)N), 2.837 (broad. d, 2H; C—CH$_2$NH), 1.380 (s, 9H; C(CH$_3$)$_3$), 0.651 (s, one CH$_3$ per whole molecule).

The {Boc-[Gly$_2$(MCMGly)]$_5$Gly$_2$-NHCH$_2$}$_3$CCH$_3$ (80.5 mg, 183 μmol) was dissolved in CF$_3$COOH (1 ml) and the solution was kept for 60 min at room temperature. Trifluoroacetic acid was evaporated under vacuum, the residue was extracted three times with $(CH_3CH_2)_2O$ (slight agitation with 5 ml of $(CH_3CH_2)_2O$ for 30 min followed by decantation) to remove residual $CF_3COOH$, and then dried, dissolved in water (c. 1 mL) and freeze-dried.

Yield of $\{CF_3COOH.H-[Gly_2(MCMGly)]_5Gly_2-NHCH_2\}_3CCH_3$ (29) was 76.4 mg (94%), white solid.

$^1H$ NMR (500 MHz, $[D_2]H_2O$, 30° C.), (number of hydrogens shown per one chain) mixture of conformers, δ, ppm: 4.445-3.780 (59H; 17COC$\underline{H}_2$N, 5COC$\underline{H}_2$(COOCH$_3$)N, 5COCH$_2$(COOC$\underline{H}_3$)N), 3.016 (s, 2H; C—C$\underline{H}_2$NH), 0.787 (s, one C$\underline{H}_3$ per whole molecule).

Preparation of $\{CF_3COOH.H-[Gly_2(MCMGly)]Gly_2-NHCH_2\}_4C$ (16) (SCHEME IIIB)

To a stirred solution of $(CF_3COOH.H-Gly_2-HNCH_2)_4C$ (7) (277 mg, 0.265 mmol) in DMSO (2 ml) the active ester (11) (1.591 mmol, 3.18 ml of 0.5 M solution in DMSO) and $(CH_3CH_2)_3N$ (295 μL, 2.121 mmol) were added.

The mixture was stirred overnight at room temperature, acidified with 150 μL AcOH and solvent removed under vacuum (freeze drying). The residue was extracted three times with $(CH_3CH_2)_2O$ (slight agitation with 20 ml of $(CH_3CH_2)_2O$ for 30 min followed by decantation).

The solid residue was dissolved in a minimal volume of acetone and fractionated on silica gel column (packed in acetone and eluted with acetone, 20:2:1 (v/v/v) acetone/methanol/water and 15:2:1 (v/v/v) acetone/methanol/water).

Selected fractions were evaporated and the residue was dried under vacuum. The yield of pure $\{Boc-[Gly_2(MCMGly)]Gly_2-NHCH_2\}_4C$ (15) was 351 mg (68%), white solid. TLC: $R_f$=0.38 (15:2:1 (v/v/v) acetone/methanol/water).

$^1H$ NMR (500 MHz, $[D_6]DMSO$, 30° C.), mixture of cis- and trans-conformers of N-carboxymethylglycine unit in chain c. 3:2.

Major conformer; δ, ppm: 8.593 (t, J=5 Hz, 1H; N$\underline{H}$CO), 8.335 (t, J=5.4 Hz, 1H; N$\underline{H}$CO), 7.821 (t, J=6.4 Hz, 1H; C—CH$_2$—N$\underline{H}$CO), 7.786 (t, J=5.1 Hz, 1H; N$\underline{H}$CO), 6.993 (t, J=6 Hz, 1H; N$\underline{H}$COO), 4.139 (s, 2H; NC$\underline{H}_2$CO), 4.074 (s, 2H; NC$\underline{H}_2$COO(CH$_3$)), 3.985 (d, J=5 Hz, 2H; COC$\underline{H}_2$NH), 3.887 (d, J=5.4 Hz, 2H; COC$\underline{H}_2$NH), 3.726 (d, J=5.1 Hz, 2H; COC$\underline{H}_2$NH), 3.634 (s, 3H; OC$\underline{H}_3$), 3.567 (d, J=6 Hz, 2H; COC$\underline{H}_2$NHCOO), 2.686 (broad. d, J=6.4 Hz, 2H; C—C$\underline{H}_2$NH), 1.379 (s, 9H; C(CH$_3$)$_3$).

Minor conformer; δ, ppm: 8.511 (t, J=5 Hz, 1H; N$\underline{H}$CO), 8.158 (t, J=5.4 Hz, 1H; N$\underline{H}$CO), 7.821 (t, J=6.4 Hz, 1H; C—CH$_2$—N$\underline{H}$CO), 7.786 (t, J=5.1 Hz, 1H; N$\underline{H}$CO), 6.993 (t, J=6 Hz, 1H; N$\underline{H}$COO), 4.292 (s, 2H; NC$\underline{H}_2$CO), 3.998 (s, 2H; NC$\underline{H}_2$COOCH$_3$), 3.954 (d, J=5 Hz, 2H; COC$\underline{H}_2$NH), 3.826 (d, J=5.4 Hz, 2H; COC$\underline{H}_2$NH), 3.715 (d, J=5.1 Hz, 2H; COC$\underline{H}_2$NH), 3.692 (s, 3H; OC$\underline{H}_3$), 3.567 (d, J=6 Hz, 2H; COC$\underline{H}_2$NHCOO), 2.686 (broad. d, J=6.4 Hz, 2H; C—C$\underline{H}_2$NH), 1.379 (s, 9H; C(CH$_3$)$_3$).

The $\{Boc-[Gly_2(MCMGly)]Gly_2-NHCH_2\}_4C$ (15) (330 mg, 0.168 mmol) was dissolved in $CF_3COOH$ (2 ml) and the solution was kept for 40 min at room temperature. Trifluoroacetic acid was evaporated under vacuum, the residue extracted three times with $(CH_3CH_2)_2O$ (slight agitation with 20 ml of $(CH_3CH_2)_2O$ for 30 min followed by decantation) to eliminate residual $CF_3COOH$, and then dried under vacuum.

The yield of $\{CF_3COOH.H-[Gly_2(MCMGly)]Gly_2-NHCH_2\}_4C$ (16) was 337 mg (99%), white solid.

$^1H$ NMR (500 MHz, $[D_2]H_2O$, 30° C.), mixture of cis- and trans-conformers of N-carboxymethylglycine unit in chain c. 11:10.

Major conformer; δ, ppm: 4.370 (s, 2H; NC$\underline{H}_2$CO), 4.265 (s, 2H; NC$\underline{H}_2$COOCH$_3$), 4.215 (s, 2H; COC$\underline{H}_2$NH), 4.138 (s, 2H; COC$\underline{H}_2$NH), 3.968 (s, 2H; COC$\underline{H}_2$NH), 3.919 (s, 2H; COC$\underline{H}_2$NH$_2^+$), 3.775 (s, 3H; OC$\underline{H}_3$), 2.914 (s, 2H; C—C$\underline{H}_2$NH).

Minor conformer; δ, ppm: 4.431 (s, 2H; NC$\underline{H}_2$CO), 4.241 (s, 2H; NC$\underline{H}_2$COOCH$_3$), 4.239 (s, 2H; COC$\underline{H}_2$NH), 4.074 (s, 2H; COC$\underline{H}_2$NH), 3.960 (s, 2H; COC$\underline{H}_2$NH), 3.919 (s, 2H; COC$\underline{H}_2$NH$_2^+$), 3.829 (s, 3H; OC$\underline{H}_3$), 2.914 (s, 2H; C—C$\underline{H}_2$NH).

Preparation of $\{CF_3COOH.H-[Gly_2(MCMGly)]_2Gly_2-NHCH_2\}_4C$ (22)

To a stirred solution of $(CF_3COOH.H-[Gly_2(MCMGly)]Gly_2-HNCH_2)_4C$ (16) (272 mg, 0.135 mmol) in DMSO (2 ml) the active ester (11) (0.809 mmol, 1.62 ml of 0.5 M solution in DMSO) and $(CH_3CH_2)_3N$ (112 μL, 0.809 mmol) were added.

The mixture was stirred overnight at room temperature, acidified with 70 μL AcOH and solvent removed under vacuum (freeze drying). The residue was extracted three times with $(CH_3CH_2)_2O$ (slight agitation with 15 ml of $(CH_3CH_2)_2O$ for 30 min followed by decantation).

Solid residue was dissolved in a minimal volume of 7:1 (v/v) acetone/methanol mixture and fractionated on a silica gel column (packed in acetone and eluted with 7:1 (v/v) acetone/methanol, 10:2:1 (v/v/v), 9:2:1 (v/v/v), 8:2:1 (v/v/v) acetone/methanol/water).

Selected fractions were evaporated and the residue was dried in vacuum. The yield of pure $\{Boc-[Gly_2(MCMGly)]_2Gly_2-NHCH_2\}_4C$ (17) was 279 mg (71%), white solid. TLC: $R_f$=0.42 (8:2:1 (v/v/v) acetone/methanol/water).

$^1H$ NMR (500 MHz, $[D_6]DMSO$, 30° C.), mixture of conformers by two N-carboxymethyl-glycine units per chain, δ, ppm: 8.604, 8.519, 8.397, 8.388, 8.346, 8.211, 8.200, 8.167, 8.034, 8.024, 7.925, 7.912, 7.819 and 7.773 (t, 6H; 6 N$\underline{H}$CO), 6.992 (t, J=5.9 Hz, 1H; N$\underline{H}$COO), 4.302-3.723 (18H; 2 NC$\underline{H}_2$CO, 2 NC$\underline{H}_2$COOCH$_3$, 5 COC$\underline{H}_2$NH), 3.692, 3.689 and 3.632 (s, 6H; 2 OC$\underline{H}_3$), 3.566 (d, J=5.9 Hz, 2H; COC$\underline{H}_2$NHCOO), 2.686 (broad. d, 2H; C—C$\underline{H}_2$NH), 1.380 (s, 9H; C(CH$_3$)$_3$).

The $\{Boc-[Gly_2(MCMGly)]_2Gly_2-NHCH_2\}_4C$ (17) (269 mg, 91.65 μmol) was dissolved in $CF_3COOH$ (2 ml) and the solution was kept for 40 min at room temperature. Trifluoroacetic acid was evaporated under vacuum, the residue extracted three times with $(CH_3CH_2)_2O$ (slight agitation with 15 ml of $(CH_3CH_2)_2O$ for 30 min followed by decantation) to remove residual $CF_3COOH$, and then dried under vacuum.

The yield of $\{CF_3COOH.H-[Gly_2(MCMGly)]_2Gly_2-NHCH_2\}_4C$ (22) was 270 mg (98%), white solid.

$^1H$ NMR (500 MHz, $[D_2]H_2O$, 30° C.), mixture of conformers by two N-carboxymethyl-glycine units per chain, δ, ppm: 4.441-3.963 (singlets, 18H; 2 NC$\underline{H}_2$CO, 2 NC$\underline{H}_2$COOCH$_3$, 5 COC$\underline{H}_2$NH), 3.920 (s, 2H; COC$\underline{H}_2$NH$_2^+$), 3.833, 3.824, 3.780 and 3.773 (s, 6H; 2 OC$\underline{H}_3$), 2.918 (s, 2H; C—C$\underline{H}_2$NH).

Preparation of $\{CF_3COOH.H-[Gly_2(MCMGly)]_3Gly_2-NHCH_2\}_4C$ (30)

To a stirred solution of $(CF_3COOH.H-[Gly_2(MCMGly)]_2Gly_2-HNCH_2)_4C$ (21) (175 mg, 58.5 μmol) in DMSO (2 ml) the active ester (11) (0.351 mmol, 0.702 ml of 0.5 M solution in DMSO) and $(CH_3CH_2)_3N$ (49 μL, 0.351 mmol) were added.

The mixture was stirred overnight at room temperature, acidified with 30 μL AcOH and solvent removed under vacuum (freeze drying). The residue was dissolved in a minimal volume of a mixture of 1:1 (v/v) acetonitrile/water and fractionated on a Sephadex LH-20 column (eluted with 1:1 (v/v) acetonitrile/water).

Selected fractions were evaporated and the residue was dried in vacuum. The yield of pure $\{Boc-[Gly_2(MCMGly)]_3Gly_2-NHCH_2\}_4C$ was 279 mg (71%), white solid. TLC: $R_f$=0.42 (8:2:1 (v/v/v) acetone/methanol/water).

Fractions containing $\{Boc-[Gly_2(MCMGly)]_3Gly_2-NHCH_2\}_4C$ were combined, evaporated to c. 2 ml volume and freeze dried. The initial yield was 215 mg (94%). Additional purification on a silica gel column (packed in acetonitrile and eluted with 4:5:2 (v/v/v) i-PrOH/acetonitrile/water) resulted in 169 mg of $Boc-[Gly_2(MCMGly)]_3Gly_2-NHCH_2\}_4C$ (yield 74%, white solid). TLC: $R_f$=0.45 (4:5:2 (v/v/v) i-PrOH/acetonitrile/water).

$^1$H NMR (500 MHz, $[D_6]$DMSO, 30° C.), mixture of conformers by three N-carboxymethyl-glycine units per chain, δ, ppm: 8.594-7.772 (triplets, together 8H; 8 N$\underline{H}$CO), 6.989 (t, J=5.6 Hz, 1H; N$\underline{H}$COO), 4.303-3.722 (26H; 3 NC$\underline{H}_2$CO$_3$ 3 NC$\underline{H}_2$COOCH$_3$, 7 COC$\underline{H}_2$NH), 3.692 and 3.632 (s, 9H; 3 OC$\underline{H}_3$), 3.565 (d, J=5.6 Hz, 2H; COC$\underline{H}_2$NHCOO), 2.687 (broad. d, 2H; C—C$\underline{H}_2$NH), 1.380 (s, 9H; C(CH$_3$)$_3$).

The $\{Boc-[Gly_2(MCMGly)]_3Gly_2-NHCH_2\}_4C$ (146 mg, 37.36 μmol) was dissolved in CF$_3$COOH (1 ml) and the solution was kept for 40 min at room temperature. Trifluoroacetic acid was evaporated under vacuum, the residue extracted three times with (CH$_3$CH$_2$)$_2$O (slight agitation with 10 ml of (CH$_3$CH$_2$)$_2$O for 30 min followed by decantation) to remove residual CF$_3$COOH, and then dried under vacuum.

The yield of $\{CF_3COOH.H-[Gly_2(MCMGly)]_3Gly_2-NHCH_2\}_4C$ (30) was 147 mg (99%), white solid.

$^1$H NMR (500 MHz, $[D_2]$H$_2$O, 30° C.), mixture of conformers by three N-carboxymethyl-glycine units per chain, δ, ppm: 4.446-3.964 (singlets, 26H; 3 NC$\underline{H}_2$CO, 3 NC$\underline{H}_2$COOCH$_3$, 7 COC$\underline{H}_2$NH), 3.924 (s, 2H; COC$\underline{H}_2$NH$_2$$^+$), 3.836, 3.828, 3.824, 3.783, 3.778 and 3.773 (s, 9H; 3 OC$\underline{H}_3$), 2.919 (s, 2H; C—C$\underline{H}_2$NH).

Preparation of $\{CF_3COOH.H-[Gly_2(MCMGly)]_4Gly_2-NHCH_2\}_4C$ (31)

To a stirred solution of (CF$_3$COOH.H-Gly$_2$(MCMGly)$_3$-HNCH$_2$)$_4$C (30) (68 mg, 17.16 μmol) in DMSO (1 ml) the active ester (11) (0.137 mmol, 0.275 ml of 0.5 M solution in DMSO) and (CH$_3$CH$_2$)$_3$N (14.3 μL, 0.103 mmol) were added.

The mixture was stirred overnight at room temperature, acidified with 100 μL AcOH and solvent removed under vacuum (freeze drying). The residue was dissolved in a minimal volume of a mixture of 1:1 (v/v) acetonitrile/water (0.25% AcOH) and fractionated on a Sephadex LH-20 column (eluted with 1:1 (v/v) acetonitrile/water (0.25% AcOH)).

Fractions containing $\{Boc-[Gly_2(MCMGly)]_4Gly_2-NHCH_2\}_4C$ were combined, evaporated to c. 2 ml volume and freeze dried. The yield was 81 mg (96%), white solid. TLC: $R_f$=0.24 (4:5:2 (v/v/v) i-PrOH/acetonitrile/water).

$^1$H NMR (500 MHz, $[D_6]$DMSO, 30° C.), mixture of conformers by four N-carboxymethyl-glycine units per chain, δ, ppm: 8.590-7.773 (triplets, 10H; 10 N$\underline{H}$CO), 6.989 (t, J=5.6 Hz, 1H; N$\underline{H}$COO), 4.303-3.722 (34H; 4 NC$\underline{H}_2$CO, 4 NC$\underline{H}_2$COOCH$_3$, 9 COC$\underline{H}_2$NH), 3.691 and 3.631 (s, 12H; 4 OC$\underline{H}_3$), 3.565 (d, J=5.6 Hz, 2H; COC$\underline{H}_2$NHCOO), 2.684 (broad. d, 2H; C—C$\underline{H}_2$NH), 1.379 (s, 9H; C(CH$_3$)$_3$).

The $\{Boc-[Gly_2(MCMGly)]_4Gly_2-NHCH_2\}_4C$ (74 mg, 15.16 μmol) was dissolved in CF$_3$COOH (1 ml) and the solution was kept for 40 min at room temperature. Trifluoroacetic acid was evaporated under vacuum, the residue extracted three times with (CH$_3$CH$_2$)$_2$O (slight agitation with 10 ml of (CH$_3$CH$_2$)$_2$O for 30 min followed by decantation) to remove residual CF$_3$COOH, and then dried under vacuum.

The yield of $\{CF_3COOH.H-[Gly_2(MCMGly)]_4Gly_2-NHCH_2\}_4C$ (31) was 72 mg (96%), white solid.

$^1$H NMR (500 MHz, $[D_2]$H$_2$O, 30° C.), mixture of conformers by four N-carboxymethyl-glycine units per chain, δ, ppm: 4.446-3.964 (singlets, 34H; 4 NC$\underline{H}_2$CO, 4 NC$\underline{H}_2$COOCH$_3$, 9 COC$\underline{H}_2$NH), 3.925 (s, 2H; COC$\underline{H}_2$NH$_2$$^+$), 3.836, 3.829, 3.827, 3.822, 3.783, 3.779, 3.777 and 3.772 (s, 12H; 4 OC$\underline{H}_3$), 2.919 (s, 2H; C—C$\underline{H}_2$NH).

Preparation of $\{CF_3COOH.H-[Gly_2(MCMGly)]_5Gly_2-NHCH_2\}_4C$ (32)

To a stirred solution of (CF$_3$COOH.H-Gly$_2$(MCMGly)]$_4$—HNCH$_2$)$_4$C (31) (16.8 mg, 3.403 μmol) in DMSO (1 ml) the active ester (11) (27.2 μmol, 63 μl of 0.5 M solution in DMSO) and (CH$_3$CH$_2$)$_3$N (3 μl, 21.6 μmol) were added.

The mixture was stirred overnight at room temperature, acidified with 100 μL AcOH and solvent removed under vacuum (freeze drying). The residue was dissolved in a minimal volume of a mixture of 1:1 (v/v) acetonitrile/water (0.25% AcOH) and fractionated on a Sephadex LH-20 column (eluted with 1:1 (v/v) acetonitrile/water (0.25% AcOH)).

Fractions containing $\{Boc-[Gly_2(MCMGly)]_5Gly_2-NHCH_2\}_4C$ were combined, evaporated to c. 1 ml volume and freeze dried. The yield was 19 mg (95%), white solid. TLC: $R_f$=0.15 (4:3:2 (v/v/v) i-PrOH/acetonitrile/water).

$^1$H NMR (500 MHz, $[D_6]$DMSO, 30° C.), mixture of conformers by five N-carboxymethyl-glycine units per chain, δ, ppm: 8.595-7.772 (triplets, 12H; 12 N$\underline{H}$CO), 6.989 (t, J=5.6 Hz, 1H; N$\underline{H}$COO), 4.303-3.723 (42H; 5 NC$\underline{H}_2$CO, 5 NC$\underline{H}_2$COOCH$_3$, 11 COC$\underline{H}_2$NH), 3.692 and 3.631 (s, 15H; 5 OC$\underline{H}_3$), 3.565 (d, J=5.6 Hz, 2H; COC$\underline{H}_2$NHCOO), 2.686 (broad. d, 2H; C—C$\underline{H}_2$NH), 1.380 (s, 9H; C(CH$_3$)$_3$).

The $\{Boc-[Gly_2(MCMGly)]_5Gly_2-NHCH_2\}_4C$ (19 mg, 3.25 μmol) was dissolved in CF$_3$COOH (0.5 ml) and the solution was kept for 40 min at room temperature. Trifluoroacetic acid was evaporated under vacuum, the residue extracted three times with (CH$_3$CH$_2$)$_2$O (slight agitation with 5 ml of (CH$_3$CH$_2$)$_2$O for 30 min followed by decantation) to remove residual CF$_3$COOH, and then dried under vacuum.

Yield of $\{CF_3COOH.H-[Gly_2(MCMGly)]_5Gly_2-NHCH_2\}_4C$ (32) was 20 mg (99%), white solid.

$^1$H NMR (500 MHz, $[D_2]$H$_2$O, 30° C.), mixture of conformers by five N-carboxymethyl-glycine units per chain, δ, ppm: 4.446-3.965 (singlets, 42H; 5 NC$\underline{H}_2$CO, 5 NC$\underline{H}_2$COOCH$_3$, 11 COC$\underline{H}_2$NH), 3.924 (s, 2H; COC$\underline{H}_2$NH$_2$$^+$), 3.835, 3.829, 3.827, 3.825, 3.823, 3.783, 3.779, 3.777 and 3.773 (s, 15H; 5 OC$\underline{H}_3$), 2.919 (s, 2H; C—C$\underline{H}_2$NH).

Preparation of Neu5Acα2-6Galβ1-4GlcNAcβ-O(CH$_2$)$_3$NH—CO(CH$_2$)$_4$CO—O(p-C$_6$H$_4$)NO$_2$ (6'SLN-S$_1$-S$_2$-Nph) (20) (SCHEME IVα)

To a stirred solution of Neu5Acα2-6Galβ1-4GlcNAcβ-O(CH$_2$)$_3$NH$_2$ (19) (100 mg, 0.1367 mmol) in DMSO (1 ml) a solution of adipic p-nitrophenyl diester (18) (372 mg, 0.957 mmol in 2 ml DMF) and (CH$_3$CH$_2$)$_3$N (19 μL, 0.1367 mmol) were added. The solution was kept for 15 h at room temperature, acidified with 100 μL of AcOH and diluted with 30 ml of 0.5% aqueous AcOH.

The precipitate of excess (18) was filtered off and washed with 0.5% aqueous AcOH. The filtrate was evaporated to minimal volume and passed through a Sephadex LH-20 column (eluted with 1:1 (v/v) acetonitrile/water, 0.5% AcOH). Fractions, containing pure (20), were combined, evaporated to c. 2 ml volume and freeze dried. Yield of (20) was 116 mg (87%), white solid. TLC: R$_f$=0.67 (4:3:2(v/v/v) i-PrOH/acetonitrile/water).

$^1$H NMR (500 MHz, [D$_2$]H$_2$O, 30° C.) δ, ppm: 8.350 and 7.391 (m, J$_{orto}$=9.2 Hz, 2H; p-C$_6$H$_4$), 4.528 (d, J=7.9 Hz, 1H; H1 Galβ), 4.435 (d, J=7.9 Hz, 1H; H1 GlcNAcβ), 4.028-3.549 (together 21H; H4, 5, 6, 7, 8, 9, 9' Neu5Acα, H2, 3, 4, 5, 6, 6' Galβ, H2, 3, 4, 5, 6, 6' GlcNAcβ, OCH$_2$CH$_2$CH$_2$N), 3.293 and 3.197 (m, 1H; OCH$_2$CH$_2$CH$_2$N), 2.744 (t, J=6.8 Hz, 2H; CH$_2$CH$_2$COO), 2.667 (dd, J$_{3ax}$=12.5 Hz, J$_4$=4.6 Hz, 1H; H3$_{eq}$ Neu5Acα), 2.320 (t, J=6.7 Hz, 2H; CH$_2$CH$_2$CONH), 2.062 and 2.039 (s, 3H; NHCOCH$_3$), 1.756 (m, 7H; H3$_{ax}$ Neu5Acα, OCH$_2$CH$_2$CH$_2$N, CH$_2$CH$_2$CH$_2$CO).

Preparation of GalNAcα1-3(Fucα1-2)Galβ-O(CH$_2$)$_3$NH—CO(CH$_2$)$_4$CO—O(p-C$_6$H$_4$)NO$_2$ (A$_{tri}$-S$_1$-S$_2$-Nph) (40A) (SCHEME IVβ)

To a stirred solution of GalNAcα1-3(Fucα1-2)Galβ-O(CH$_2$)$_3$NH$_2$ (39A) (31 mg, 0.05285 mmol) in DMSO (0.5 ml) a solution of adipic p-nitrophenyl diester (18) (102.6 mg, 0.2642 mmol in 1 ml DMF) was added. The solution was kept for 20 h at room temperature, acidified with 70 μL of AcOH and diluted with 17 ml of 0.5% aqueous AcOH.

The precipitate of excess (18) was filtered off and washed with 0.5% aqueous AcOH. The filtrate was evaporated to minimal volume and passed through a Sephadex LH-20 column (eluted with 1:1 (v/v) acetonitrile/water, 0.5% AcOH). Fractions, containing pure (40A) were combined, evaporated to c. 1 ml volume and freeze dried. Yield of (40A) was 40.4 mg (91%), white solid. TLC: R$_f$=0.69 (4:3:2 (v/v/v) i-PrOH/acetonitrile/water).

$^1$H NMR (500 MHz, [D$_2$]H$_2$O, 30° C.) δ, ppm: 8.359 and 7.398 (m, J$_{orto}$=9.2 Hz, 2H; p-C$_6$H$_4$), 5.303 (d, J=3.5 Hz, 1H; H1 Fucα), 5.179 (d, J=3.7 Hz, 1H; H1 GalNAcα), 4.516 (d, J=7.9 Hz, 1H; H1 Galβ), 4.409 (ddd, J$_6$=6.8 Hz, 1H; H5 Fucα), 4.235 (m, 3H; H2 GalNAcα, H5 GalNAcα, H4 Galβ), 4.004 (d, J~3 Hz, 1H; H4 GalNAcα), 3.971-3.699 (together 12H; H3, 6, 6' GalNAcα, H2, 3, 4 Fucα, H2, 3, 6, 6' Galβ) OCH$_2$CH$_2$CH$_2$N), 3.617 (dd, J=7.8 Hz, J=4.4 Hz, 1H; H5 Galβ), 3.280 (m, 2H; OCH$_2$CH$_2$CH$_2$N), 2.746 (t, J=7 Hz, 2H; CH$_2$CH$_2$COO), 2.324 (t, J=6.8 Hz, 2H; CH$_2$CH$_2$CONH), 2.051 (s, 3H; NHCOCH$_3$), 1.843 (q, 2H; OCH$_2$CH$_2$CH$_2$N) 1.744 (m, 4H; CH$_2$CH$_2$CH$_2$CO), 1.210 (d, J=6.6 Hz, 3H; CH$_3$ Fucα).

Preparation of Galα1-3(Fucα1-2)Galβ-O(CH$_2$)$_3$NH—CO(CH$_2$)$_4$CO—O(p-C$_6$H$_4$)NO$_2$ (B$_{tri}$-S$_1$-S$_2$-Nph) (40B) (SCHEME IVγ)

To a stirred solution of Galα1-3(Fucα1-2)Galβ-O(CH$_2$)$_3$NH$_2$ (39B) (34 mg, 0.0623 mmol) in DMSO (0.5 ml) a solution of adipic p-nitrophenyl diester (18) (121 mg, 0.312 mmol in 1.2 ml DMF) was added. The solution was kept for 20 h at room temperature, acidified with 80 μL of AcOH and diluted with 20 ml of 0.5% aqueous AcOH.

The precipitate of unreacted (18) was filtered off and washed with 0.5% aqueous AcOH. The filtrate was evaporated to minimal volume and passed through a Sephadex LH-20 column (eluted, with 1:1 (v/v) acetonitrile/water, 0.5% AcOH). Fractions, containing pure (40B) were combined, evaporated to c. 1 ml volume and freeze dried. Yield of (40B) was 46.2 mg (93%), white solid. TLC: R$_f$=0.71 (4:3:2 (v/v/v) i-PrOH/acetonitrile/water).

$^1$H NMR (500 MHz, [D$_2$]H$_2$O, 30° C.) δ, ppm: 8.335 and 7.373 (m, J$_{orto}$=9.3 Hz, 2H; p-C$_6$H$_4$), 5.257 (d, J=3.4 Hz, 1H; H1 Galα), 5.219 (d, J=3.2 Hz, 1H; H1 Fucα), 4.503 (d, J=7.9 Hz, 1H; H1 Galβ), 4.380 (ddd, J$_6$=6.8 Hz, 1H; H5 Fucα), 4.234 (s, 1H; H4 Galβ), 4.197 (m, J$_6$~J$_6$~6.2 Hz, 1H; H5 Galα), 3.960-3.677 (together 14H; H2, 3, 4, 6, 6' Galα, H2, 3, 6, 6' Galβ, H2, 3, 4 Fucα, OCH$_2$CH$_2$CH$_2$N), 3.626 (dd, J=7.8 Hz, J=4.4 Hz, 1H; H5 Galβ), 3.257 (m, 2H; OCH$_2$CH$_2$CH$_2$N), 2.721 (t, J=6.9 Hz, 2H; CH$_2$CH$_2$COO), 2.299 (t, J=6.8 Hz, 2H; CH$_2$CH$_2$CONH), 1.820 (quin., 2H; OCH$_2$CH$_2$CH$_2$N), 1.720 (m, 4H; CH$_2$CH$_2$CH$_2$CO), 1.173 (d, J=6.8 Hz, 3H; CH$_3$ Fucα).

General procedure for the preparation of {Neu5Acα2-6Galβ1-4GlcNAcβ-O(CH$_2$)$_3$NH—CO(CH$_2$)$_4$CO—[NHCH$_2$CO—NHCH$_2$CO—N(CH$_2$COOCH$_3$)CH$_2$CO]$_m$—NHCH$_2$CO—NHCH$_2$CO—NHCH$_2$}$_3$CCH$_3$, ammonium salt

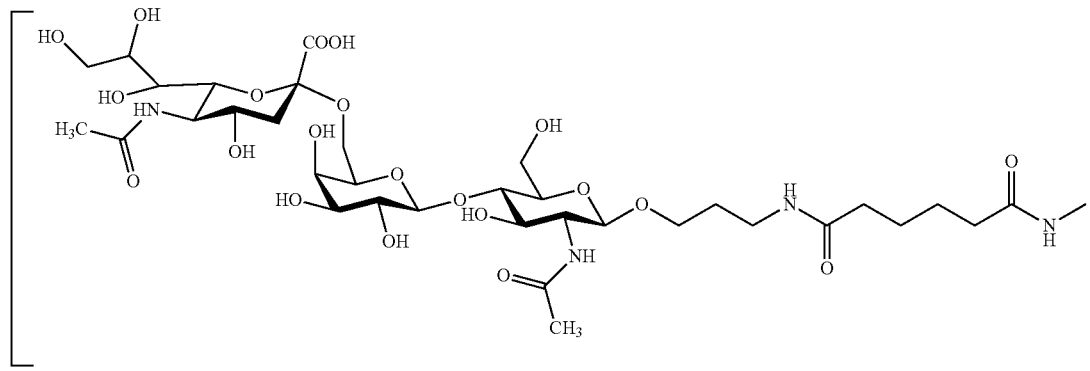

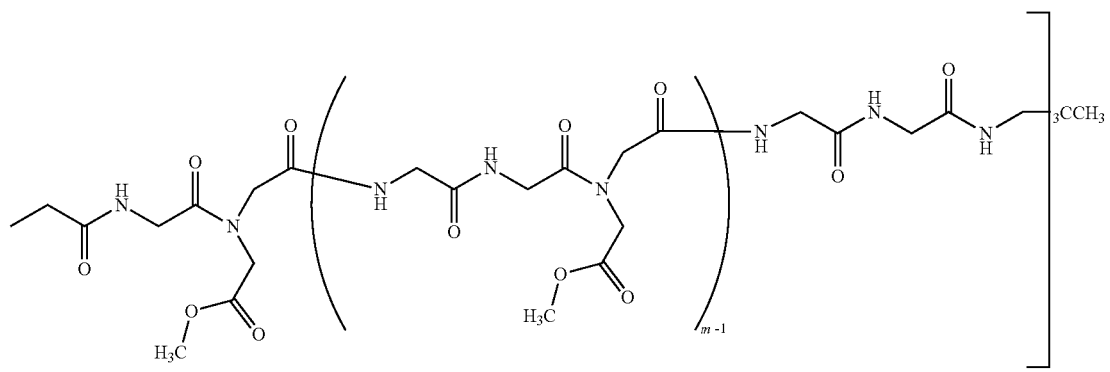

where m is the integer 3, 4 or 5 (41, 42 or 43) (cf. SCHEME VAα)

To the stirred solution of a product of Formula II (Table 2; 27, 28 or 29) (2 μmol) in DMSO (0.7 mL) 6'SLN-S$_1$-S$_2$-Nph (20) (7.4 mg, 7.5 μmol) and (CH$_3$CH$_2$)$_3$N (1.4 μL, 10 μmol) were added. The mixture was kept for 24 h at r.t., than (acylation was complete according to TLC data) was acidified with 20 μL of AcOH.

Reaction mixture was fractionated on Sephadex LH-20 column (eluent—MeCN/water (1:1), containing 0.02 M AcOH.Py). Fractions, containing pure glycopeptide (41, 42 or 43, respectively), were combined, evaporated and dried in vacuum. The residue was dissolved in ~1 mL of water, 80 μL of 0.1 M aqueous ammonia was added, and the solution was freeze dried.

Yield of {6'SLN-S$_1$-S$_2$-[Gly$_2$(MCMGly)]$_3$Gly$_2$-NHCH$_2$}$_3$CCH$_3$ (m is 3) (41) was 8.7 mg (83%), white solid. TLC: R$_f$=0.65 (methanol/acetonitrile/water 3:3:2).

$^1$H NMR (500 MHz, [D$_2$]H$_2$O, 30° C.): δ=4.555 (d, J=7.9 Hz, 1H; H1 Galβ), 4.459 (d, J=7.9 Hz, 1H; H1 GlcNAcβ), 4.439-3.535 (58H; 7H Neu5Acα, 6H Galβ, 6H GlcNAcβ, 3 OCH$_3$, OCH$_2$CH$_2$CH$_2$N, 28H peptide chain), 3.269 and 3.191 (m, 1H; OCH$_2$CH$_2$CH$_2$N), 3.008 (s, 2H; C—CH$_2$NH), 2.686 (dd, J$_{3ax}$=12.5 Hz, J$_4$=4.6 Hz, 1H; H3$_{eq}$ Neu5Acα), 2.364 and 2.271 (m, 2H; CH$_2$CH$_2$CO), 2.071 and 2.043 (s, 3H; NHCOCH$_3$), 1.784 (m, 2H; OCH$_2$CH$_2$CH$_2$N), 1.725 (t, J$_{3eq}$=J$_4$=12.5 Hz, 1H; H3$_{ax}$ Neu5Acα), 1.623 (m, 4H; CH$_2$CH$_2$CH$_2$CO), 0.780 (s, 3H/molecule; H$_3$C—C—CH$_2$NH) ppm.

Yield of {6'SLN-S$_1$-S$_2$-[Gly$_2$(MCMGly)]$_4$Gly$_2$-NHCH$_2$}$_3$CCH$_3$ (m is 4) (42) was 10.2 mg (86%), white solid. TLC: R$_f$=0.62 (methanol/acetonitrile/water 3:3:2).

$^1$H NMR (500 MHz, [D$_2$]H$_2$O, 30° C.): δ=4.555 (d, J=7.9 Hz, 1H; H1 Galβ), 4.459 (d, J=7.9 Hz, 1H; H1 GlcNAcβ), 4.435-3.532 (69H; 7H Neu5Acα, 6H Galβ, 6H GlcNAcβ, 4 OCH$_3$, OCH$_2$CH$_2$CH$_2$N, 36H peptide chain), 3.269 and 3.191 (m, 1H; OCH$_2$CH$_2$CH$_2$N), 3.003 (s, 2H; C—CH$_2$NH), 2.686 (dd, J$_{3ax}$=12.5 Hz, J$_4$=4.6 Hz, 1H; H3$_{eq}$ Neu5Acα), 2.364 and 2.271 (m, 2H; CH$_2$CH$_2$CO), 2.071 and 2.043 (s, 3H; NHCOCH$_3$), 1.784 (m, 2H; OCH$_2$CH$_2$CH$_2$N), 1.725 (t, J$_{3eq}$=J$_4$=12.5 Hz, 1H; H3$_{ax}$ Neu5Acα), 1.623 (m, 4H; CH$_2$CH$_2$CH$_2$CO), 0.775 (s, 3H/molecule; H$_3$C—C—CH$_2$NH) ppm.

Yield of {6'SLN-S$_1$-S$_2$-[Gly$_2$(MCMGly)]$_5$Gly$_2$-NHCH$_2$}$_3$CCH$_3$ (m is 5) (43) was 12.1 mg (91%, white solid. TLC: R$_f$=0.60 (methanol/acetonitrile/water 3:3:2).

$^1$H NMR (500 MHz, [D$_2$]H$_2$O, 30° C.): δ=4.555 (d, J=7.9 Hz, 1H; H1 Galβ), 4.459 (d, j=7.9 Hz, 1H; H1 GlcNAcβ), 4.439-3.536 (80H; 7H Neu5Acα, 6H Galβ, 6H GlcNAcβ, 5 OCH$_3$, OCH$_2$CH$_2$CH$_2$N, 44H peptide chain), 3.269 and 3.191 (m, 1H; OCH$_2$CH$_2$CH$_2$N), 3.007 (s, 2H; C—CH$_2$NH), 2.686 (dd, J$_{3ax}$=12.5 Hz, J$_4$=4.6 Hz, 1H; H3$_{eq}$ Neu5Acα), 2.364 and 2.271 (m, 2H; CH$_2$CH$_2$CO), 2.071 and 2.043 (s, 3H; NHCOCH$_2$), 1.784 (m, 2H; OCH$_2$CH$_2$CH$_2$N), 1.725 (t, J$_{3eq}$=J$_4$=12.5 Hz, 1H; H3$_{ax}$ Neu5Acα), 1.623 (m, 4H; CH$_2$CH$_2$CH$_2$CO), 0.779 (s, 3H/molecule; H$_3$C—C—CH$_2$NH) ppm.

General procedure for the preparation of {Neu5Acα2-6Galβ1-4GlcNAcβ-O(CH$_2$)$_3$NH—CO(CH$_2$)$_4$CO—[NHCH$_2$CO—NHCH$_2$CO—N(CH$_2$COOCH$_3$)CH$_2$CO]$_m$—NHCH$_2$CO—NHCH$_2$CO—NHCH$_2$}$_4$C, ammonium salt

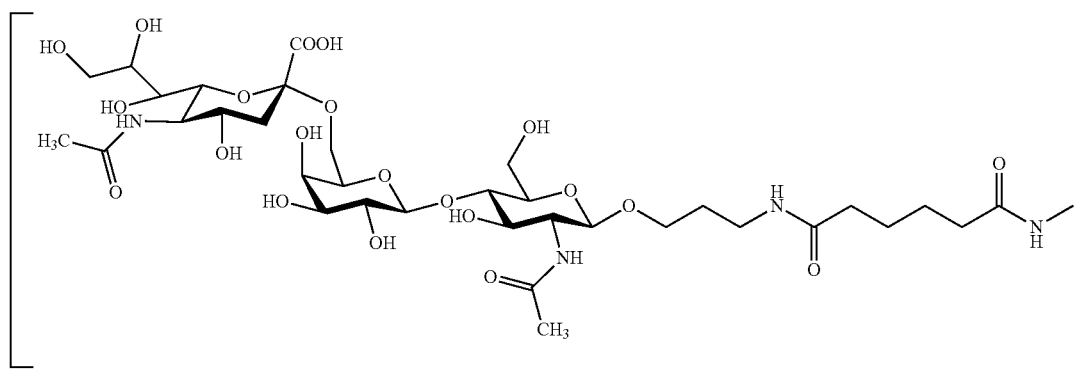

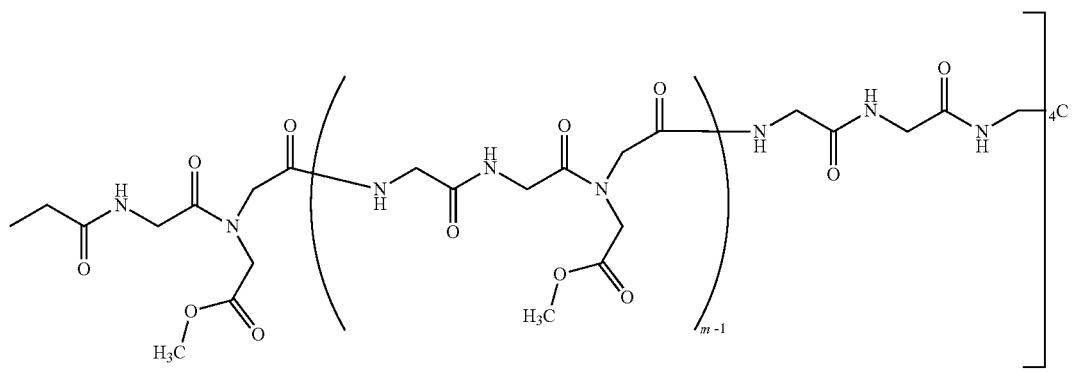

where m is the integer 3, 4 or 5 (44, 45 or 46) (cf. SCHEME VBα)

To a stirred solution of a product of Formula II (Table 3; 30, 31 or 32) (2 μmol) in DMSO (1 ml) was added 6'SLN-S$_1$-S$_2$-Nph (20) (9.8 mg, 10 mmol) and (CH$_3$CH$_2$)$_3$N (2 μL, 14.4 μmol). The mixture was kept for 36 hours at room temperature and on completion of acylation (monitored by TLC) acidified with 20 μL of acetic acid.

The reaction mixture was fractionated on a Sephadex LH-20 column (eluted with 1:1 (v/v) acetonitrile/water, containing 0.02 M AcOH.Py). Fractions containing pure tetraligand construct (44, 45 or 46) were combined, evaporated and dried under vacuum. The residue was dissolved in c. 1 ml of water, 80 μL of 0.1 M aqueous ammonia added, and the solution freeze dried.

Yield of {6'SLN-S$_1$-S$_2$-[Gly$_2$(MCMGly)]$_3$Gly$_2$-NHCH$_2$}$_4$C (m is 3) (44) was 13.2 mg (95%), white solid. TLC: R$_f$=0.32 (3:4:6:4 (v/v/v/v) methanol/i-PrOH/acetonitrile/water).

$^1$H NMR (500 MHz, [D$_2$]H$_2$O, 30° C.) δ, ppm: 4.510 (d, J=7.9 Hz, 1H; H1 Galβ), 4.415 (d, J=7.9 Hz, 1H; H1 GlcNAcβ), 4.390-3.489 (58H; 7H Neu5Acα, 6H Galβ, 6H GlcNAcβ, 3 OCH$_3$, OCH$_2$CH$_2$CH$_2$N, 28H peptide chain), 3.227 and 3.143 (m, 1H; OCH$_2$CH$_2$CH$_2$N), 2.865 (s, 2H; C—CH$_2$NH), 2.641 (dd, J$_{3ax}$=12.5 Hz, J$_4$=4.6 Hz, 1H; H3$_{eq}$ Neu5Acα), 2.317 and 2.223 (m, 2H; CH$_2$CH$_2$CO), 2.025 and 1.997 (s, 3H; NHCOCH$_3$), 1.736 (m, 2H; OCH$_2$CH$_2$CH$_2$N), 1.681 (t, J$_{3eq}$=J$_4$=12.5 Hz, 1H; H3$_{ax}$ Neu5Acα), 1.577 (m, 4H; CH$_2$CH$_2$CH$_2$CO).

Yield of {6'SLN-S$_1$-S$_2$-[Gly$_2$(MCMGly)]$_4$Gly$_2$-NHCH$_2$}$_4$C (m is 4) (45) was 15 mg (95%), white solid. TLC: R$_f$=0.25 (3:4:6:4 (v/v/v/v) methanol/i-PrOH/acetonitrile/water).

$^1$H NMR (500 MHz, [D$_2$]H$_2$O, 30° C.) δ, ppm: 4.509 (d, J=7.9 Hz, 1H; H1 Galβ), 4.414 (d, J=7.9 Hz, 1H; H1 GlcNAcβ), 4.389-3.488 (69H; 7H Neu5Acα, 6H Galβ, 6H GlcNAcβ, 4 OCH$_3$, OCH$_2$CH$_2$CH$_2$N, 36H peptide chain), 3.226 and 3.143 (m, 1H; OCH$_2$CH$_2$CH$_2$N), 2.864 (s, 2H; C—CH$_2$NH), 2.640 (dd, J$_{3ax}$=12.5 Hz, J$_4$=4.6 Hz, 1H; H3$_{eq}$ Neu5Acα), 2.315 and 2.222 (m, 2H; CH$_2$CH$_2$CO), 2.025 and 1.996 (s, 3H; NHCOCH$_3$), 1.735 (m, 2H; OCH$_2$CH$_2$CH$_2$N), 1.679 (t, J$_{3eq}$=J$_4$=12.5 Hz, 1H; H3$_{ax}$ Neu5Acα), 1.575 (m, 4H; CH$_2$CH$_2$CH$_2$CO).

Yield of {6'SLN-S$_1$-S$_2$-[Gly$_2$(MCMGly)]$_5$Gly$_2$-NHCH$_2$}$_4$C (m is 5) (46) was 16.4 mg (92%), white solid. TLC: R$_f$=0.22 (3:4:6:4 (v/v/v/v) methanol/i-PrOH/acetonitrile/water).

$^1$H NMR (500 MHz, [D$_2$]H$_2$O, 30° C.) δ, ppm: 4.509 (d, J=7.9 Hz, 1H; H1 Galβ), 4.415 (d, J=7.9 Hz, 1H; H1 GlcNAcβ), 4.389-3.488 (80H; 7H Neu5Acα, 6H Galβ, 6H GlcNAcβ, 5 OCH$_3$, OCH$_2$CH$_2$CH$_2$N, 44H peptide chain), 3.226 and 3.143 (m, 1H; OCH$_2$CH$_2$CH$_2$N), 2.863 (s, 2H; C—CH$_2$NH), 2.640 (dd, J$_{3ax}$=12.5 Hz, J$_4$=4.6 Hz, 1H; H3$_{eq}$ Neu5Acα), 2.315 and 2.222 (m, 2H; CH$_2$CH$_2$CO), 2.024 and 1.996 (s, 3H; NHCOCH$_3$), 1.735 (m, 2H; OCH$_2$CH$_2$CH$_2$N), 1.679 (t, J$_{3eq}$=J$_4$=12.5 Hz, 1H; H3$_{ax}$ Neu5Acα), 1.575 (m, 4H; CH$_2$CH$_2$CH$_2$CO).

General procedure for the preparation of {Neu5Acα2-6Galβ1-4GlcNAcβ-O(CH$_2$)$_3$NH—CO(CH$_2$)$_4$CO—[NHCH$_2$CO—NHCH$_2$CO—N(CH$_2$COOH)CH$_2$CO]$_m$—NHCH$_2$CO—NHCH$_2$CO—NHCH$_2$}$_3$CCH$_3$, ammonium salt

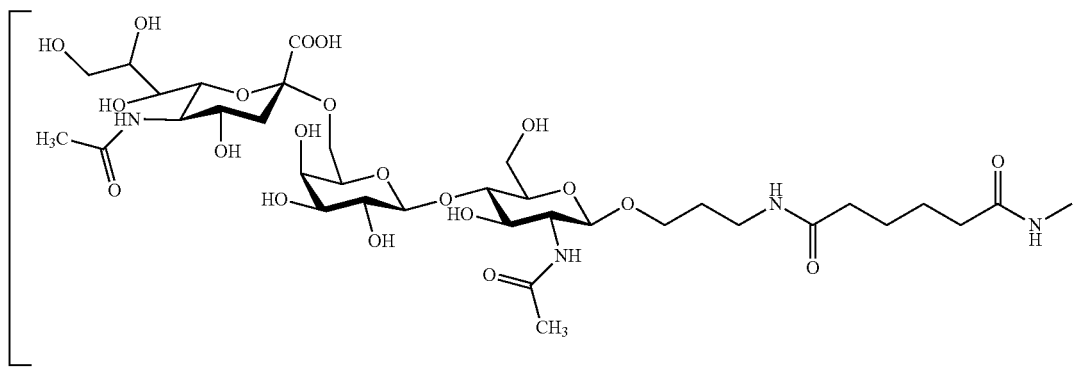

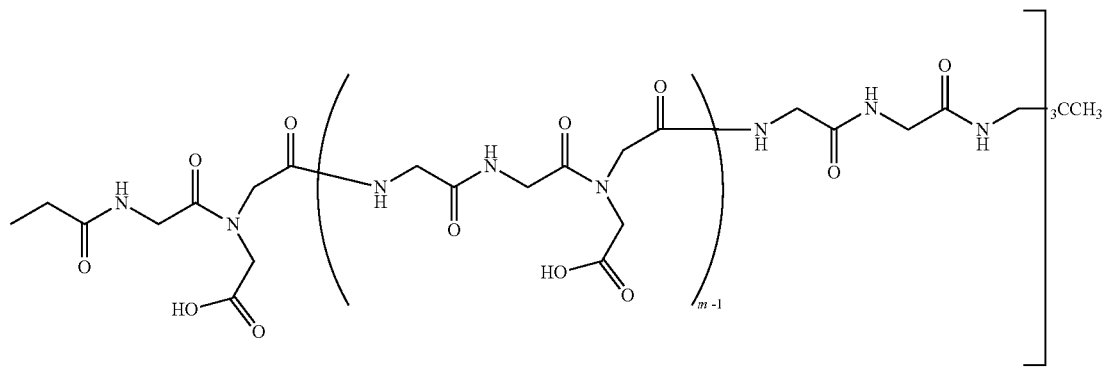

where m is the integer 2, 3, 4 or 5 (25, 47, 48 or 49) (cf. SCHEME VIAα)

To a stirred solution of the product 21 or a product of Formula II (Table 2; 27, 28 or 29) (2 μmol) in DMSO (0.7 ml) was added 6'SLN-S$_1$-S$_2$-Nph (20) (7.4 mg, 7.5 μmol) and (CH$_3$CH$_2$)$_3$N (1.4 μl, 10 μmol). The mixture was kept for 24 hours at room temperature, 7 μL of (CH$_3$CH$_2$)$_3$N added, and the mixture then kept for 3 hours at room temperature.

The reaction mixture was diluted with water (1.5 ml), (CH$_3$CH$_2$)$_3$N (70 μL) added, and the mixture kept for 24 h at room temperature.

The reaction mixture was then evaporated to minimal volume and the residue fractionated on a Sephadex LH-20 column (eluted with 0.2 M aqueous NH$_3$ in 1:1 (v/v) acetonitrile-water). Fractions containing pure multiligand construct were combined, evaporated to c. 1 ml volume and freeze dried.

Yield of {6'SLN-S$_1$-S$_2$-[Gly$_2$(CMGly)]$_2$Gly$_2$-NHCH$_2$}$_3$CCH$_3$ (m is 2) (25) was 8.0 mg (89%), white solid. TLC: R$_f$=0.41 (3:3:2 (v/v/v) methanol/acetonitrile/water).

$^1$H NMR (500 MHz, [D$_2$]H$_2$O, 30° C.) δ, ppm: 4.555 (d, J=7.5 Hz, 1H; H1 Galβ), 4.460 (d, J=7.8 Hz, 1H; H1 GlcNAcβ), 4.297-3.535 (41H; 7H Neu5Acα, 6H Galβ, 6H GlcNAcβ, OC$\underline{H}_2$CH$_2$CH$_2$N, 20H peptide chain), 3.269 and 3.191 (m, 1H; OCH$_2$CH$_2$C$\underline{H}_2$N), 3.031 (s, 2H; C—C$\underline{H}_2$NH), 2.687 (dd, J$_{3ax}$=12.5 Hz, J$_4$=4.6 Hz, 1H; H3$_{eq}$ Neu5Acα), 2.364 and 2.272 (m, 2H; CH$_2$C$\underline{H}_2$CO), 2.072 and 2.043 (s, 3H; NHCOC$\underline{H}_3$), 1.784 (m, 2H; OCH$_2$C$\underline{H}_2$CH$_2$N), 1.726 (t, J$_{3eq}$=J$_4$=12.5 Hz, 1H; H3$_{ax}$ Neu5Acα), 1.623 (m, 4H; C$\underline{H}_2$CH$_2$CH$_2$CO), 0.790 (s, 3H/molecule; $\underline{H}_3$C—C—CH$_2$NH).

Yield of {6'SLN-linker-[Gly$_2$(CMGly)]$_3$Gly$_2$-NHCH$_2$}$_3$CCH$_3$ (m is 3) (47) was 9.7 mg (92%), white solid. TLC: R$_f$=0.36 (3:3:2 (v/v/v) methanol/acetonitrile/water).

$^1$H NMR (500 MHz, [D$_2$]H$_2$O, 30° C.) δ, ppm: 4.555 (d, J=7.9 Hz, 1H; H1 Galβ), 4.459 (d, J=7.9 Hz, 1H; H1 GlcNAcβ), 4.295-3.535 (49H; 7H Neu5Acα, 6H Galβ, 6H GlcNAcβ, OC$\underline{H}_2$CH$_2$CH$_2$N, 28H peptide chain), 3.269 and 3.191 (m, 1H; OCH$_2$CH$_2$C$\underline{H}_2$N), 3.032 (s, 2H; C—C$\underline{H}_2$NH), 2.686 (dd, J$_{3ax}$=12.5 Hz, J$_4$=4.6 Hz, 1H; H3$_{eq}$ Neu5Acα), 2.364 and 2.271 (m, 2H; CH$_2$C$\underline{H}_2$CO), 2.071 and 2.043 (s, 3H; NHCOC$\underline{H}_3$), 1.784 (m, 2H; OCH$_2$C$\underline{H}_2$CH$_2$N), 1.725 (t, J$_{3eq}$=J$_4$=12.5 Hz, 1H; H3$_{ax}$ Neu5Acα), 1.623 (m, 4H; C$\underline{H}_2$CH$_2$CH$_2$CO), 0.790 (s, 3H/molecule; $\underline{H}_3$C—C—CH$_2$NH).

Yield of {6'SLN-linker-[Gly$_2$(CMGly)]$_4$Gly$_2$-NHCH$_2$}$_3$CCH$_3$ (m is 4) (48) was 11 mg (91%), white solid. TLC: R$_f$=0.34 (3:3:2 (v/v/v) methanol/acetonitrile/water).

$^1$H NMR (500 MHz, [D$_2$]H$_2$O, 30° C.) δ, ppm: 4.555 (d, J=7.9 Hz, 1H; H1 Galβ), 4.459 (d, J=7.9 Hz, 1H; H1 GlcNAcβ), 4.295-3.535 (57H; 7H Neu5Acα, 6H Galβ, 6H GlcNAcβ, OC$\underline{H}_2$CH$_2$CH$_2$N, 36H peptide chain), 3.269 and 3.191 (m, 1H; OCH$_2$CH$_2$C$\underline{H}_2$N), 3.034 (s, 2H; C—C$\underline{H}_2$NH), 2.686 (dd, J$_{3ax}$=12.5 Hz, J$_4$=4.6 Hz, 1H; H3$_{eq}$ Neu5Acα), 2.364 and 2.271 (m, 2H; CH$_2$C$\underline{H}_2$CO), 2.071 and 2.043 (s, 3H; NHCOC$\underline{H}_3$), 1.784 (m, 2H; OCH$_2$C$\underline{H}_2$CH$_2$N), 1.725 (t, J$_{3eq}$=J$_4$=12.5 Hz, 1H; H3$_{ax}$ Neu5Acα), 1.623 (m, 4H; C$\underline{H}_2$C$\underline{H}_2$CH$_2$CO), 0.792 (s, 3H/molecule; $\underline{H}_3$C—C—CH$_2$NH).

Yield of {6'SLN-linker-[Gly$_2$(CMGly)]$_5$Gly$_2$-NHCH$_2$}$_3$CCH$_3$ (m is 5) (49) was 12.4 mg (92%), white solid. TLC: R$_f$=0.33 (3:3:2 (v/v/v) methanol/acetonitrile/water).

$^1$H NMR (500 MHz, [D$_2$]H$_2$O, 30° C.) δ, ppm: 4.555 (d, J=7.9 Hz, 1H; H1 Galβ), 4.459 (d, J=7.9 Hz, 1H; H1 GlcNAcβ), 4.295-3.535 (65H; 7H Neu5Acα, 6H Galβ, 6H GlcNAcβ, OC$\underline{H}_2$CH$_2$CH$_2$N, 44H peptide chain), 3.269 and 3.191 (m, 1H; OCH$_2$CH$_2$C$\underline{H}_2$N), 3.035 (s, 2H; C—C$\underline{H}_2$NH), 2.686 (dd, J$_{3ax}$=12.5 Hz, (J$_4$=4.6 Hz, 1H; H3$_{eq}$ Neu5Acα). 2.364 and 2.271 (m, 2H; CH$_2$C$\underline{H}_2$CO), 2.071 and 2.043 (s, 3H; NHCOC$\underline{H}_3$), 1.784 (m, 2H; OCH$_2$C$\underline{H}_2$CH$_2$N), 1.725 (t, J$_{3eq}$=J$_4$=12.5 Hz, 1H; H3$_{ax}$ Neu5Acα), 1.623 (m, 4H; C$\underline{H}_2$C$\underline{H}_2$CH$_2$CO), 0.792 (s, 3H/molecule; $\underline{H}_3$C—C—CH$_2$NH).

General procedure for the preparation of {Neu5Acα2-6Galβ1-4GlcNAcβ-O(CH$_2$)$_3$NH—CO(CH$_2$)$_4$CO—[NHCH$_2$CO—NHCH$_2$CO—N(CH$_2$COOH)CH$_2$CO]$_m$—NHCH$_2$CO—NHCH$_2$CO—NHCH$_2$}$_4$C, ammonium salt

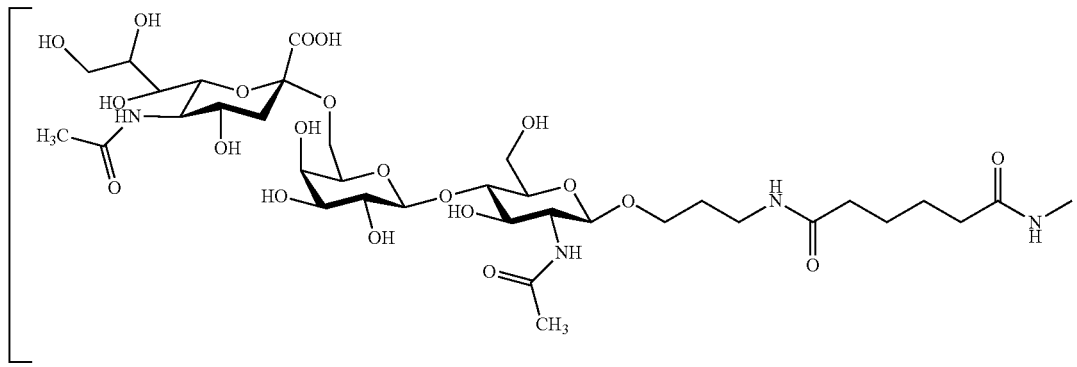

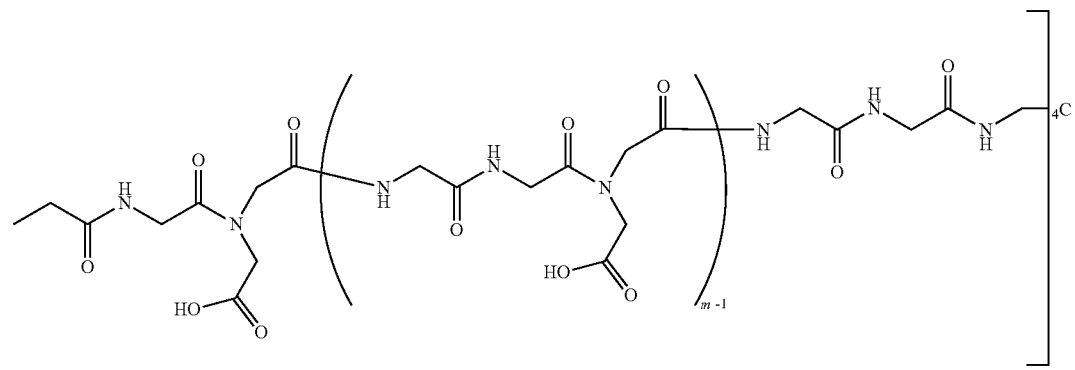

where m is the integer 3, 4 or 5 (50, 51 or 52) (cf. SCHEME VIBα)

To a stirred solution of a product of Formula II (Table 3; 30, 31 or 32) (5.1 μmol) in DMSO (1 ml) was added 6'SLN-S$_1$-S$_2$-Nph (20) (25 mg, 25.5 μmol) and (CH$_3$CH$_2$)$_3$N (5 μL, 35.7 μmol). The mixture was kept for 24 hours at room temperature, 10 μL of (CH$_3$CH$_2$)$_3$N added, and the mixture then kept for 3 hours at room temperature.

The reaction mixture was diluted with water (2 ml), (CH$_3$CH$_2$)$_3$N (90 μL) added, and the mixture kept for 24 h at room temperature.

The reaction mixture was then evaporated to minimal volume and the residue fractionated on a Sephadex LH-20 column (eluted with 0.2 M aqueous NH$_3$). Fractions containing pure multiligand construct were combined, evaporated to c. 1 ml volume and freeze dried.

Yield of {6'SLN-S$_1$-S$_2$-[Gly$_2$(CMGly)]$_3$Gly$_2$-NHCH$_2$}$_4$C (m is 3) (50) was 31.1 mg (87%), white solid. TLC: R$_f$=0.54 (3:3:2 (v/v/v) methanol/acetonitrile/water).

$^1$H NMR (500 MHz, [D$_2$]H$_2$O, 30° C.) δ, ppm: 4.509 (d, J=7.9 Hz, 1H; H1 Galβ), 4.414 (d, J=7.9 Hz, 1H; H1 GlcNAcβ), 4.254-3.488 (49H; 7H Neu5Acα, 6H Galβ, 6H GlcNAcβ, OCH$_2$CH$_2$CH$_2$N, 28H peptide chain), 3.226 and 3.146 (m, 1H; OCH$_2$CH$_2$CH$_2$N), 2.904 (s, 2H; C—CH$_2$NH), 2.640 (dd, J$_{3ax}$=12.5 Hz, J$_4$=4.6 Hz, 1H; H3$_{eq}$ Neu5Acα), 2.320 and 2.227 (m, 2H; CH$_2$CH$_2$CO), 2.027 and 1.998 (s, 3H; NHCOCH$_3$), 1.740 (m, 2H; OCH$_2$CH$_2$CH$_2$N), 1.684 (t, J$_{3eq}$=J$_4$=12.5 Hz, 1H; H3$_{ax}$ Neu5Acα), 1.578 (m, 4H; CH$_2$CH$_2$CH$_2$CO).

Yield of {6'SLN-S$_1$-S$_2$-[Gly$_2$(CMGly)]$_4$Gly$_2$-NHCH$_2$}$_4$C (m is 4) (51) was 32.7 mg (81%), white solid. TLC: R$_f$=0.52 (3:3:2 (v/v/v) methanol/acetonitrile/water).

$^1$H NMR (500 MHz, [D$_2$]H$_2$O, 30° C.) δ, ppm: 4.508 (d, J=7.9 Hz, 1H; H1 Galβ), 4.414 (d, J=7.9 Hz, 1H; H1 GlcNAcβ), 4.254-3.489 (57H; 7H Neu5Acα, 6H Galβ, 6H GlcNAcβ, OCH$_2$CH$_2$CH$_2$N, 36H peptide chain), 3.226 and 3.146 (m, 1H; OCH$_2$CH$_2$CH$_2$N), 2.903 (s, 2H; C—CH$_2$NH), 2.640 (dd, J$_{3ax}$=12.5 Hz, J$_4$=4.6 Hz, 1H; H3$_{eq}$ Neu5Acα), 2.320 and 2.227 (m, 2H; CH$_2$CH$_2$CO), 2.027 and 1.997 (s, 3H; NHCOCH$_3$), 1.739 (m, 2H; OCH$_2$CH$_2$CH$_2$N), 1.683 (t, J$_{3eq}$=J$_4$=12.5 Hz, 1H; H3$_{ax}$ Neu5Acα), 1.578 (m, 4H; CH$_2$CH$_2$CH$_2$CO).

Yield of {6'SLN-S$_1$-S$_2$-[Gly$_2$(CMGly)]$_5$Gly$_2$-NHCH$_2$}$_4$C (m is 5) (52) was 26.4 mg (91%), white solid. TLC: R$_f$=0.37 (3:3:2 (v/v/v) methanol/acetonitrile/water).

$^1$H NMR (500 MHz, [D$_2$]H$_2$O, 30° C.) δ, ppm: 4.508 (d, J=7.9 Hz, 1H; H1 Galβ), 4.414 (d, J=7.9 Hz, 1H; H1 GlcNAcβ), 4.252-3.488 (65H; 7H Neu5Acα, 6H Galβ, 6H GlcNAcβ, OCH$_2$CH$_2$CH$_2$N, 44H peptide chain), 3.226 and 3.146 (m, 1H; OCH$_2$CH$_2$CH$_2$N), 2.903 (s, 2H; C—CH$_2$NH), 2.640 (dd, J$_{3ax}$=12.5 Hz, J$_4$=4.6 Hz, 1H; H3$_{eq}$ Neu5Acα), 2.320 and 2.227 (m, 2H; CH$_2$CH$_2$CO), 2.026 and 1.997 (s, 3H; NHCOC$\underline{H}_3$), 1.738 (m, 2H; OCH$_2$C$\underline{H}_2$CH$_2$N), 1.681 (t, $J_{3eq}$=$J_4$=12.5 Hz, 1H; H3$_{ax}$ Neu5Acα), 1.577 (m, 4H; C$\underline{H}_2$C$\underline{H}_2$CH$_2$CO).

General procedure for the preparation of {Gal-NAcα1-3(Fucα1-2)Galβ-O(CH$_2$)$_3$NH—CO(CH$_2$)$_4$CO—[NHCH$_2$CO—NHCH$_2$CO—N(CH$_2$COOH)CH$_2$CO]$_m$—NHCH$_2$CO—NHCH$_2$CO—NHCH$_2$}$_4$C, ammonium salt

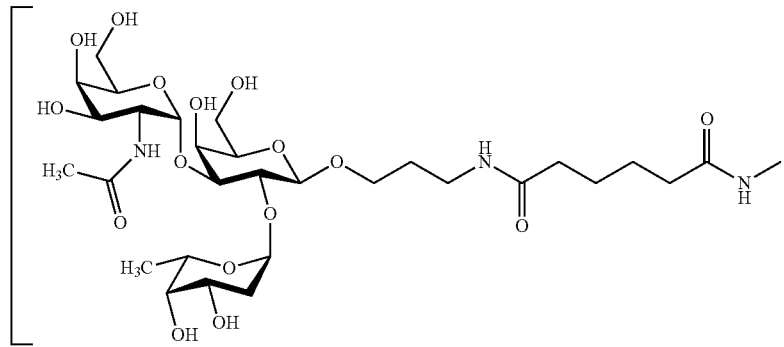

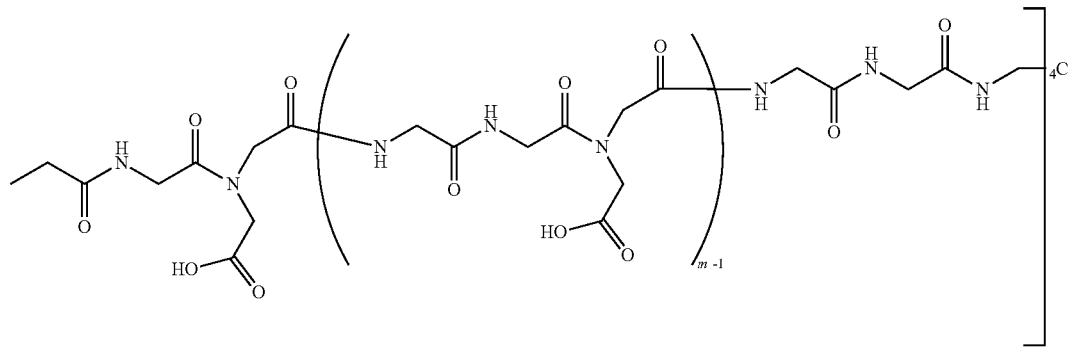

where m is the integer 3 or 5 (53A or 54A) (cf. SCHEME VIIA)

To a stirred solution of a product of Formula II (Table 3; 30 or 32) (2 μmol) in DMSO (0.5 ml) was added (A$_{tri}$-S$_1$-S$_2$-Nph) (40A) (10 mg, 12 μmol) in DMSO (200 μl) and (CH$_3$CH$_2$)$_3$N (3 μL, 21.6 μmol). The mixture was kept for 15 hours at room temperature, 5 μL of (CH$_3$CH$_2$)$_3$N added and the mixture then kept for 5 hours at room temperature.

The reaction mixture was diluted with water (1.4 ml), (CH$_3$CH$_2$)$_3$N (65 μL) added, and the mixture kept for 18 hours at room temperature.

The reaction mixture was then evaporated to minimal volume and the residue fractionated on a Sephadex LH-20 column (eluted with 0.2 M aqueous NH$_3$). Fractions containing pure multiligand construct were combined, evaporated to c. 1 ml volume and freeze dried.

Yield of {A$_{tri}$-S$_1$-S$_2$-[Gly$_2$(CMGly)]$_3$Gly$_2$-NHCH$_2$}$_4$C (m is 3) (53A) was 10.9 mg (86%), white solid. TLC: R$_f$=0.64 (1:1:1 (v/v/v) methanol/acetonitrile/water).

$^1$H NMR (500 MHz, [D$_2$]H$_2$O, 30° C.) δ, ppm: 5.333 (d, J=3.7 Hz, 1H; H1 Fucα), 5.208 (d, J=3.5 Hz, 1H; H1 Gal-NAcα), 4.563 (d, J=7.8 Hz, 1H; H1 Galβ), 4.439 (ddd, J$_6$=6.7 Hz, 1H; H5 Fucα), 4.320-3.676 (together 45H; 6H GalNAcα, 3H Fucα, 6H Galβ, OC$\underline{H}_2$CH$_2$CH$_2$N, 28H peptide chain), 3.285 (m, 2H; OCH$_2$CH$_2$C$\underline{H}_2$N), 2.971 (broad s, 2H; central C—C$\underline{H}_2$—NH), 2.382 and 2.291 (m, 2H; CH$_2$C$\underline{H}_2$CONH), 2.075 (s, 3H; NHCOC$\underline{H}_3$), 1.862 (q, 2H; OCH$_2$C$\underline{H}_2$CH$_2$N), 1.642 (m, 4H; C$\underline{H}_2$C$\underline{H}_2$CH$_2$CO), 1.242 (d, J=6.6 Hz, 3H; CH$_3$ Fucα).

Yield of {A$_{tri}$-S$_1$-S$_2$-[Gly$_2$(CMGly)]$_5$Gly$_2$-NHCH$_2$}$_4$C (m is 5) (54A) was 14.2 mg (85%), white solid. TLC: R$_f$=0.60 (1:1:1 (v/v/v) methanol/acetonitrile/water).

$^1$H NMR (500 MHz, [D$_2$]H$_2$O, 30° C.) δ, ppm: 5.334 (d, J=3.7 Hz, 1H; H1 Fucα), 5.209 (d, J=3.5 Hz, 1H; H1 Gal-NAcα), 4.563 (d, J=7.8 Hz, 1H; H1 Galβ), 4.440 (ddd, J$_6$=6.7 Hz, 1H; H5 Fucα), 4.325-3.676 (together 61H; 6H GalNAcα, 3H Fucα, 6H Galβ, OC$\underline{H}_2$CH$_2$CH$_2$N, 44H peptide chain), 3.285 (m, 2H; OCH$_2$CH$_2$C$\underline{H}_2$N), 2.971 (broad s, 2H; central C—C$\underline{H}_2$—NH), 2.382 and 2.292 (m, 2H; CH$_2$C$\underline{H}_2$CONH), 2.076 (s, 3H; NHCOC$\underline{H}_3$), 1.863 (q, 2H; OCH$_2$C$\underline{H}_2$CH$_2$N), 1.643 (m, 4H; C$\underline{H}_2$C$\underline{H}_2$CH$_2$CO), 1.243 (d, J=6.6 Hz, 3H; CH$_3$ Fucα).

General procedure for the preparation of {Galα1-3(Fucα1-2)Galβ-O(CH$_2$)$_3$NH—CO(CH$_2$)$_4$CO—[NHCH$_2$CO—NHCH$_2$CO—N(CH$_2$COOH)CH$_2$CO]$_m$—NHCH$_2$CO—NHCH$_2$CO—NHCH$_2$}$_4$C, ammonium salt

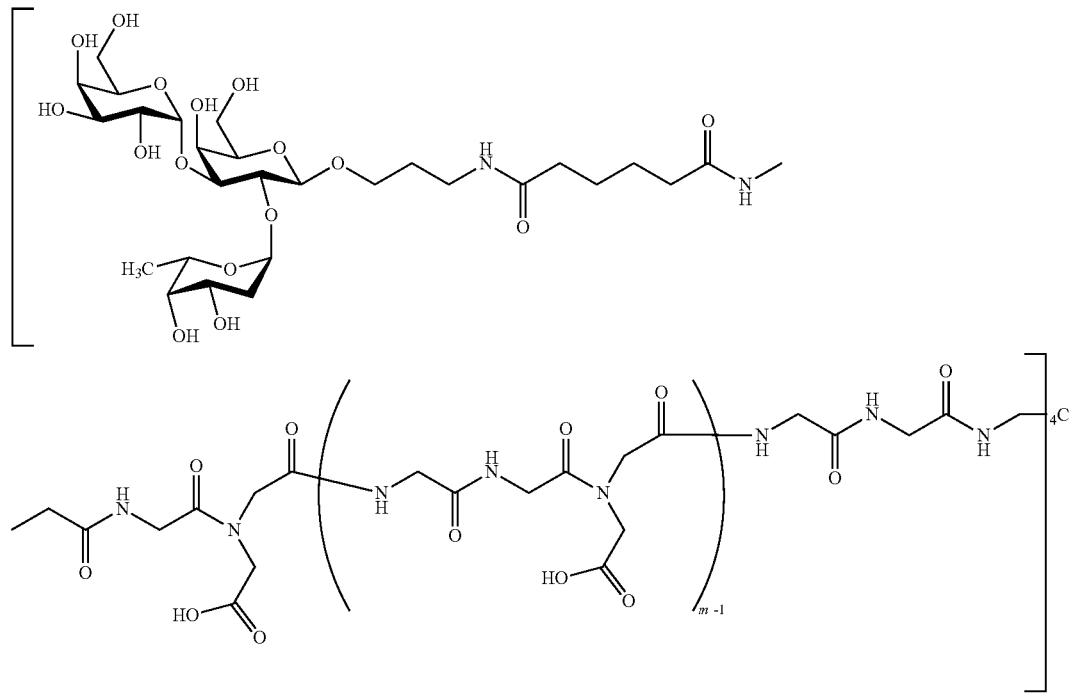

where m is the integer 3 or 5 (53B or 54B) (cf. SCHEME VIIB)

To a stirred solution of a product of Formula II (Table 3; 30 or 31) (2 μmol) in DMSO (0.5 ml) was added B$_{tri}$-S$_1$-S$_2$-Nph (40B) (9.5 mg, 12 μmol) in DMSO (200 μl) and (CH$_3$CH$_2$)$_3$N (3 μL, 21.6 μmol). The mixture was kept for 20 hours at room temperature.

The reaction mixture was diluted with water (1.4 ml), (CH$_3$CH$_2$)$_3$N (65 μL) added, and the mixture kept for 20 hours at room temperature.

The reaction mixture was then evaporated to minimal volume and the residue fractionated on a Sephadex LH-20 column (eluted with 0.2 M NH$_3$ in MeOH/water 1:1 mixture). Fractions containing pure multiligand construct were combined, evaporated to c. 1 ml volume and freeze dried.

Yield of {B$_{tri}$-S$_1$-S$_2$-[Gly$_2$(CMGly)]$_3$Gly$_2$-NHCH$_2$}$_4$C (m is 3) (53B) was 10.6 mg (86%), white solid. TLC: R$_f$=0.37 (3:3:2 (v/v/v) methanol/acetonitrile/water).

$^1$H NMR (500 MHz, [D$_2$]H$_2$O, 30° C.) δ, ppm: 5.271 (d, J=3.6 Hz, 1H; H1 Galα), 5.233 (d, J=3.4 Hz, 1H; H1 Fucα), 4.533 (d, J=7.9 Hz, 1H; H1 Galβ), 4.394 (ddd, J$_6$=6.6 Hz, 1H; H5 Fucα), 4.274-3.669 (together 45H; 6H Galα, 3H Fucα, 6H Galβ, OC$\underline{H}_2$CH$_2$CH$_2$N, 28H peptide chain), 3.246 (m, 2H; OCH$_2$C$\underline{H}_2$CH$_2$N), 2.927 (broad s, 2H; central C—C$\underline{H}_2$—NH), 2.341 and 2.250 (m, 2H; CH$_2$C$\underline{H}_2$CONH), 1.822 (q, 2H; OCH$_2$C$\underline{H}_2$CH$_2$N), 1.600 (m, 4H; C$\underline{H}_2$C$\underline{H}_2$CH$_2$CO), 1.187 (d, J=6.6 Hz, 3H; CH$_3$ Fucα).

Yield of {B$_{tri}$-S$_1$-S$_2$-[Gly$_2$(CMGly)]$_5$Gly$_2$-NHCH$_2$}$_4$C (m is 5) (54B) was 12.7 mg (92%), white solid. TLC: R$_f$=0.62 (1:1:1 (v/v/v) methanol/acetonitrile/water).

$^1$H NMR (500 MHz, [D$_2$]H$_2$O, 30° C.) δ, ppm: 5.270 (d, J=3.6 Hz, 1H; H1 Galα), 5.232 (d, J=3.4 Hz, 1H; H1 Fucα), 4.533 (d, J=7.9 Hz, 1H; H1 Galβ), 4.394 (ddd, J$_6$=6.6 Hz, 1H; H5 Fucα), 4.275-3.668 (together 61H; 6H Galα, 3H Fucα, 6H Galβ, OC$\underline{H}_2$CH$_2$CH$_2$N, 44H peptide chain), 3.246 (m, 2H; OCH$_2$C$\underline{H}_2$CH$_2$N), 2.925 (broad s, 2H; central C—C$\underline{H}_2$—NH), 2.341 and 2.249 (m, 2H; CH$_2$C$\underline{H}_2$CONH), 1.821 (q, 2H; OCH$_2$C$\underline{H}_2$CH$_2$N), 1.600 (m, 4H; C$\underline{H}_2$C$\underline{H}_2$CH$_2$CO), 1.187 (d, J=6.6 Hz, 3H; CH$_3$ Fucα).

Antiviral Activity of Multiligand Constructs of the Ligand Designated 6'SLN

Triligand constructs were tested as inhibitors of influenza virus using the solid-phase fetuin binding inhibition (FBI) assay described by Gambaryan and Matrosovich (1992).

Briefly, virus was adsorbed to the wells of fetuin-coated polystyrene microplates (Costar) at 4° C. overnight and unbound virus washed off.

A volume (0.05 ml) of a solution containing a fixed amount of peroxidase-labeled fetuin and a variable amount of the multiligand construct was added to the plate.

The solutions were prepared in phosphate-buffered saline supplemented with 0.02% bovine serum albumin, 0.02% Tween 80, and 10 μmol of the sialidase inhibitor 4-amino-4-deoxy-Neu5Ac2en.

Plates were incubated for 1 hour at 2 to 4° C., washed, and the amount of peroxidase-labeled fetuin bound determined using the chromogenic substrate o-phenylenediamine.

The dissociation constant (K$_D$) of virus complexed with the multiligand construct was calculated based on the concentration of the sialic acid residues and results averaged (Table 6).

Tetraligand constructs were tested as for triligand constructs and results averaged (Table 7).

Antibody Neutralising Activity of Tetraligand Constructs of the Ligand Designated A$_{tri}$ Tetraligand constructs 53A and 54A were tested as blockers of antibodies directed to the trisaccharide antigen A$_{tri}$ (IgM monoclonals A3) and anti-A antibodies from human blood serum using inhibition ELISA.

The inhibitory activity was compared with an ELISA plate coated with a polyacrylamide conjugate of the trisaccharide antigen $A_{tri}$ (Shilova et al (2005)).

The neutralising activity of tetraligand constructs 53A and 54A was found to be higher than that of polyvalent 30 kDa polymer with pendant trisaccharide antigen $A_{tri}$ ($A_{tri}$-PAA).

Antibody Neutralising Activity of Tetraligand Constructs of the Ligand Designated $B_{tri}$ Tetraligand constructs 53B and 54B were tested as blockers of antibodies directed to the trisaccharide antigen $B_{tri}$ (IgM monoclonals B8) using inhibition ELISA.

The neutralising activity of tetraligand constructs 53B and 54B was found to be higher than that of polyvalent 30 kDa polymer with pendant trisaccharide antigen $B_{tri}$ ($B_{tri}$-PAA).

Although the invention has been described by way of exemplary embodiments it should be appreciated that variations and modifications may be made without departing from the scope of the invention. Furthermore where known equivalents exist to specific features, such equivalents are incorporated as if specifically referred to in this specification.

Fan et al (2000) Chem. Soc., 122, 2663-2664.
Fleischer at al (1971) J. Org. Chem., 36, 3042.
Gambaryan at al (1992) J. Virol. Methods 39, 111-123.
Glick et al (1991) Angew. J. Biol. Chem., 35, 23660-23669.
Jayaraman at al (1997) Chem. Eur. J., 3, 1193-1199.
Kiessling et al (1996) Chemistry & Biology, 3, 71-77.
Korchagina and Bovin (1992) Bioorgan. Khim., 18(2), 283-298.
Litherland at al (1938) J. Chem. Soc., 1588.
Lundquist et al (2002) Chem. Rev., 102, 555-578.
Matrosovich at al (1990) FEBS Lett., 272, 209-211.
Matsuura at al (2004) Chem. Eur. J., 10, 352-359.
McAuley et al (1989) Can. J. Chem., 67, 1650.
Meawell at al (1996) Drug Discovery Today, 1.
Mellet et al (2002) Chem. Eur. J., 8, 1983-1990.
Merritt and Hol (1995) Current Opinion Struct. Biology, 5, 165-171.
Ohta et al (2003) Angew. Ghem. Int. Ed., 42, 5186-5189.
Pazynina et al (2002) Tetrahedron Lett., 43, 8011-8013.
Rini (1995) Ann. Rev. Biophys. Biomol. Struct., 24, 551-577.
Shilova et al (2005) Glycoconj. J., 22, 43-51.

TABLE 6

Relative inhibitory activity of triligand constructs.

| | Virus | | |
|---|---|---|---|
| Inhibitor | A/Nib/23/89M-MA (H1N1)[a] | A/Nib/26/90M (H3N2) | B/Nib/48/90M |
| 6'SLN | 1 | 1 | 1 |
| {6'SLN-$S_1$-$S_2$-[$Gly_2$(CMGly)]$_2$$Gly_2$-$NHCH_2$}$_3$$CCH_3$ (25) | 50 | 4 | 1 |
| {6'SLN-$S_1$-$S_2$-[$Gly_2$(CMGly)]$_3$$Gly_2$-$NHCH_2$}$_3$$CCH_3$ (47) | 300 | 20 | 3 |
| {6'SLN-$S_1$-$S_2$-[$Gly_2$(CMGly)]$_4$$Gly_2$-$NHCH_2$}$_3$$CCH_3$ (48) | 300 | 40 | 4 |
| {6'SLN-$S_1$-$S_2$-[$Gly_2$(CMGly)]$_5$$Gly_2$-$NHCH_2$}$_3$$CCH_3$ (49) | 300 | 75 | 6 |

[a]Influenza A virus, A/Minnesota 18/2003-MA (H1N1) provided the same results.
[b]For the monomeric trisaccharide 6'SLN $K_D$ is 100 μM.

TABLE 7

Relative inhibitory activity of tetraligand constructs.

| | Virus | | |
|---|---|---|---|
| Inhibitor | A/Nib/23/89M-MA (H1N1)[a] | A/Nib/26/90M (H3N2) | B/Nib/48/90M |
| 6'SLN | 1 | 1 | 1 |
| {6'SLN-$S_1$-$S_2$-[$Gly_2$(MCMGly)]$_3$$Gly_2$-$NHCH_2$}$_4$C (44) | 50 | 3 | 1 |
| {6'SLN-$S_1$-$S_2$-[$Gly_2$(MCMGly)]$_4$$Gly_2$-$NHCH_2$}$_4$C (45) | 50 | 5 | 2 |
| {6'SLN-$S_1$-$S_2$-[$Gly_2$(MCMGly)]$_5$$Gly_2$-$NHCH_2$}$_4$C (46) | 50 | 10 | 3 |
| {6'SLN-$S_1$-$S_2$-[$Gly_2$(CMGly)]$Gly_2$-$NHCH_2$}$_4$C | 5 | 0.5 | 0.3 |
| {6'SLN-$S_1$-$S_2$-[$Gly_2$(CMGly)]$_2$$Gly_2$-$NHCH_2$}$_4$C (26) | 100 | 2 | 0.7 |
| {6'SLN-$S_1$-$S_2$-[$Gly_2$(CMGly)]$_3$$Gly_2$-$NHCH_2$}$_4$C (50) | 500 | 50 | 5 |
| {6'SLN-$S_1$-$S_2$-[$Gly_2$(CMGly)]$_4$$Gly_2$-$NHCH_2$}$_4$C (51) | 500 | 100 | 10 |
| {6'SLN-$S_1$-$S_2$-[$Gly_2$(CMGly)]$_5$$Gly_2$-$NHCH_2$}$_4$C (52) | 500 | 200 | 20 |

[a]Influenza A virus, A/Minnesota 18/2003-MA (H1N1) provided the same results.
[b]For the monomeric trisaccharide 6'SLN $K_D$ is 100 μM.

REFERENCES

Alzari et al (1988) Ann. Rev. Immunol., 6, 555-580.
Ascenzi et al (2002) FEBS Lett., 531, 384-388.
Bovin et al (1999) international application no. (publication no. WO 01/02018 A2).
Chinarev et al (1999) *Tetravalent blockers for influenza virus hemagglutinin*. In: "Sialobiology and Other Novel Forms of Glycosylation", Inoue, Inoue, Troy, Eds., Gakushin Publishing Co, Osaka, pages 135-143.
Stahl et al (1995) U.S. patent application Ser. No. 09/658,445 (U.S. Pat. No. 5,470,843).
Tomalia et al (1990) Angew. Chem. IEE, 29, 138-175 (1990).
Tsvetkov et al (2002) Chem., 28, 470-486.
Tuzikov et al (2000) Carbohyd. Chem., 19, 1191-1200.
Tuzikov et al (2003), ChemBioChem, 4, 147-154.
Unverzaght et al (1994) Angew. Carb. Res., 251, 285-301.
Weis et al (1988) Nature., 333, 426-431.
Wou and Jin (2003) U.S. patent application Ser. No. 165,805 (U.S. Pat. No. 6,548,476)

INDUSTRIAL APPLICABILITY

Multiligand constructs for use in diagnostic and therapeutic applications, and intermediate multivalent constructs for use in the preparation of the multiligand constructs are provided.

In particular, tri- and tetra-ligand constructs for use in the inhibition of ligand-receptor mediated events such as viral infection of cells and the initiation of immune responses are provided.

The invention claimed is:

1. A multiligand construct of the structure

where:

F is a ligand for a receptor;

$S_1$ is selected from the group consisting of: 1-amino-$C_{2-4}$-alkyl;

$S_2$ is selected from the group consisting of: —CO(CH$_2$)$_3$CO—, —CO(CH$_2$)$_4$CO—, and —CO(CH$_2$)$_5$CO—;

$S_3$ is of the structure:

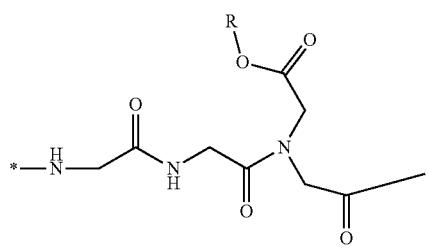

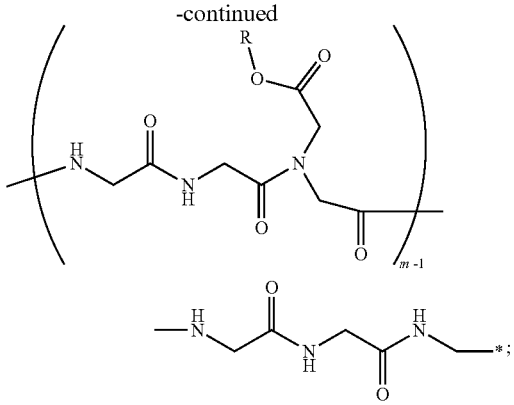

R is CH$_3$ or H;

m is an integer between 1 and 5;

* is a bond; and n is 3 or 4, A is CH$_3$ or is absent, wherein n is 3 when A is CH$_3$ and n is 4 when A is absent.

2. The multiligand construct of claim 1 where the receptor is selected from the group consisting of: influenza virus hemagglutinin (HA), anti-A and anti-B immunoglobulin.

3. The multiligand construct of claim 1 where F is a ligand selected from the group consisting of: Neu5Acα2-6Galβ1-4GlcNAcβ-O-(6'SLN), GalNAcα1-3(Fucα1-2)Galβ-O-($A_{tri}$) and Galα1-3(Fucα1-2)Galβ-O-($B_{tri}$).

4. The multiligand construct of claim 1 where $S_1$ is 1-aminopropyl.

5. The multiligand construct of claim 1 where $S_2$ is —CO(CH$_2$)$_4$CO—.

6. A multiligand construct of claim 1 of the structure:

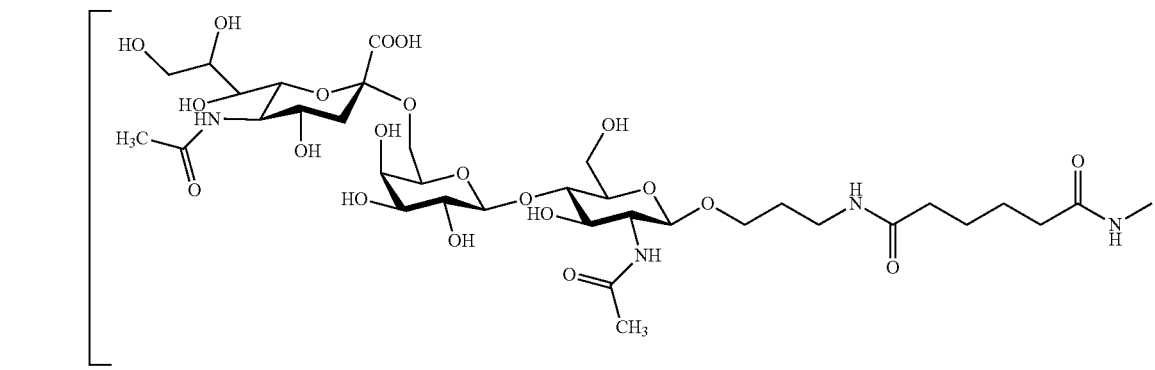

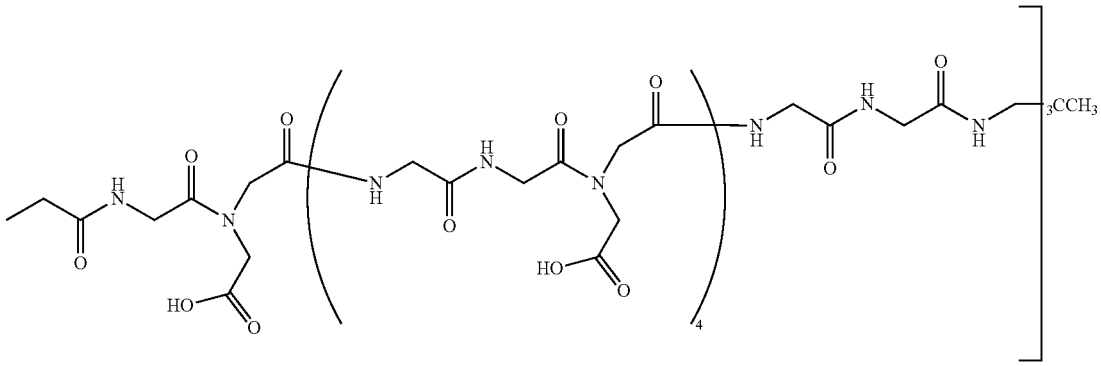

designated {6'SLN-S$_1$-S$_2$-[Gly$_2$(CMGly)]$_5$Gly$_2$-NHCH$_2$}$_3$CCH$_3$.
7. A multiligand construct of claim 1 of the structure:
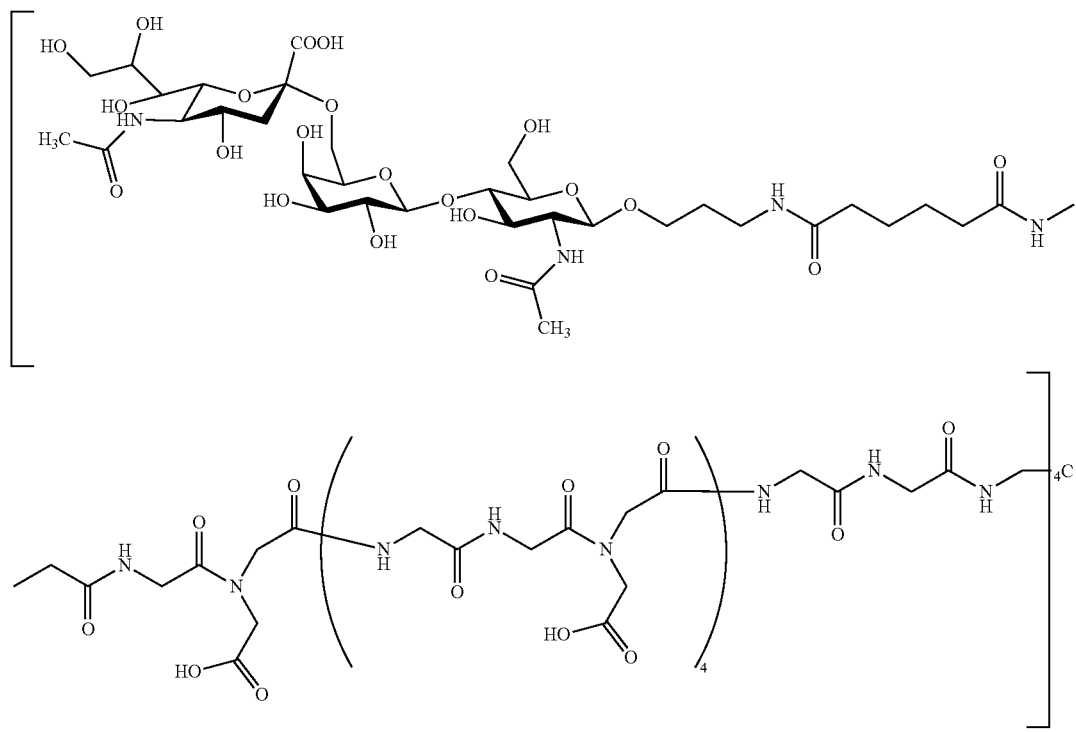
designated {6'SLN-S$_1$-S$_2$-[Gly$_2$(CMGly)]$_5$Gly$_2$-NHCH$_2$}$_4$C.
8. A multiligand construct of claim 1 of the structure:
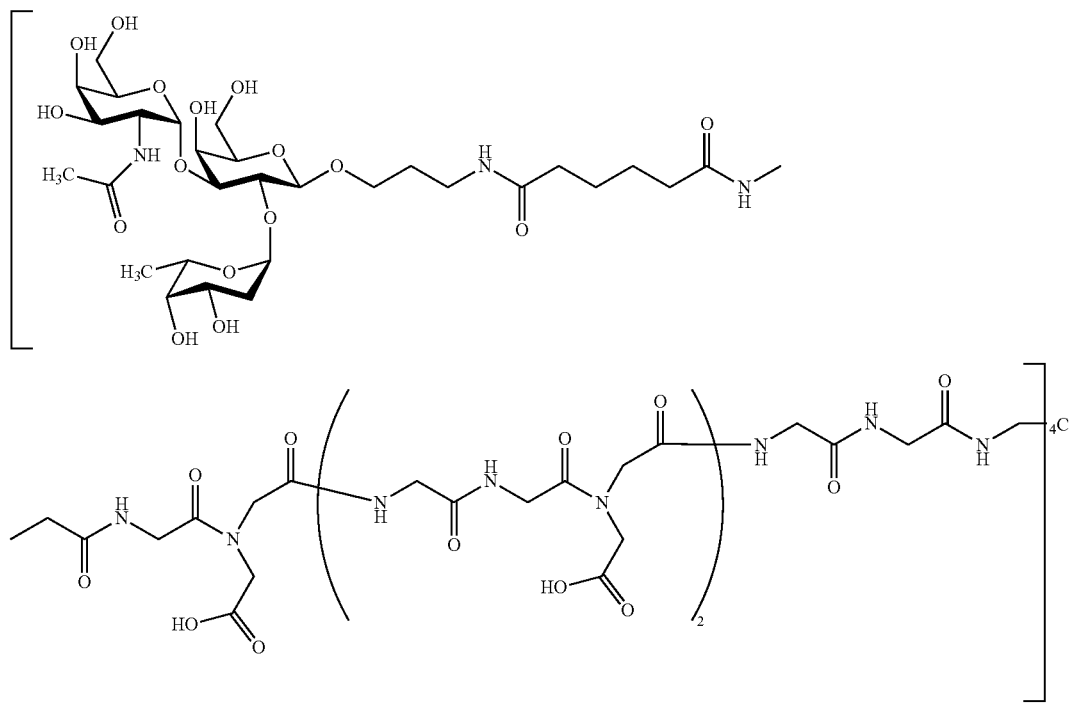

designated {A_{tri}-S_1-S_2-[Gly_2(CMGly)]_2Gly_2-NHCH_2}_4C.
9. A multiligand construct of claim 1 of the structure:
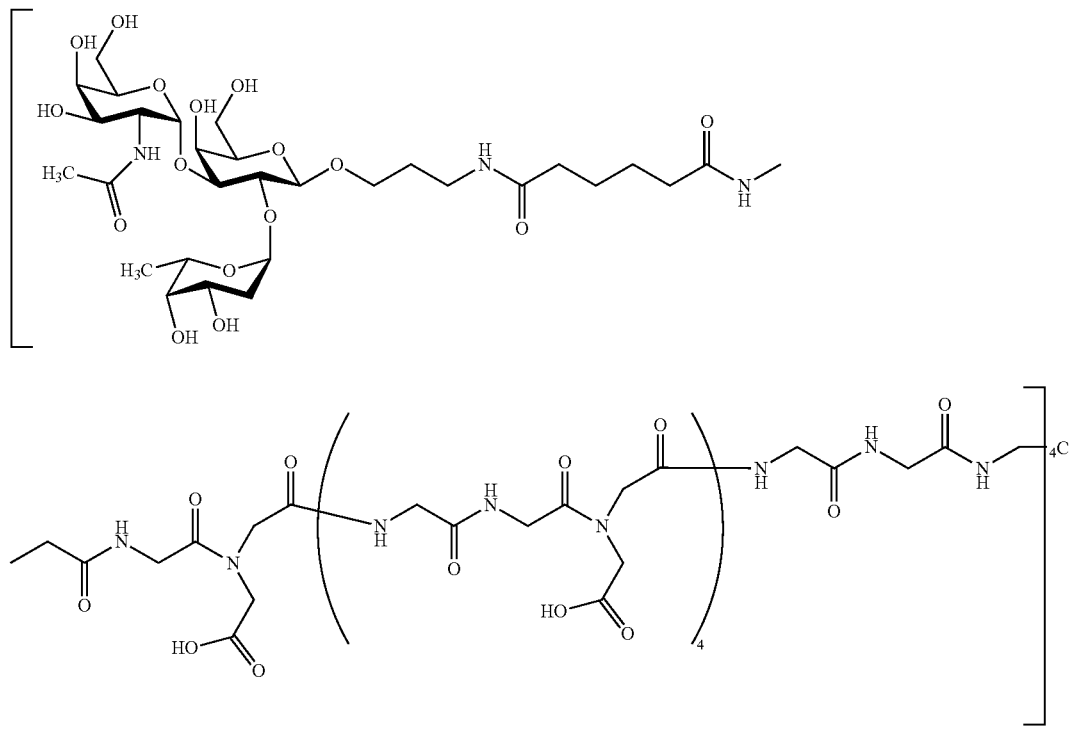
designated {A_{tri}-S_1-S_2-[Gly_2(CMGly)]_5Gly_2-NHCH_2}_4C.
10. A multiligand construct of claim 1 of the structure:
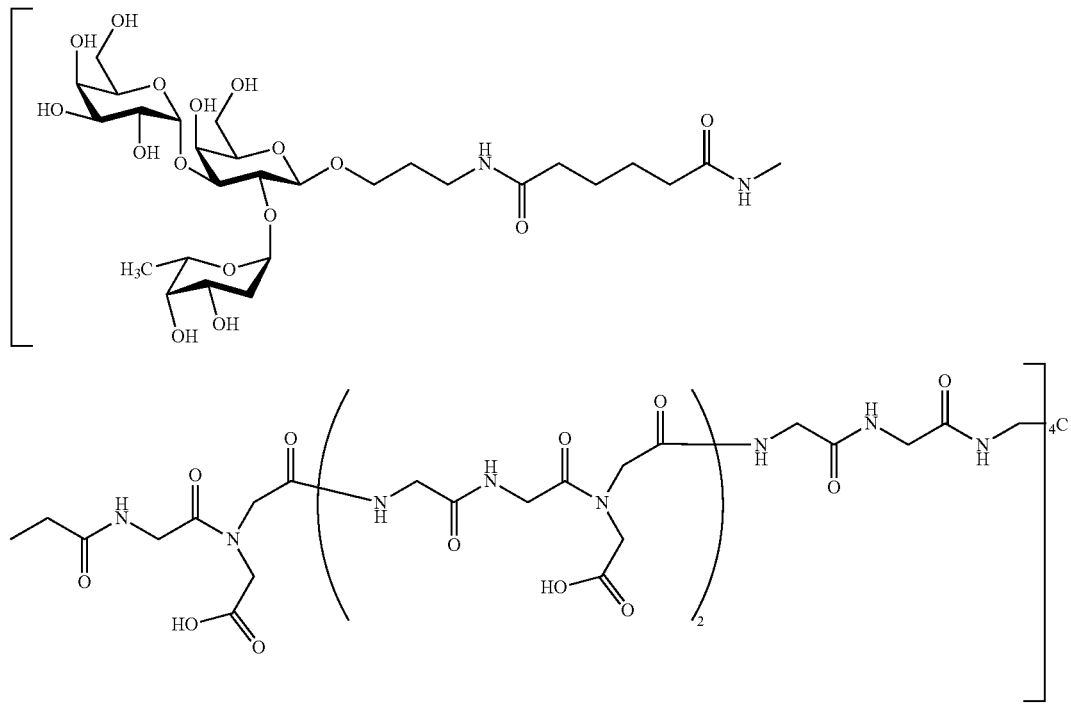

designated {B_tri-S_1-S_2-[Gly_2(CMGly)]_2Gly2-NHCH_2}_4C.
11. A multiligand construct of claim 1 of the structure:
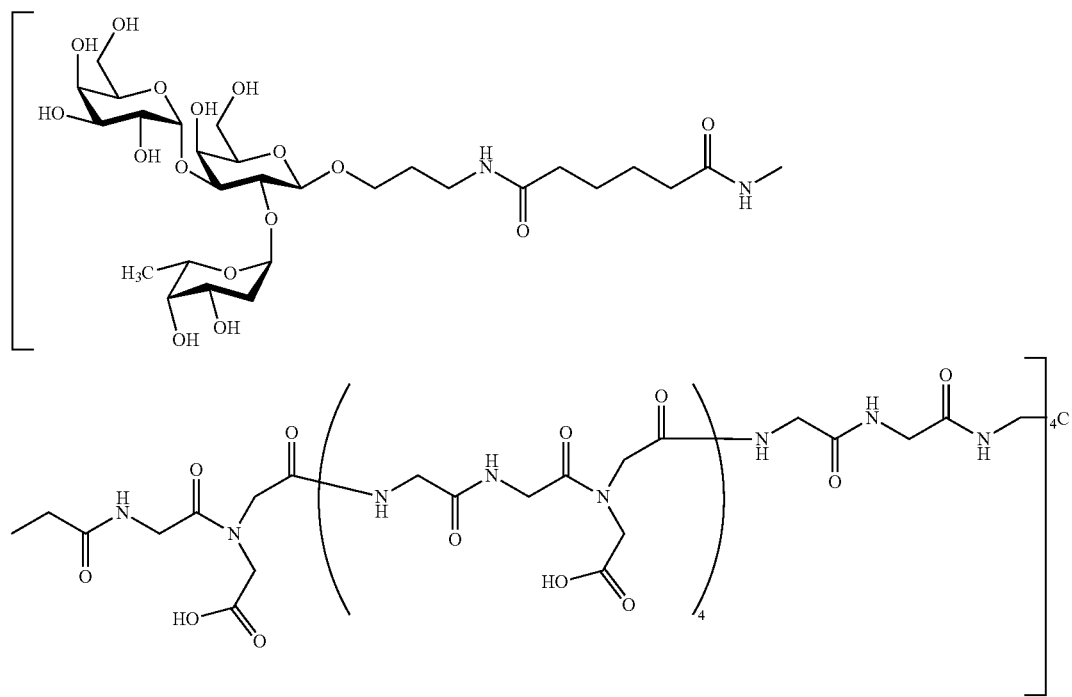
designated {B_tri-S_1-S_2-[Gly_2(CMGly)]_5Gly_2-NHCH_2}_4C.
* * * * *